(12) United States Patent
Drasler

(10) Patent No.: US 10,321,914 B2
(45) Date of Patent: Jun. 18, 2019

(54) POSITIONABLE PERIVALVULAR OCCLUSION DEVICE

(71) Applicant: William Joseph Drasler, Minnetonka, MN (US)

(72) Inventor: William Joseph Drasler, Minnetonka, MN (US)

(*) Notice: Subject to any disclaimer, the term of this patent is extended or adjusted under 35 U.S.C. 154(b) by 255 days.

(21) Appl. No.: 15/622,254

(22) Filed: Jun. 14, 2017

(65) Prior Publication Data

US 2018/0360461 A1    Dec. 20, 2018

(51) Int. Cl.
*A61B 17/12* (2006.01)
*A61M 29/02* (2006.01)

(52) U.S. Cl.
CPC .. *A61B 17/12122* (2013.01); *A61B 17/12031* (2013.01); *A61M 29/02* (2013.01); *A61B 2017/12054* (2013.01)

(58) Field of Classification Search
CPC ........ A61B 17/12122; A61B 17/12031; A61B 2017/12054; A61M 29/02
See application file for complete search history.

(56) References Cited

U.S. PATENT DOCUMENTS

| | | | | |
|---|---|---|---|---|
| 4,327,734 A | * | 5/1982 | White, Jr. ........ | A61B 17/12109 604/907 |
| 4,364,392 A | * | 12/1982 | Strother ............. | A61B 17/0057 604/103.01 |
| 6,997,918 B2 | * | 2/2006 | Soltesz ............ | A61B 17/12022 128/200.24 |
| 7,691,119 B2 | * | 4/2010 | Faman ....... | A61F 2/86 606/159 |
| 8,900,304 B1 | * | 12/2014 | Alobaid ............. | A61B 17/7097 606/92 |
| 9,987,014 B2 | * | 6/2018 | Gray ................. | A61B 17/12136 |
| 10,238,492 B2 | * | 3/2019 | Drasler ................... | A61F 2/246 |
| 2003/0028209 A1 | * | 2/2003 | Teoh ................ | A61B 17/12022 606/191 |
| 2007/0010863 A1 | * | 1/2007 | Stenzel ................. | A61M 29/02 623/1.1 |
| 2009/0028923 A1 | * | 1/2009 | Muni ..................... | A61B 17/24 424/434 |
| 2009/0227983 A1 | * | 9/2009 | Griffin ............. | A61M 25/0051 604/526 |
| 2011/0022149 A1 | * | 1/2011 | Cox .................. | A61B 17/12181 623/1.11 |
| 2012/0221089 A1 | * | 8/2012 | Drasler ................... | A61F 2/958 623/1.11 |
| 2013/0261658 A1 | * | 10/2013 | Lorenzo ............. | A61B 17/1214 606/200 |
| 2014/0074142 A1 | * | 3/2014 | Khieu ...................... | A61F 5/003 606/192 |
| 2014/0172003 A1 | * | 6/2014 | Goepfrich .............. | A61M 29/02 606/192 |
| 2015/0173898 A1 | * | 6/2015 | Drasler ................. | A61F 2/2418 623/2.18 |

* cited by examiner

Primary Examiner — Phong Son H Dang

(57) ABSTRACT

An occlusion device intended for blocking perivalvular leak channels that are found following heart valve implantation between the heart valve and the surrounding tissue. The occlusion device has a stent and a covering that is attached to the stent surface. A blocking fabric extends across the lumen of the stent to block blood flow. The stent pattern and wall structure provide for small radius of curvature bends to fill narrow channels that cause the perivalvular leaks.

20 Claims, 48 Drawing Sheets

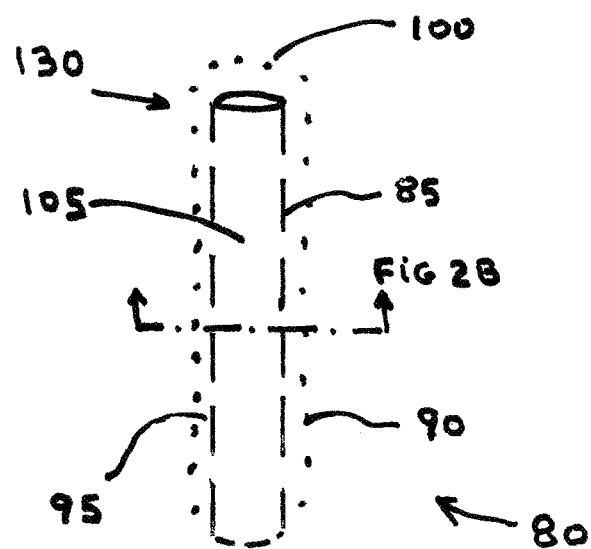

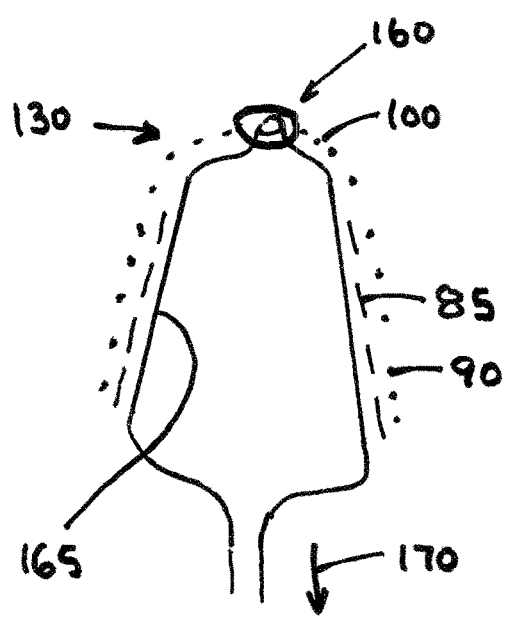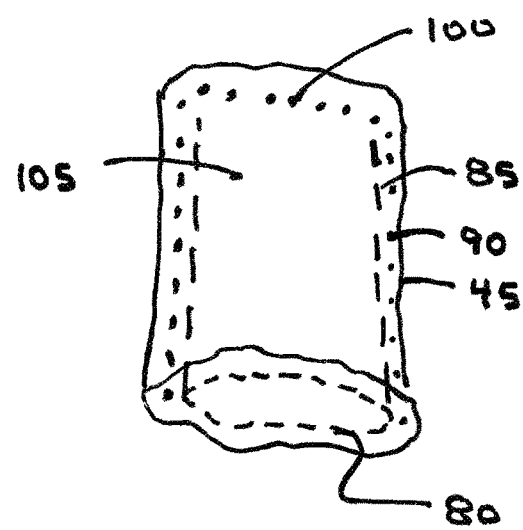

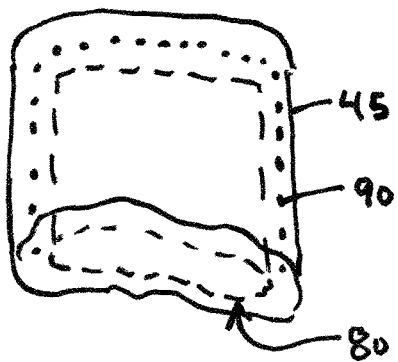
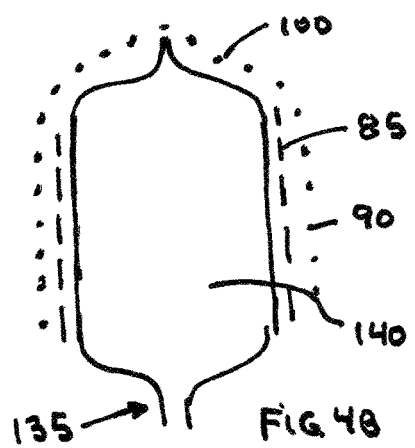
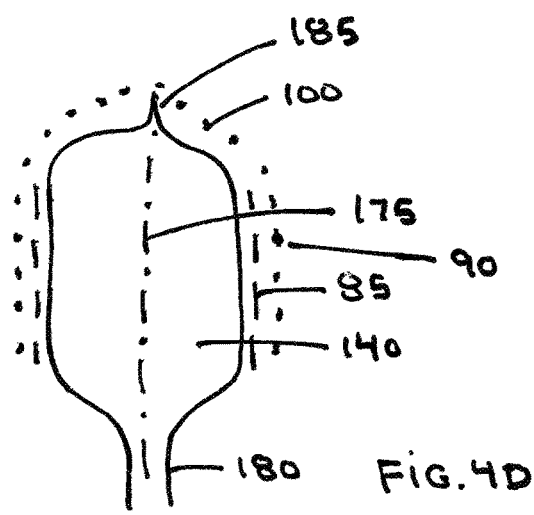
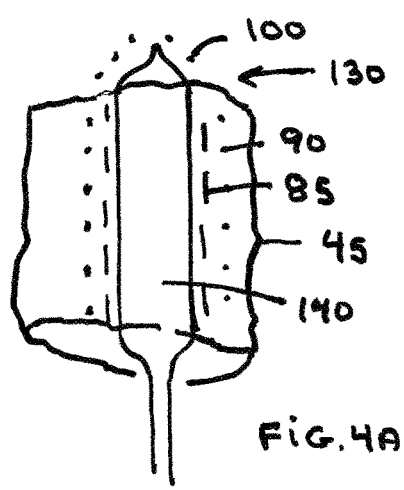

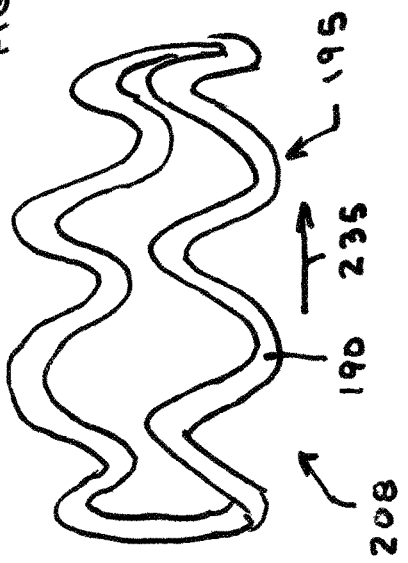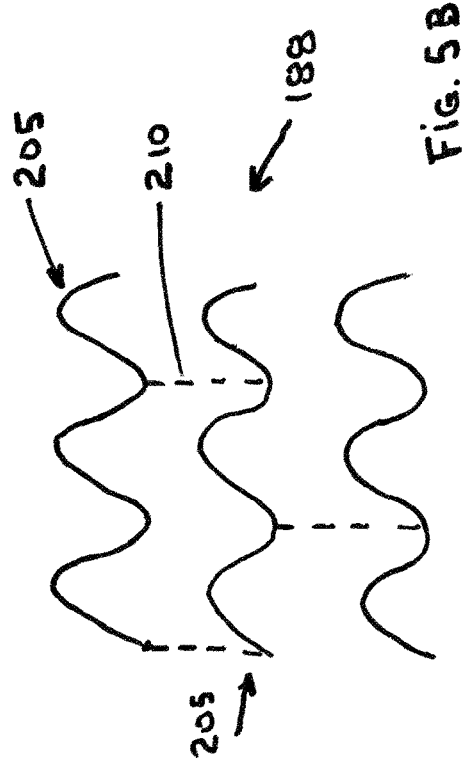

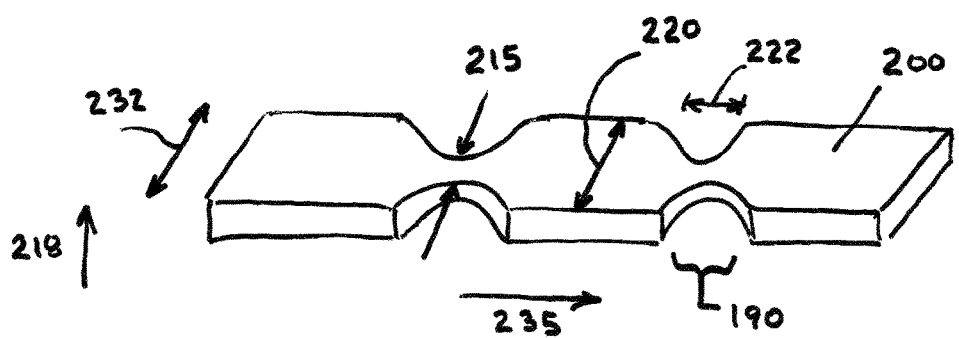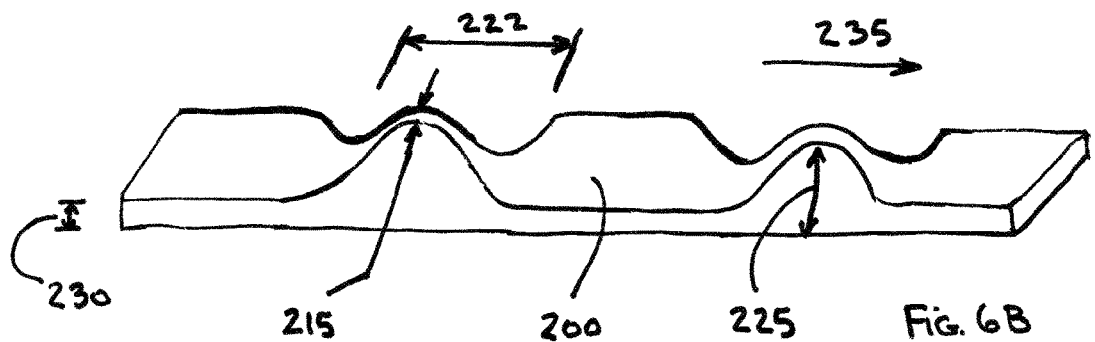

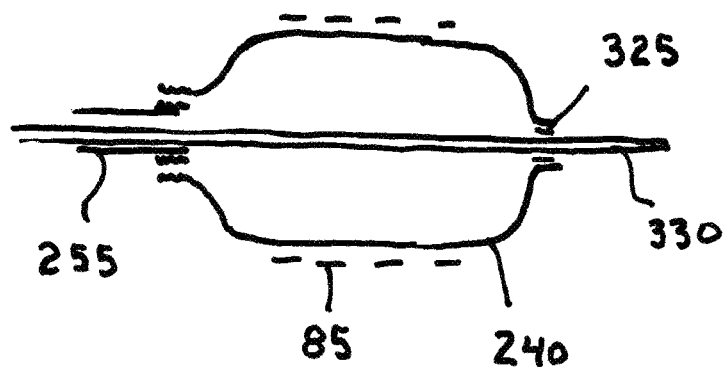

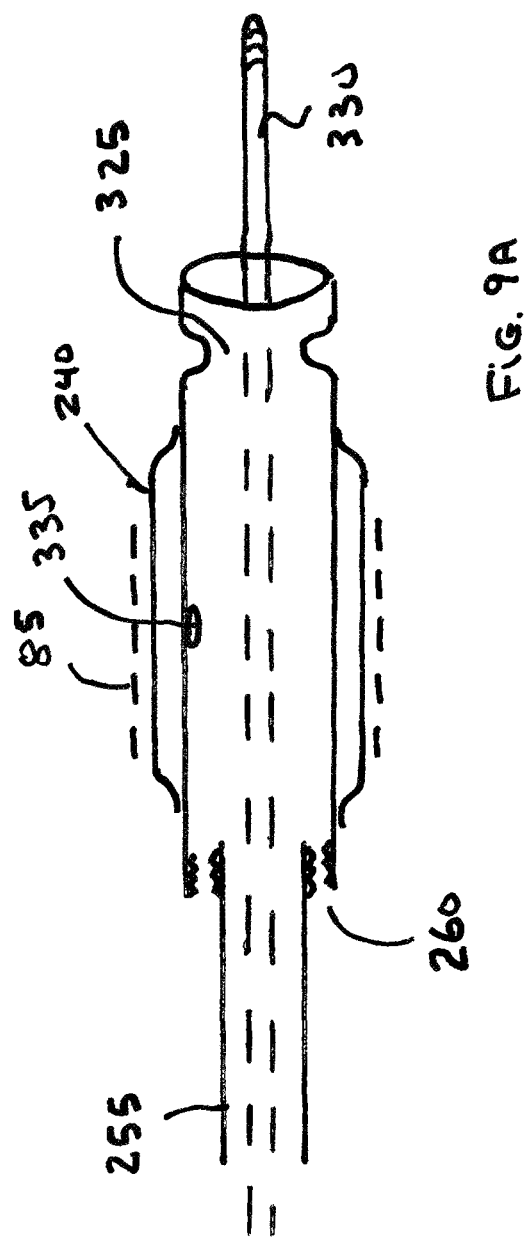

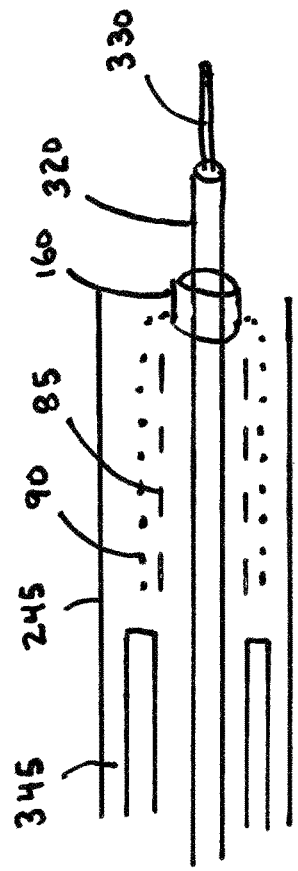
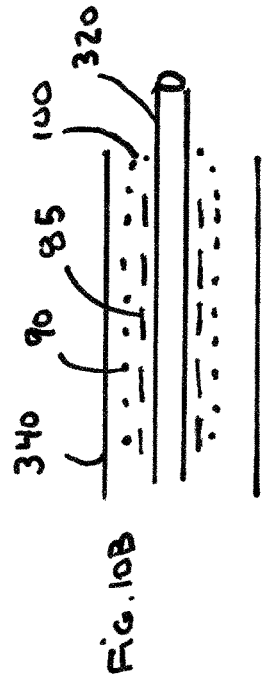
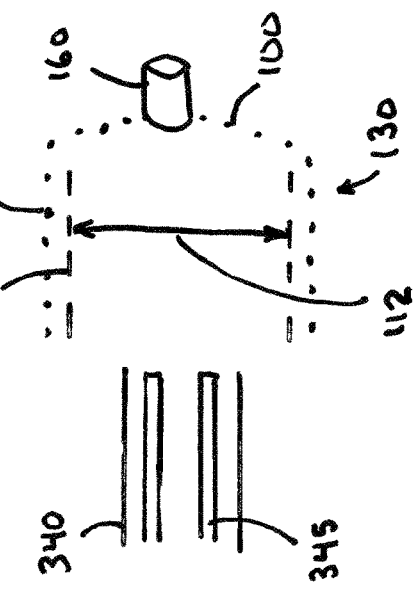

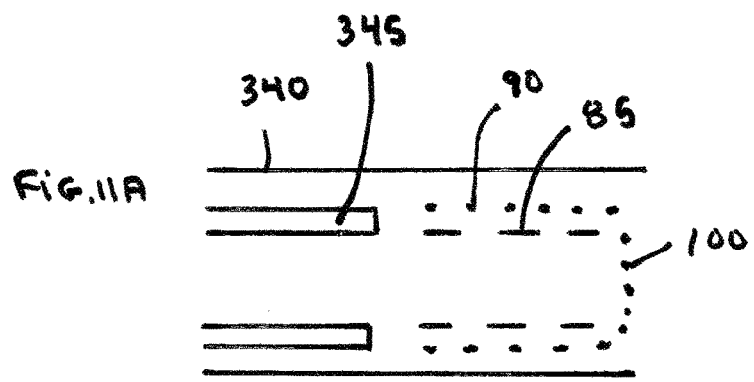
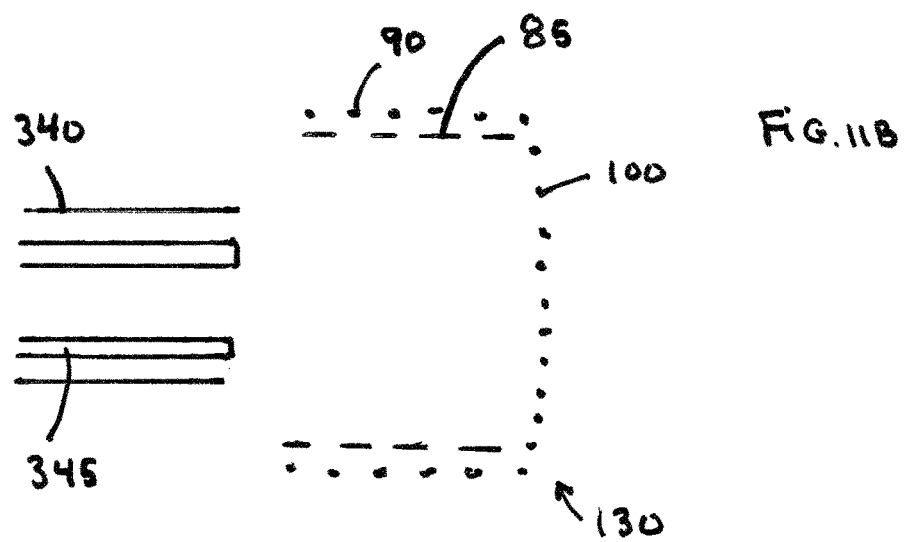
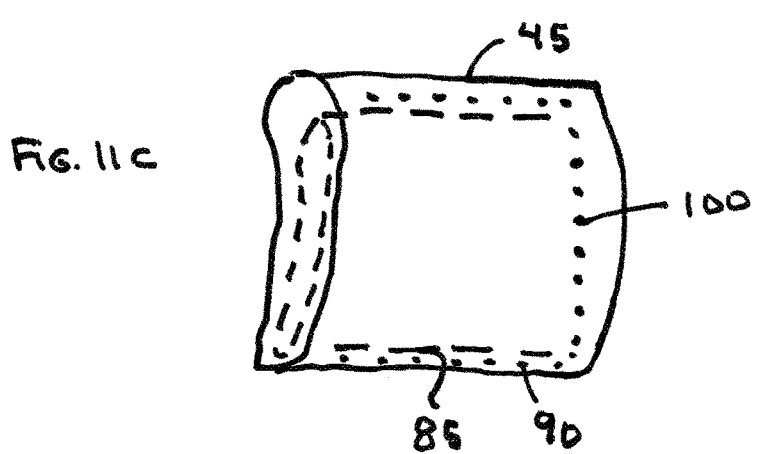

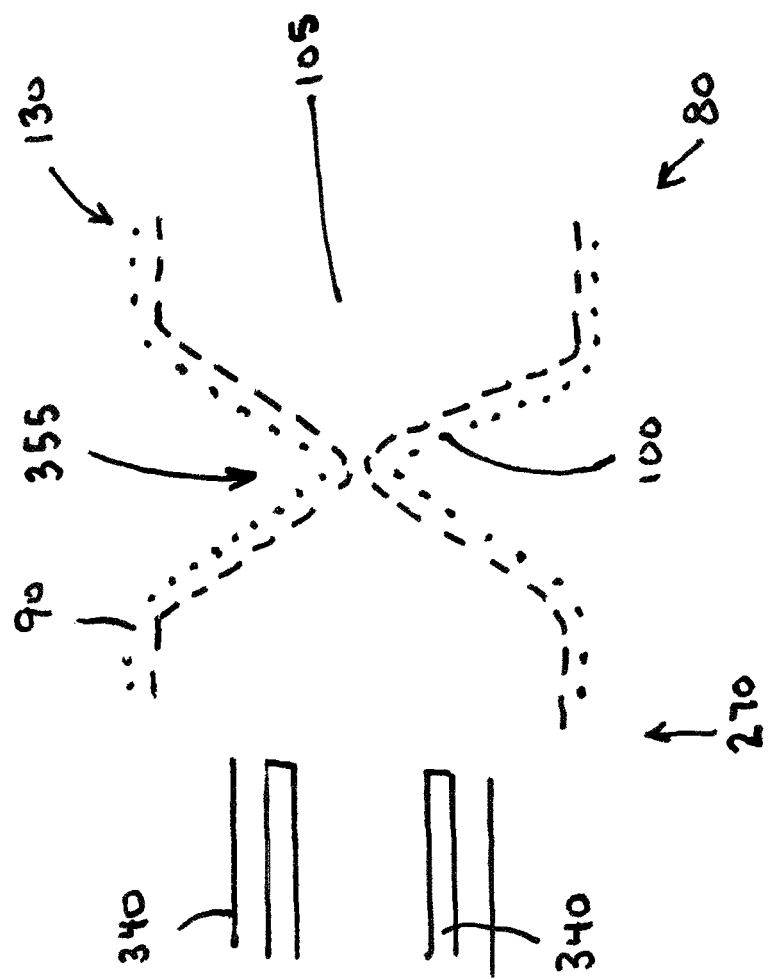

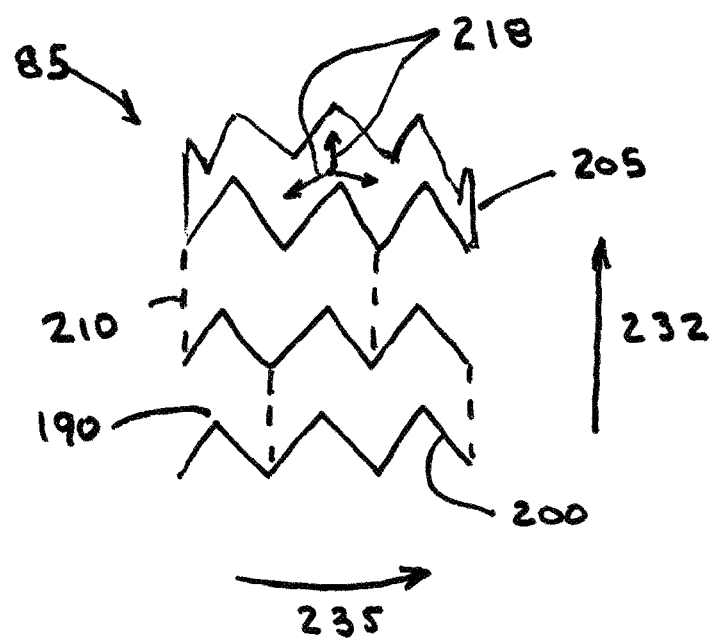

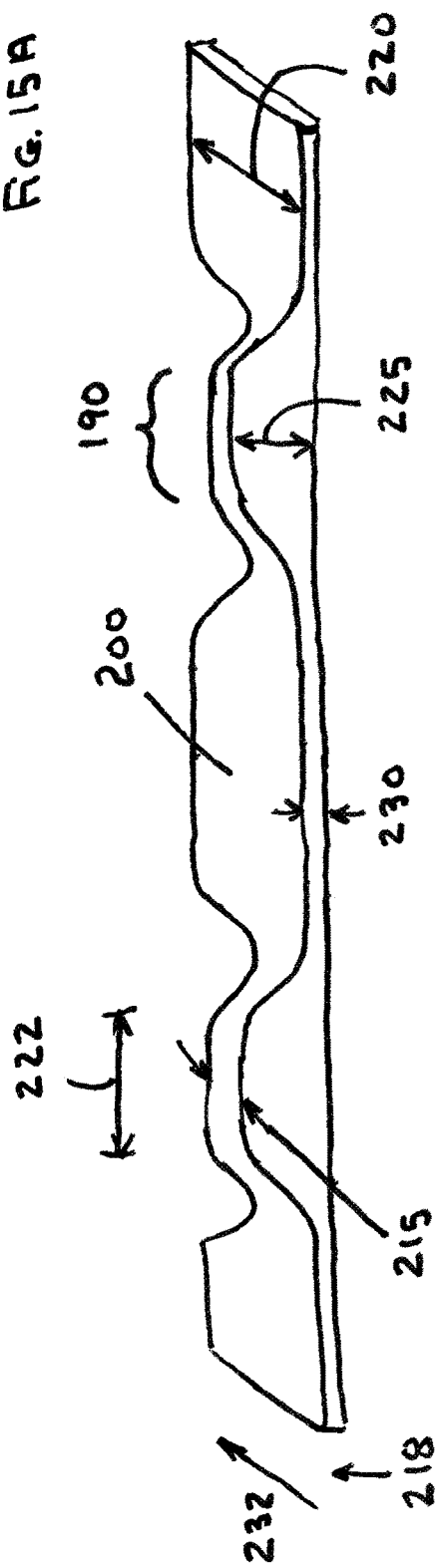
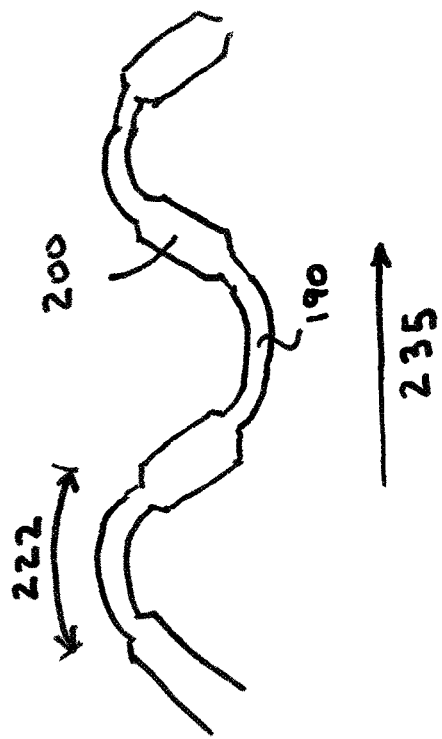

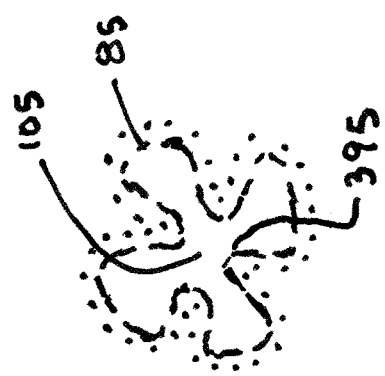
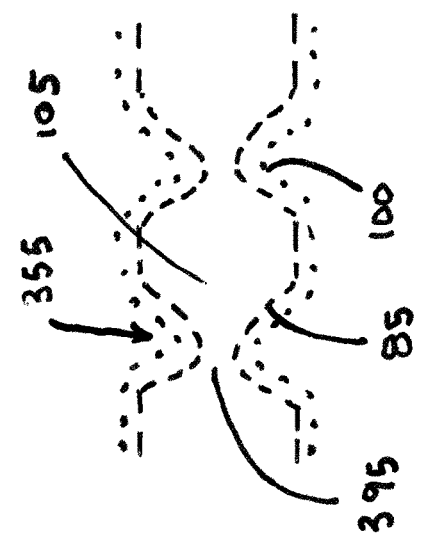
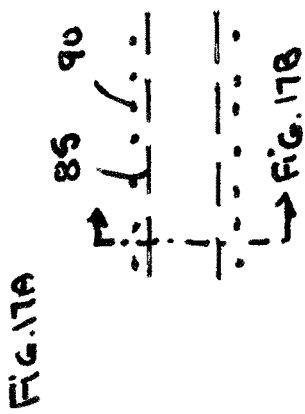

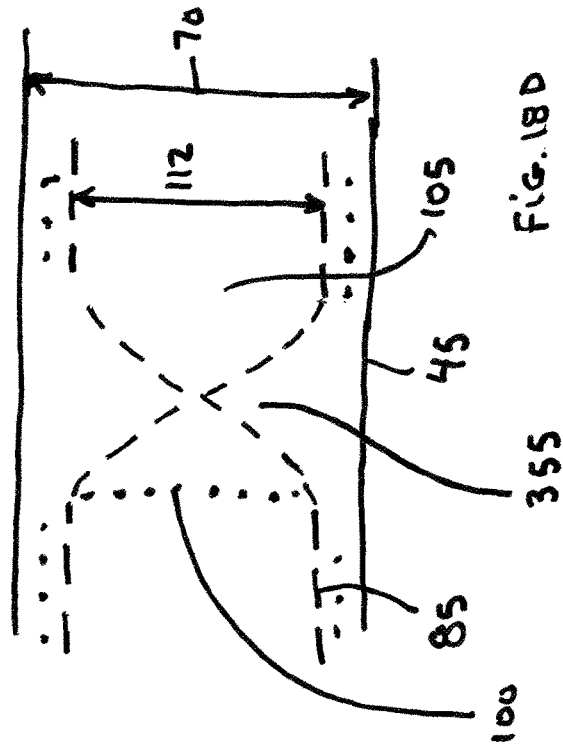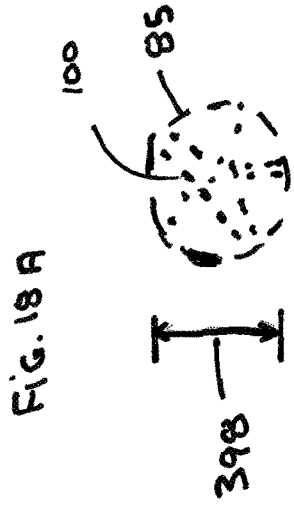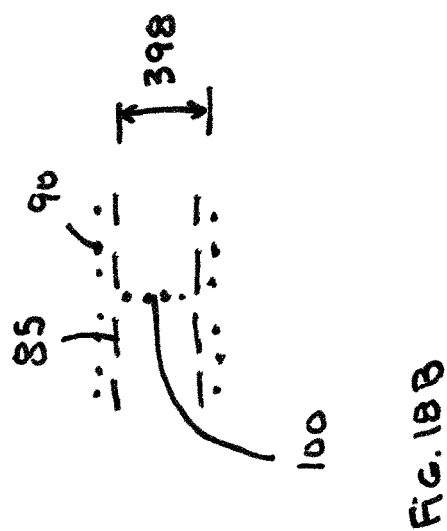

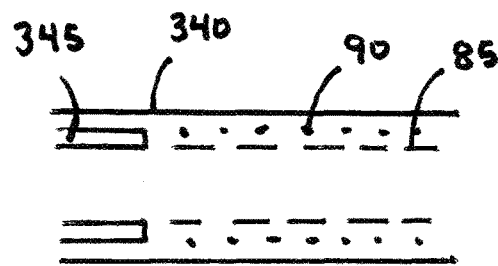
FIG. 19A
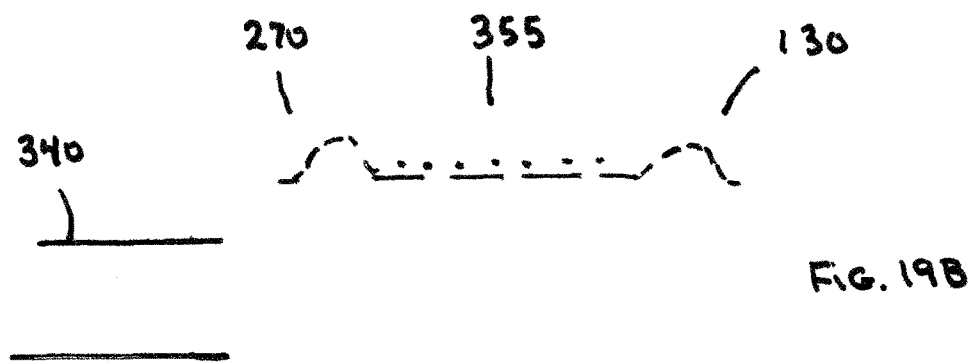
FIG. 19B
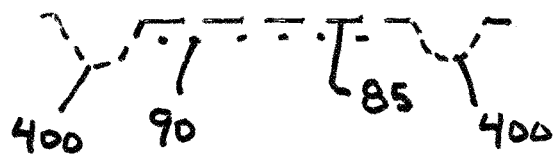
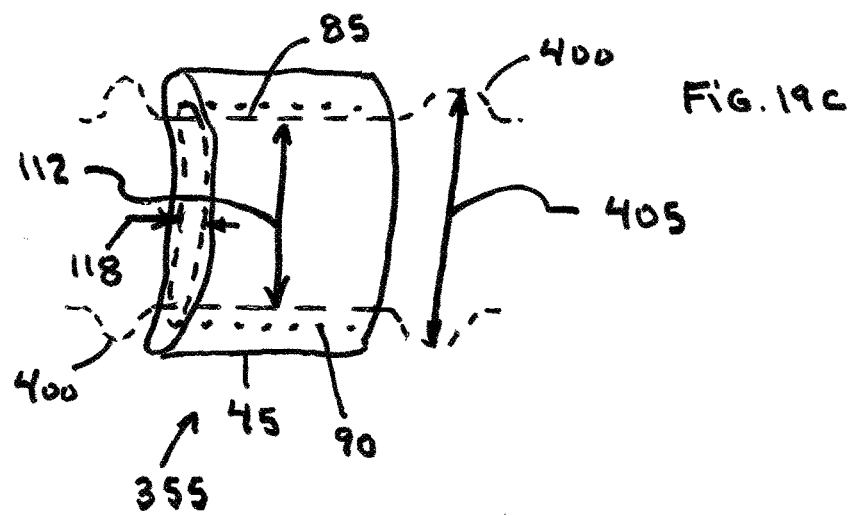
FIG. 19C

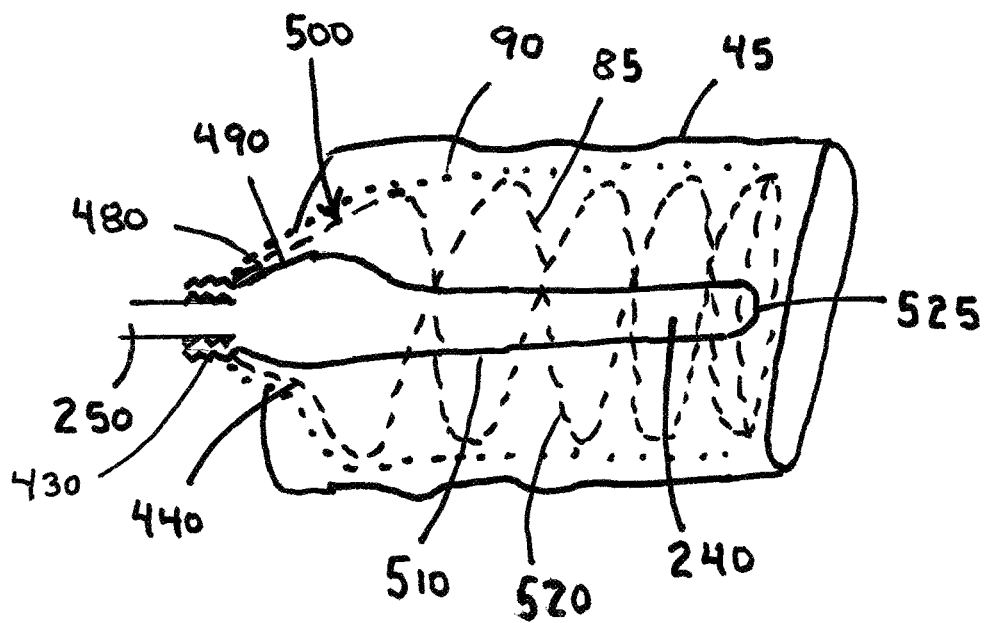

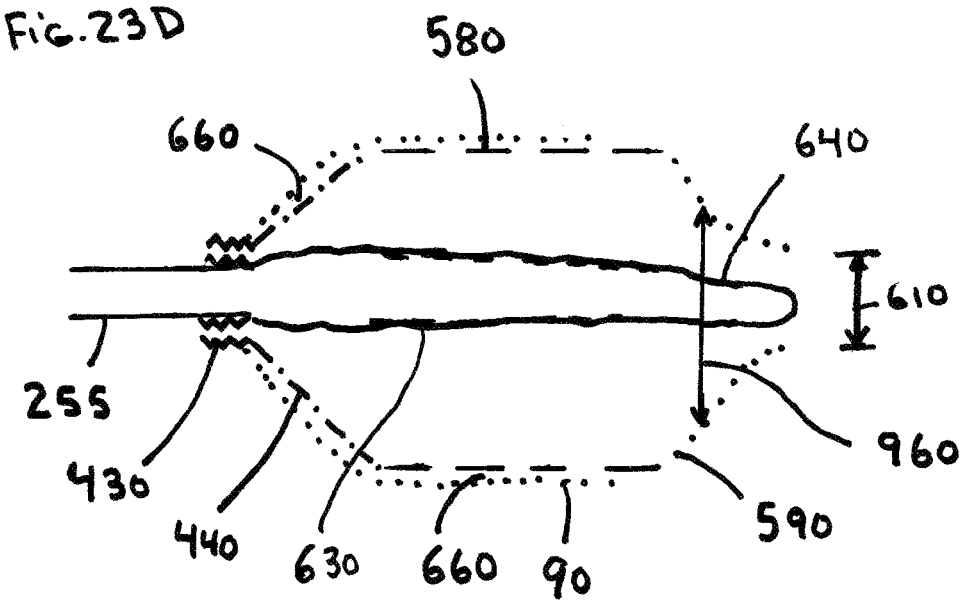
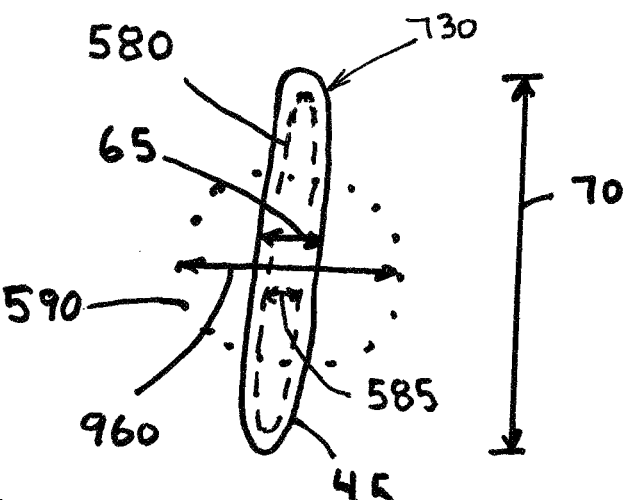

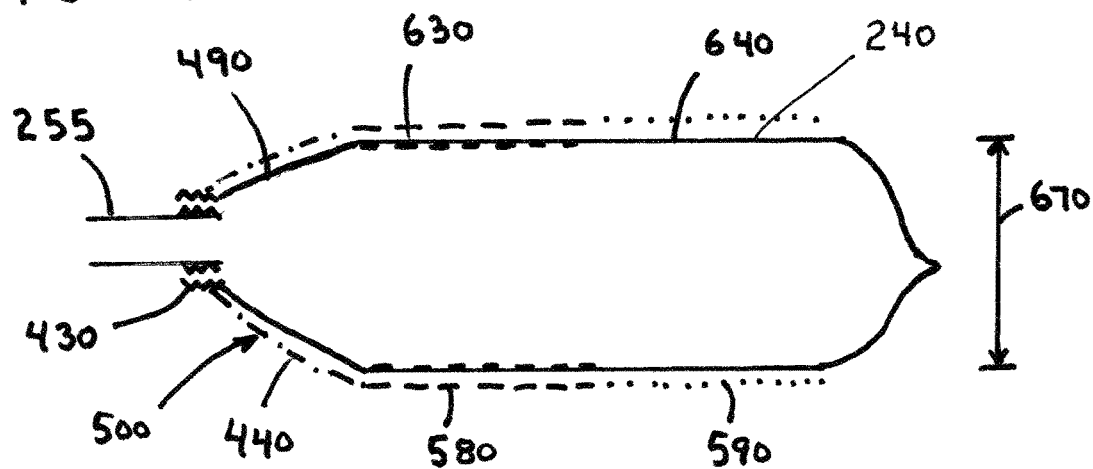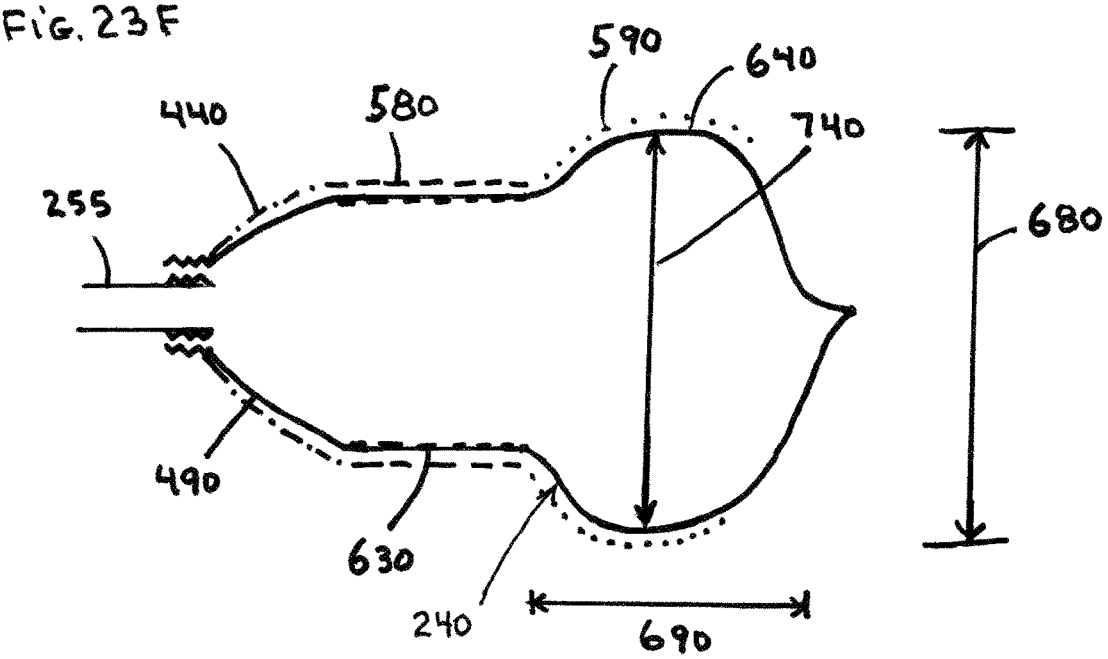

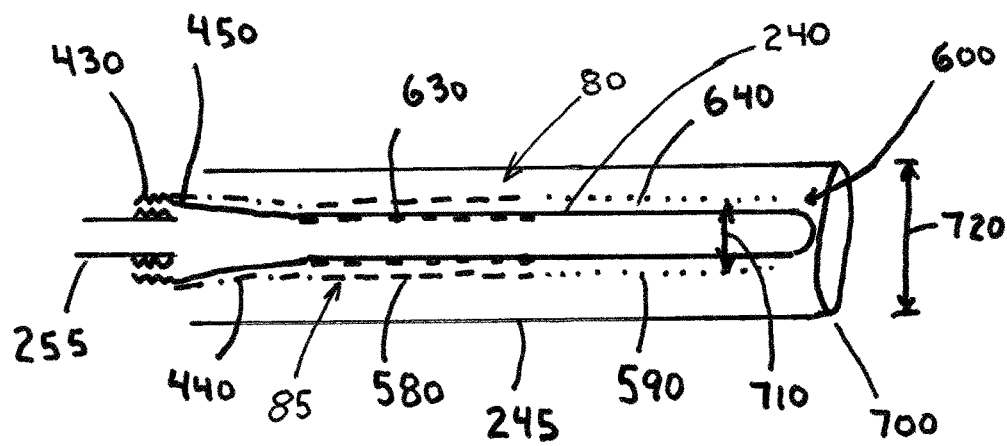
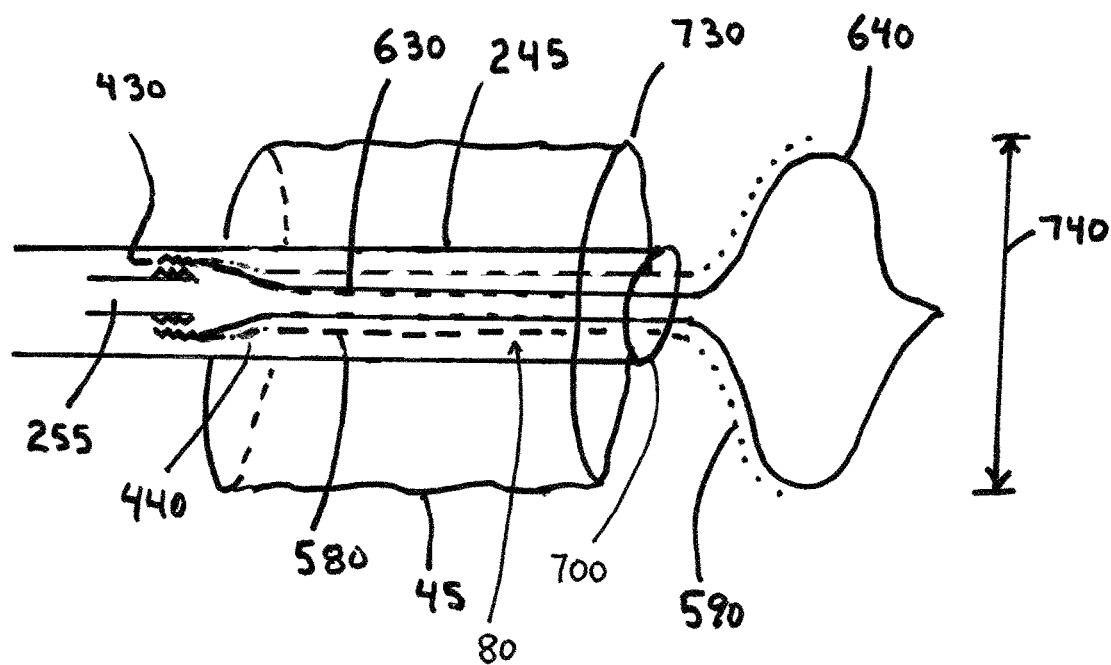

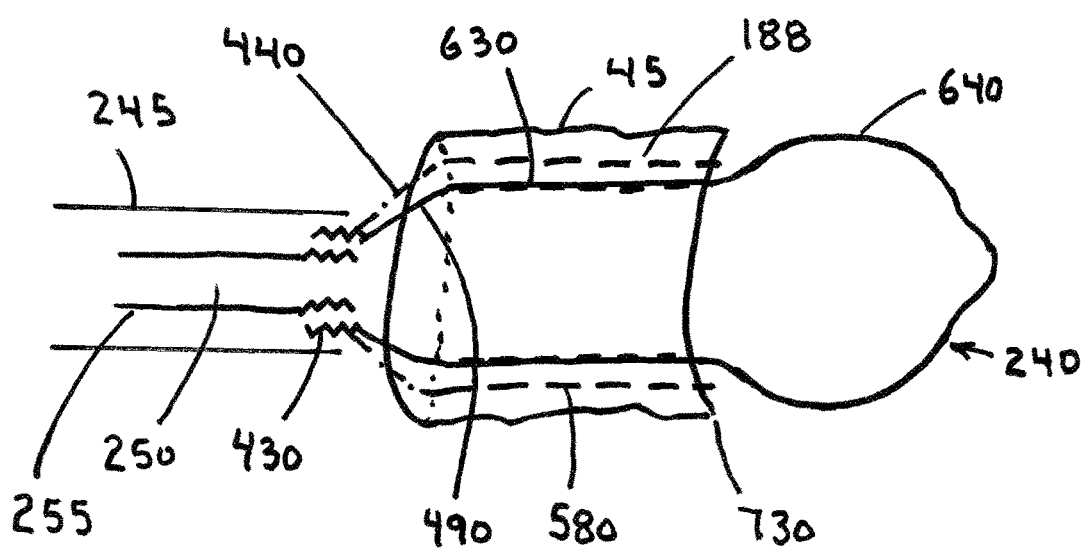

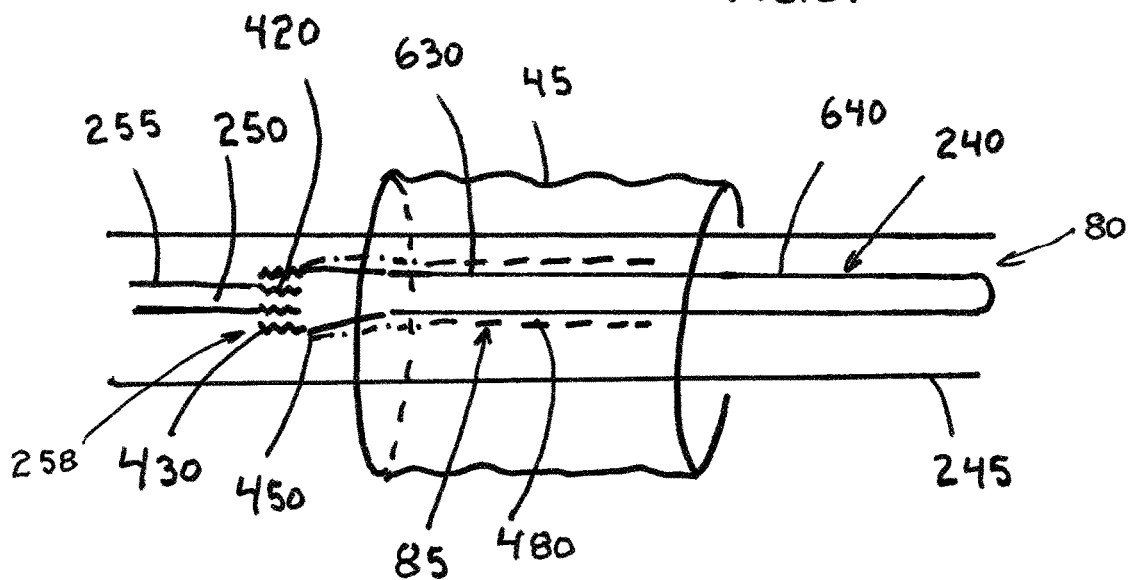
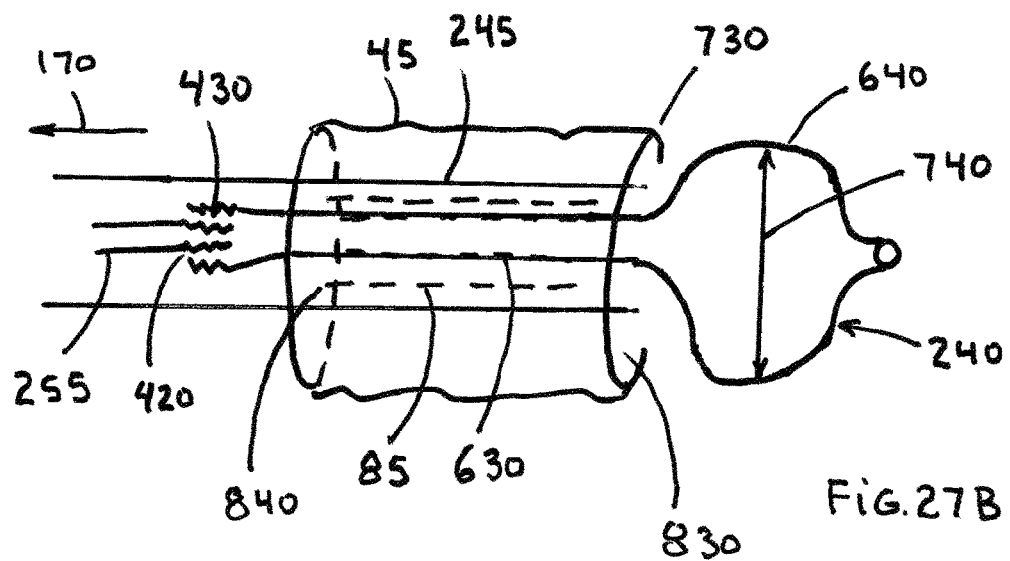

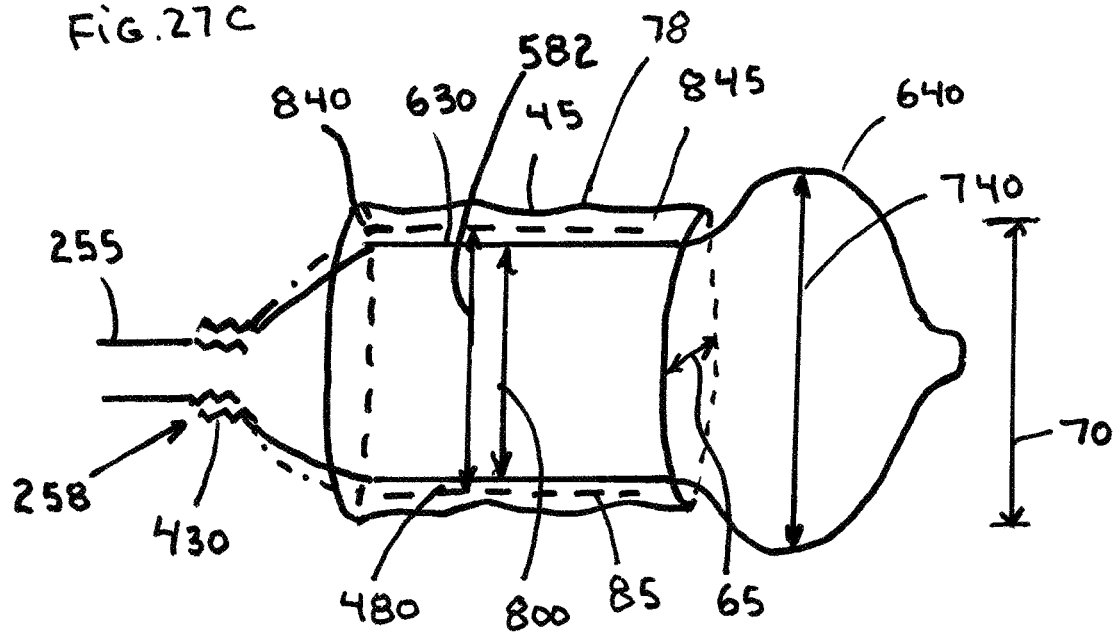
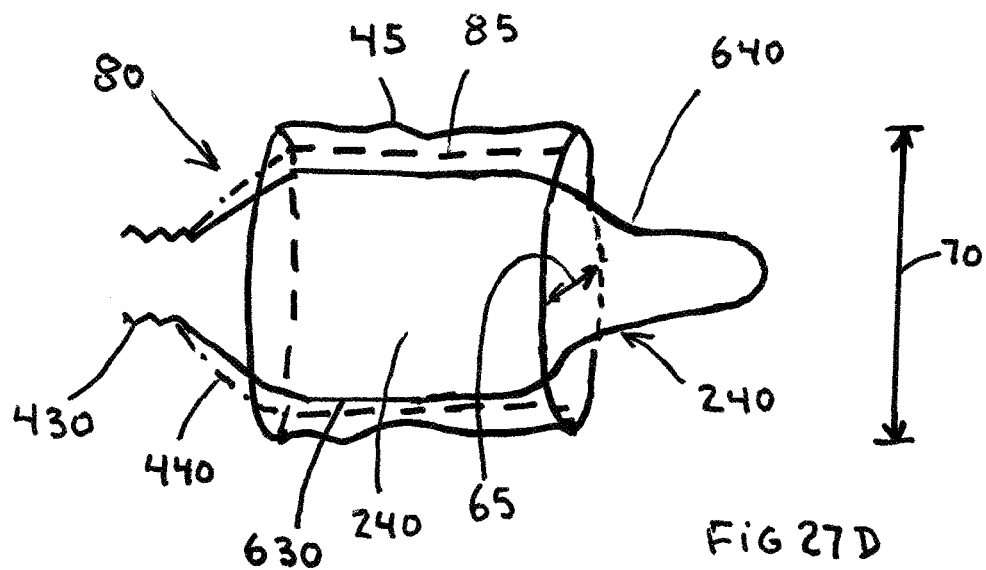

POSITIONABLE PERIVALVULAR OCCLUSION DEVICE

CROSS REFERENCE TO RELATED APPLICATIONS

This patent application makes reference to and thereby incorporates all information found in the provisional patent applications No. 62/496,588 entitled Retrievable Perivalvular Occlusion Device and Methods, filed 21 Oct. 2016 and 62/497,714 entitled Positionable Perivalvular Occlusion Device both by William J. Drasler, and nonprovisional patent application Ser. No. 15/252,395 entitled Perivalvular Occlusion Device and Methods filed 31 Aug. 2016 by William J. Drasler.

BACKGROUND OF THE INVENTION

The implantation of Transcatheter Aortic Valve Replacement (TAVR) devices and Transcatheter Mitral Valve Replacement (TMVR) devices has provided significant opportunity for improved health for those patients that are too sick to undergo surgical valve replacement or those who are of significant age of which the trauma associated with surgical replacement does not merit the potential benefits of surgical replacement over transcatheter valve replacement. Although improvements are continuously being made in the TAVR and MTVR devices and their procedures, the presence of leakage of blood across the transcatheter valve in a retrograde direction has raised clinical concerns including the potential increased mortality due to such perivalvular leakage. Such blood leakage is also found with the use of standard surgical valve in the aortic and mitral positions. Occlusion devices have been used to block perivalvular leaks that occur following the implantation of surgical and transcatheter aortic and mitral valves however the occlusion devices can themselves cause problems to occur. These devices are not optimally designed for blockage of the thin, oval, crescent-shaped opening that occurs in perivalvular leaks. A typical standard occlusion device often will have a circular cross section and is not specifically intended to undergo a shape change during expansion that will fill the voids found in a channel that has an oval or crescent-shaped cross section. Also, the current occlusion devices typically have flanges on either end of the device to prevent such devices from migrating; these flanges tend to interfere with valvular function and with blood flow through the valve. What is needed is an occlusion device that conforms to a thin, crescent-shaped opening, blocks blood flow through such opening, cannot migrate, and does not interfere with valvular function and blood flow through the valve.

SUMMARY

The present invention is an occlusion device that is intended to block blood flow through a thin, crescent-shaped perivalvular leak path or channel that occurs around a surgically implanted aortic valve or a mitral valve, or around a TAVR or TMVR device. Several embodiments of balloon expandable (BE) systems and self-expanding (SE) systems of the present invention are described. In general the device consists of a stent-like structure that is delivered to the perivalvular leak in a small configuration and is enlarged to fill the thin, crescent-shaped leak path of the perivalvular leak. The stent or stent-like structure contains a covering material attached to the stent and a blocking fabric that extends across the cross section of the stent. The covering and blocking fabric are formed from thin blood resistant material that serves to block blood flow through the stent wall and/or through the stent lumen, and hence block the perivalvular leak that extends through the channel. The blocking fabric can be contiguous with the covering material and can extend over one of the open ends of the stent. The covering can be a polymeric film that is similar to a dilation balloon material and can hold pressure. Alternately, in some embodiments the cover can be a fabric that is formed from a porous material that will eventually become occluded and thereby result in occlusion of the leak channel.

Although most of the discussion found in the present specification is directed toward blockage of a perivalvular leak that occurs around a TAVR device, it is understood that the discussion applies also to leaks that can occur around any implanted valve of the heart including surgically implanted valves and transcatheter devices, and also the device of the present invention can be used to block blood-flow leaks or other fluid leaks found around the outside of any implanted device or in some cases within an implanted device. The present occlusion device is delivered via a percutaneous or transcatheter approach to the vasculature or other vessel of the body.

A perivalvular leak is generally created by the presence of a channel that extends along the outside of a TAVR device or surgically implanted valve (or other implanted device); the channel is often found to have an oval or crescent-shaped cross section; the major axis of the oval extends around a portion of the perimeter of the implanted valve for a distance of several millimeters (range 1-10 mm) in the circumferential direction. The minor axis of the oval channel extends in the radial direction and is generally smaller in dimension (approximate range 0.5 mm to 3 mm), but is large enough such that the blood flow in a retrograde direction across the valve is enough to cause clinical concern to the patient that can influence patient mortality. The ratio of the channel major axis distance to the channel minor axis distance is 3:1 (range 2:1 to 8:1). The axial length of the channel in an axial direction extends along the length of the TAVR device or implanted valve and can range from approximately 3 mm to over 15 mm.

The channel that forms the perivalvular leak has a generally undulating shape throughout the surface of the channel. The cross section is generally not formed as a perfect oval but instead has many undulation protrusions and cavities that can be formed from calcium deposits located along the native valve leaflets. Such undulation also extends along the axial length of the channel. The stent structure of a TAVR device or the sewing ring of a surgical valve can also form undulations in the channel shape that can protrude into the channel or form pockets and cavities that make up the surface of the perivalvular channel. The present invention is intended to extend into and around these cavities and protrusions to form a tight fit into the undulations that will prohibit migration of the occlusion device and will improve the ability of device to block blood flow through the channel.

The present invention is specifically designed to fill an oval channel that is thin (0.5-3 mm) in its minor axis distance (typically in the radial direction for a TAVR device), long (1-10 mm) in its major axis distance (typically extending in the circumferential direction along a portion of a perimeter for a TAVR device), and having an axial length of 3 to more than 15 mm in axial length. The device is delivered to the perivalvular leak site in a small diameter configuration and is expanded out via either a balloon inflation method or via a self-expansion of a stent-like structure or stent to fill the oval void of the channel cross section. The stent is designed to fill in the voids and nonuniform spaces found within the channel such that the occlusion device will not migrate once it is expanded and released into the channel. A covering or blocking fabric that is attached to least a portion of the stent will extend into the blood-flow path of the channel to block blood flow through the channel.

In one embodiment, the occlusion device is a stent with a generally cylindrical shape in its nondeployed small diameter configuration and having a covering attached along a portion or along its entire cylindrical surface. The covering also extends across one end of the stent and forms a closed covering end that will block blood flow after the device has been expanded to a larger diameter within the perivalvular leak channel. The stent and covering can be loaded onto a balloon catheter having an expandable balloon located at its distal end. The balloon catheter can be an over-the-wire catheter such that it is able to follow over a standard guidewire that is initially placed across the perivalvular leak channel. The closed covering is designed with a small flapper valve to allow a guidewire to pass through the covering but upon removal of the guidewire, the closed covering will block blood passage through the occlusion device.

The expandable balloon located at the end of the balloon catheter is formed from an elastomeric material such that it can reduce in diameter back to its original low diameter and cylindrical profile upon deflation. The low profile for the balloon allows it to be removed from the thin oval channel without causing friction against the occlusion device that could cause the implanted occlusion device to migrate during the removal of the balloon catheter following balloon inflation to expand the occlusion device and subsequent deflation of the balloon prior to catheter withdrawal. The balloon can be formed with a generally tapered or conical shape with a smaller balloon diameter at the distal end of the balloon to provide a relief for the balloon upon withdrawal from the narrow or thin oval channel without causing frictional drag that could cause migration of the occlusion device upon removal of the balloon catheter. The balloon can be coated with a lubricious coating to reduce friction with the occlusion device and allow improved removal of the balloon with less frictional force. The balloon can also be formed from a noncompliant or semicompliant material although such balloons will often not refold and could cause friction against the occlusion device.

The stent-like structure or stent for the balloon expandable embodiments can be formed from a plastically deformable metal such as stainless steel, titanium, or other metal or alloy used in coronary and peripheral vascular stenting that can be deformed into the undulations found in the perivalvular channel. The stent can be formed using standard laser cutting technology into a metal tubing of stainless steel or via a wire structure that forms the stent. The stent design can be similar to stent designs used in the coronary or peripheral stent applications. Alternately, the stent design can have a hinge and strut structure that allows for ease of bending at the bending sites or hinges and a larger width for the struts that makes contact with the surface of the balloon such that an elastomeric balloon can push out the stent into the oval shaped channel and push both the hinges and struts into the undulations of the channel without causing excessive local deformation of the balloon. It is anticipated that the stent would deform into the undulations via a low balloon pressure of approximately 1-2 atm. (range 0.5-6 atm.). In a further alternate structure for the stent, the hinges can be enlarged in their radial dimension such that they bend easily during expansion deformation of the stent but the hinges do not bend easily in the radial direction, the struts of this structure are able to extend and bend into the undulations of the channel where the balloon expandable hinges provide the hold the struts into the expanded diameter configuration for the stent.

An additional embodiment for a BE occlusion device provides a balloon located at the end of a catheter shaft that serves both as an inflation balloon and as a closed covering that block blood flow. In this embodiment the balloon has a stent located along a portion or all of the outer surface of the balloon and the distal end of the balloon occlusion device forms a closed covering or blocking fabric located at the distal end. This embodiment is not an over the wire system and hence is delivered to the site of the perivalvular leak channel through an outer sheath. Once the balloon has reached the channel, it is inflated to expand the balloon and stent into the undulations of the channel. The balloon is then detached from the shaft of the catheter via a screw-and-thread-type of attachment or via other attachment and detachment mechanisms. The balloon can be inflated with saline which can be allowed to escape following expansion of the stent into the channel undulations. Alternately, a small duck-bill valve or flapper valve can be located near the proximal end of the balloon in order to retain pressure and retain the fluid contained in the balloon. If a valve is present in the balloon, then a polymer such as a polyurethane or epoxy, for example, can be used to fill the balloon and form a cured polymer with a retained polymer shape within the balloon. Other occlusion systems are described that allow an over-the-wire delivery of a BE occlusion device wherein the balloon is released from the catheter shaft forming both the inflation balloon and the closed covering.

A self-expanding (SE) embodiment for the occlusion device of the present invention includes a SE stent with a covering that covers all or a portion of the stent; the covering is a closed covering or blocking fabric at the distal end, proximal end, or at a location between the proximal and distal end to form blockage for blood flow through the occlusion device. The occlusion device is delivered to the site of the perivalvular leak within an outer sheath that holds the occlusion device in a small diameter configuration. In one embodiment the closed covering or blocking fabric is located at the distal end of the occlusion device and has a guidewire tubing extending through the closed covering. The closed covering has a structure such as a flapper valve or it can be formed from a material that has elastomeric character that allows the covering to close once the occlusion device has been released from the sheath into the perivalvular leak channel and the guidewire tubing has been removed. The SE stent is designed to expand into the undulations found in the oval-shaped perivalvular leak channel.

Another embodiment for the SE occlusion device provides a covering located over all or a portion of a SE stent without the presence of a guidewire tubing. The stent is delivered to the site of the channel within a sheath which holds the SE stent into a small diameter configuration. Upon release from the outer sheath, the SE stent expands into contact with the undulations of the perivalvular leak channel.

The stent structure for the SE occlusion device can be any SE stent structure found in coronary or peripheral medical device use. The material can be an elastomeric metal such as Nitinol (NiTi), Elgiloy, or other elastomeric metal or material including stainless steel and elastic polymers which can behave elastically if deformed locally to small relative deformations in comparison to its thickness.

In one embodiment for the SE stent, the stent is made up of hinges and struts that have a specific geometry; the hinges are formed with a greater thickness in the radial dimension in order to provide a greater outward force in a circumferential direction during expansion deformation. The hinges do not bend in the circumferential direction. The greater outward force ensures that the stent is fully deployed to a large diameter configuration and extend into the far reaching undulation and extent of the oval or crescent-shaped cross section of the perivalvular leak channel. All of the outward expansion forces for the stent are provided by the hinges. The struts are formed such that they have a width in the plane of the cylindrically-shaped nondeployed stent that is large in comparison to the width of the hinges; thus the hinges cause the struts to extend outwards to achieve a large diameter for the expanded stent without bending of the struts in a circumferential direction or in the direction of the hinge expansion deformation. The struts are thin in the radial direction in comparison to the radial dimension of the hinges such that the struts can bend easily in the radial direction and fill in the undulations and sharp radii of curvature found in the channel. The struts can be formed from a SE material or can be softened to form a plastically deformable material that can more easily bend into the undulations of the channels. Also, the struts can be formed from an elastic material that is thin in the radial dimension (in comparison to the hinge radial dimension) and can bend easily into the undulations associated with the channel cavities and protrusions. All of the bending of the stent in the circumferential direction around the small radius of curvature bends of the channel are provided by the struts. The struts do not contribute to the outward expansion forces of the stent.

The struts can also be formed such that they have a crown located along a width of a strut. The crown will allow the strut to bend more easily in a direction toward the concave side, toward the outside of the perivalvular leak channel. Placement of the crown towards the outside surface of the stent will allow the strut to bend more easily into the undulations and fill into the small radii of curvature bends located at the major axis of the oval-shaped cross section of the channel and not collapse toward the inner lumen of the stent. Other embodiments are presented to allow the strut to bend outwards more easily than inwards thereby providing a structure that is held tightly against the surface of the channel without collapsing toward the center of the channel and leaving a channel for blood flow still remaining.

The SE stent structure can have either a cylindrical shape or an indented shape in its nondeployed configuration and expand outwards upon release from the sheath to form a further indented shape that blocks blood flow through the central lumen of the stent. Such a shape can be formed from thermal methods into a NiTi stent structure. Alternately, the stent can be formed with metal struts or stent elements that extend across the lumen of the stent from one side of the stent to the other side approximately 180 degrees around its perimeter. Such stent elements can be used to hold a covering or blocking fabric or serve via itself as a blocking member or blocking fabric to cause blood flow to be occluded either acutely or over a time period of days or weeks and not allow blood flow to occur through the lumen of the stent.

The SE stent can also be formed with the presence of bulbs at each end of the stent; the bulbs representing a region of the stent having a larger equilibrium diameter in its fully expanded configuration. The presence of such bulbs can allow the stent to be positioned with one bulb on each side of the channel to help assist with prevention of migration of the occlusion device within the channel.

In yet another embodiment for the SE occlusion device, the SE covered stent with a closed covering to block flow through the stent or channel can be placed within a sheath for delivery as described earlier with the additional presence of a dilation balloon contained within the lumen of the stent. The balloon, as described earlier, can be an elastomeric balloon that returns to its original shape following expansion within the occlusion device. This embodiment provides an effective postdilation to the SE stented occlusion device and ensures that the occlusion device is well seated within the channel thereby minimizing likelihood for migration of the occlusion device.

In further yet another embodiment for the SE occlusion device, the SE stent can be contained within a balloon or positioned on the outside of a balloon that is filled with either saline or a curable polymer. The balloon can be formed from a noncompliant or semicompliant material that extends easily to cover the perimeter of the channel. The occlusion device is first released from the sheath and allowed to expand outwards into the channel. The balloon is then inflated with saline or polymer to force the balloon and covering into contact with the undulations of the channel and push the stent into intimate contact with all aspects of the channel. Then the balloon is released via a thread and screw mechanism, for example. A valve can be provided to prevent escape of the polymer or saline following expansion of the balloon.

To obtain an optimal capability for retrievability of an occlusion device a self-expanding (SE) stent can be reversibly reduced in diameter back to its original nonreleased diameter and retracted into the delivery sheath from which it was initially delivered if the device is not positioned properly within the channel. However to ensure that the SE stent is forced into all of the undulations found in the narrow oblong-shaped channel, a balloon is used in one embodiment to force the SE stent outwards beyond its normally desired expansion that is limited by a narrow channel. Thus with the present invention the operator is not required to place two or more of the standard occlusion devices within a channel to effect an occluded channel as is the case with the current standard occlusion devices.

In an embodiment of the present invention a SE stent is positioned over a dilation balloon and is delivered into the channel within an external sheath. The proximal stent region is thermally formed to achieve a larger diameter equilibrium diameter that can fill the entire perimeter and major axis distance of the channel. The distal stent region is formed with a small equilibrium diameter that extends out of the distal end of the channel and is of a smaller diameter such that it will not impinge upon the valve leaflets as with many of the current standard occlusion devices. The distal region of the balloon inflates the distal region of the stent to a large diameter, larger than the channel diameter, to form a positional stop that allows the occlusion device to be easily positioned adjacent to the distal end of the channel; the outer sheath still envelopes the proximal portions of the occlusion device during this positioning step. After the proximal region of the occlusion device is placed into correct position within the channel and the sheath is further removed to expose the stent proximal region to the channel, the proximal stent region is expanded out into the channel undulations via a second inflation of the dilation balloon. Deflation of the balloon allows the distal stent region to assume its small equilibrium diameter and push the distal balloon region down to a small diameter that does not impinge upon valve leaflet function. The stent along with its covering provide an occlusive blocking of blood flow through the channel. The device is fully retrievable back into the external sheath until the occlusion device has been detached from the delivery catheter.

In another embodiment, the stent is formed with a BE proximal region and a SE distal region. The stent is positioned over a dilation balloon and is delivered to the channel via an external sheath. This embodiment differs from the last embodiment in that once the occlusion device is positioned within the channel, and the external sheath is withdrawn from the occlusion device, inflation of the dilation balloon expands a BE proximal stent region (rather than a SE proximal stent region) into the undulations of the channel. This embodiment is not as easily retrievable as the last embodiment which had an entirely SE stent. The present embodiment with the BE proximal stent region is retrievable prior to full dilation of the dilation balloon to higher pressures. The BE stent will deform plastically to the undulation of the channel more thoroughly than a SE stent region and will therefore not embolize out of the channel.

Other embodiments that provide both positioning for the occlusion device along with the ability to reposition the device after it has been deployed are also presented in this patent application.

BRIEF DESCRIPTION OF THE DRAWINGS

FIG. 2A is a longitudinal sectional view of an occlusion device in an non-expanded configuration.

FIG. 2B is a cross-sectional view of an occlusion device.

FIG. 3D is a perspective view of the occlusion device positioned within a channel.

FIG. 3E is a cross-sectional view of a flapper valve.

FIG. 3F is a longitudinal section view of a tapered balloon in an inflated configuration having an occlusion device mounted on its outer surface.

FIG. 4A is a cross-sectional view of an occlusion device with a blocking fabric that forms a closed distal end mounted onto a noninflated dilation balloon.

FIG. 4B is a cross-sectional view of an occlusion device with a blocking fabric that forms a closed distal end mounted onto an inflated dilation balloon.

FIG. 4C is a perspective view of an occlusion device located within a channel that formed a perivalvular leak.

FIG. 4D is a cross-sectional view of an occlusion device with a blocking fabric that forms a closed distal end mounted onto an inflated dilation balloon that has a central wire extending throughout the length of the balloon.

FIG. 5A is a plan view of a hinges and struts from a ring of the stent wall structure of one embodiment of the occlusion device.

FIG. 5B is a flattened view of a portion of the wall structure of the stent that is found in one embodiment of the occlusion device.

FIG. 6A is a perspective view of a hinge an strut wall structure of a balloon expandable stent having a short hinge length and small hinge radial dimension.

FIG. 6B is a perspective view of a hinge an strut wall structure of a balloon expandable stent having a short hinge length and large hinge radial dimension.

FIG. 7D is a plan view of an occlusion device having a slidable seal located at a distal end of the occlusion balloon for passage of a mandrel or guidewire.

FIG. 9A is a perspective view of the occlusion balloon held onto the delivery tube and released from the delivery tube via a screw mechanism.

FIG. 10A is a longitudinal section view of self-expanding occlusion device held in an nondeployed configuration by an external sheath and having a flapper valve to allow passage of a guidewire tube.

FIG. 10B is a longitudinal section view of self-expanding occlusion device held in an nondeployed configuration by an external sheath and having a guidewire tube extending through the blocking fabric.

FIG. 10C is a cross-sectional view of a flapper valve.

FIG. 10D is a longitudinal section view of self-expanding occlusion device in a deployed configuration and having a flapper valve to allow passage of a guidewire tube.

FIG. 11A is a longitudinal section view of a self-expanding occlusion device having blocking fabric over its distal end and held in a nondeployed configuration.

FIG. 11B is a longitudinal section view of a self-expanding occlusion device having blocking fabric over its distal end and released into a deployed configuration.

FIG. 11C is a perspective view of the self-expanding occlusion device located in a channel.

FIG. 12 is a longitudinal section view of an occlusion device having a stent central region with a narrowing to block the stent lumen.

FIG. 14 is a plan view of a stent of the occlusion device showing the wall structure.

FIG. 15A is a perspective view of a hinge and strut wall structure for one embodiment of a self-expanding stent used in the occlusion device.

FIG. 15B is a plan view of a portion of a self-expanding stent wall structure for one embodiment of the occlusion device showing a long hinge length.

FIG. 17A is a longitudinal section view of a stent and covering in a nondeployed configuration.

FIG. 17B is a cross-sectional view of a stent and covering in a nondeployed configuration.

FIG. 17C is a longitudinal section view of a stent in an expanded configuration having a narrowing in the central region of the stent.

FIG. 17D is a cross-sectional view of a stent in an expanded configuration having a narrowing in the central region of the stent.

FIG. 18A is a cross-sectional view through the blocking fabric of a stent and covering in a nondeployed configuration.

FIG. 18B is a longitudinal section view of a stent and covering in a nonexpanded configuration.

FIG. 18C is a cross-sectional view through the blocking fabric of a stent and covering in a deployed configuration.

FIG. 18D is a longitudinal section view of a stent and covering with a narrowing of the stent in the central region.

FIG. 19A is a longitudinal section view of an occlusion device with a self-expanding stent held in a nondeployed configuration by an external sheath.

FIG. 19B is a longitudinal section view of an occlusion device with a self-expanding stent having bulbous ends that has been released from an external sheath.

FIG. 19C is a perspective view of an occlusion device with a bulbous stent that has been implanted in a channel.

FIG. 21E is a perspective view of an occlusion device positioned within a channel after inflation and deflation of the occlusion balloon, the stent having a covering attached along the entire stent surface.

FIG. 23C is a plan view of a cross-section through the stent distal body showing a round stent distal body diameter that is larger than the channel minor distance.

FIG. 23D is a plan view of an occlusion device that has been released from the external sheath and expanded out via the occlusion balloon in free space and the occlusion balloon allowed to deflate to an equilibrium configuration with a covering attached to the surface of the stent central body.

FIG. 23E is a plan view of an occlusion device mounted onto a cylindrically-shaped occlusion balloon in an inflated configuration.

FIG. 23F is a plan view of an occlusion device mounted onto a shaped occlusion balloon having a larger diameter balloon distal body, the occlusion balloon is in an inflated configuration.

FIG. 24A is a perspective view of an occlusion device located within an external sheath in a nonreleased configuration.

FIG. 24B is a perspective view of an occlusion device within a channel, the distal balloon body and distal stent body are located distal to the channel, the stent central body and balloon central body are located within the sheath that is located within the channel.

FIG. 25C is the occlusion device of FIG. 25B having the occlusion balloon being subsequently deflated and having the external sheath retracted proximal to the channel; the occlusion balloon is shown being inflated a second time to expand the central stent body outwards to the channel major axis distance.

FIG. 27A is a perspective view of an occlusion device that is located within an external sheath, the occlusion device has a self-expanding stent located on the outside of a balloon central body, the occlusion balloon has a balloon distal body that is used to position the occlusion device properly within a channel.

FIG. 27B is the occlusion device of FIG. 27A located in a channel and having the balloon distal body inflated to position the occlusion device within the channel.

FIG. 27C is the occlusion device of FIG. 27B after the occlusion balloon has been deflated and the external sheath has been retracted proximal to the channel; the occlusion balloon has been inflated a second time to expand the stent central body into contact with the channel major axis distance.

FIG. 27D is the occlusion device of FIG. 27C after the occlusion balloon has been deflated and the occlusion balloon has been detached from a delivery tube used to inflate the occlusion balloon.

DETAILED DESCRIPTION

Figure 1A:
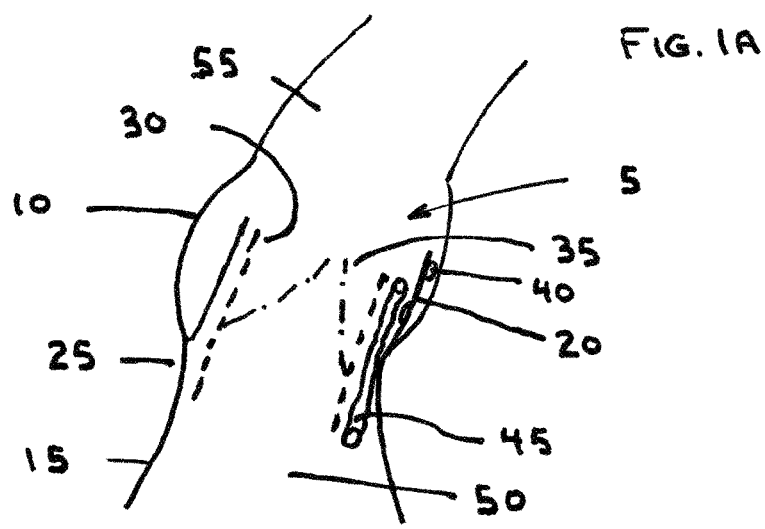
FIG. 1A is a longitudinal sectional view of the aortic root having a TAVR stented device implanted and a longitudinal section of perivalvular leak channel.

FIG. 1A shows the anatomy of the aortic root (5) showing the aortic sinus (10) joined to the left ventricle, LV (15). The native aortic valve leaflets (20) are attached to the annulus (25) and have been pushed to the side via a TAVR stented device (30) that contains TAVR replacement leaflets (35). Calcium nodules (40) located on the back surface of the native leaflets have created a channel (45) that travels between the TAVR stented device and the native leaflets. The channel (45) extends from the aortic sinus past the aortic annulus (25) and into the left ventricular outflow tract, LVOT (50). This channel (45) creates a perivalvular leak that allows retrograde passage of blood from the aorta (55) directly to the LV (15) during diastole.

Figure 1B:
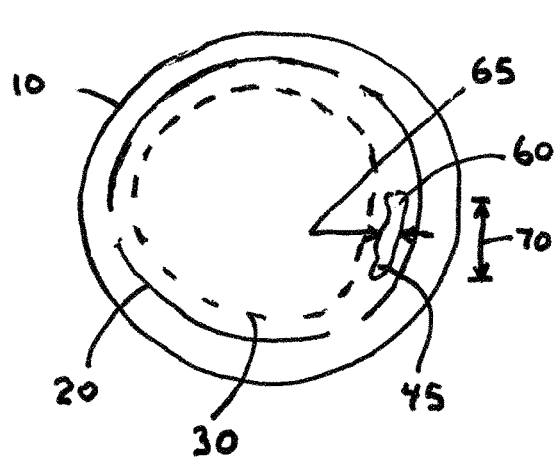
FIG. 1B is a cross-sectional view across the aortic sinus showing a TAVR stented device and a cross-section of the perivalvular channel.
Figure 1C:
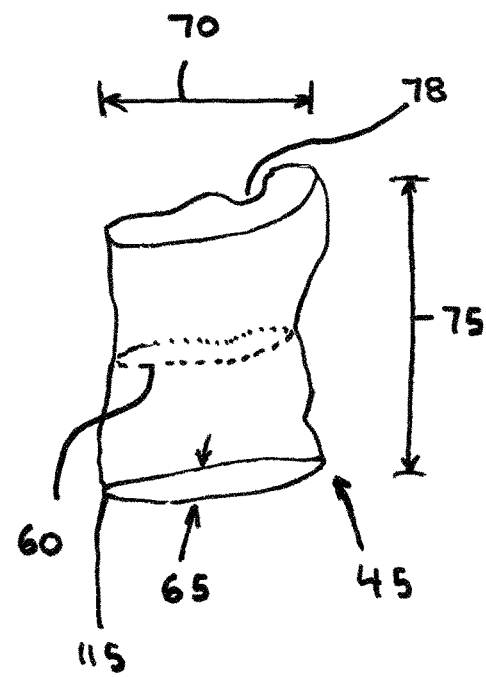
FIG. 1C is a perspective view of a channel that results in a perivalvular leak.

Looking at a cross sectional view of the aortic sinus, as shown in FIG. 1B, one can see that the channel cross-section (60) has an oval or crescent-like shape that extends around a portion of the perimeter of the TAVR device. The channel (45) has a very thin channel minor axis distance (65) ranging from 1 mm-6 mm) and a large channel major axis distance (70) ranging from 2 mm to 25 mm. The axial length (75) of the channel (45) as shown in FIG. 1C ranges from 3 mm to over 15 mm. The channel (45) can have numerous undulations (78) formed from the calcium nodules and from the structure of the TAVR stent. The cross section of the channel (45) along the axial length (75) is also highly variable.

FIGS. 2A and 2B show an overview of specific embodiments of the present invention in a nondeployed smaller diameter configuration. The occlusion device (80) has a cylindrically shaped stent-like structure or stent (85) and a covering (90) that is attached to the stent (85) or is in contact with the entire outer surface (95) of the stent (85) or a portion of the stent (85) surface. The covering (90) can be attached to the stent (85) via a variety of methods including thermal bonding, adhesive bonding, encapsulation of the stent (85) within the covering (90) material, suturing, or other methods. The distal end (130) of the covering (90) (or another portion of the covering (90) located at the proximal end of the stent (85) or central regions (355) of the stent) is a closed covering (100) or blocking fabric (100) such that blood in not able to pass through the covering (90) or at least is highly resistive to blood passage and hence blood flow cannot traverse through the lumen (105) of the stent (85) in an expanded configuration. The closed covering (100) or blocking fabric (100) that extends across the stent cross-section (110) can be contiguous with the covering (90) or it can be a separate fabric element that is joined or attached to the stent (85) or covering (90) using selected bonding methods as described for bonding the covering (90) to the stent. The stent (85) can be a balloon expandable stent (85) formed from a plastically deformable metal, polymer, or composite material; alternately the stent (85) can be a self-expanding stent (85) formed from an elastically deformable material that expands outwards to an equilibrium shape that is larger than the smaller diameter delivery configuration upon release from an external delivery sheath. The covering or blocking fabric (100) for embodiments can be a porous fabric such as expanded polytetrafluoroethylene (ePTFE), a fibrous polymer or tissue material, a woven polymer, a solid polymer film such as polyethylene terephthalate, (PET), nylon, polyurethane, Pebax, or other polymer film materials used in medical devices.

Figure 2D:
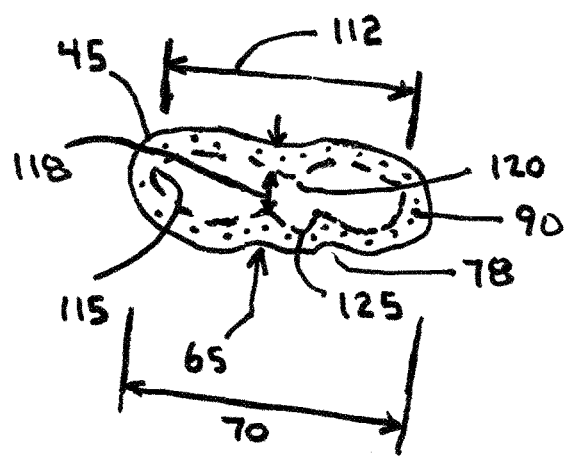
FIG. 2D is a cross-sectional view of a channel that causes a perivalvular leak.
Figure 2E:
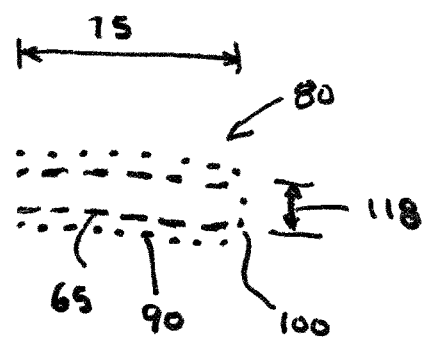
FIG. 2E is a longitudinal sectional view of an occlusion device across its minor axis in an expanded configuration.
Figure 2C:
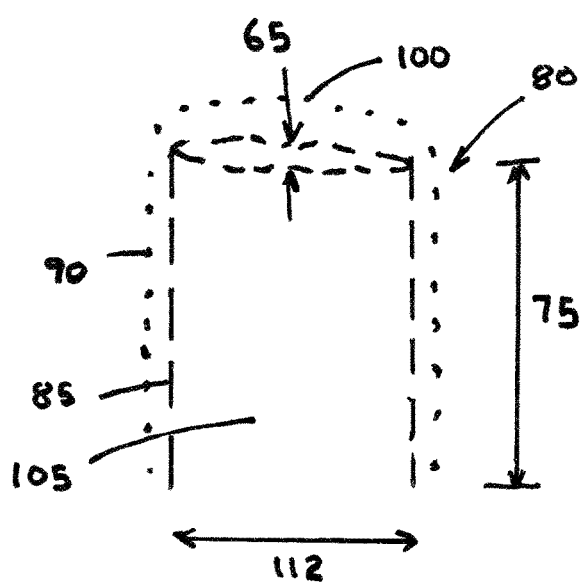
FIG. 2C is a longitudinal sectional view of an occlusion device across its major axis in an expanded configuration.

In an expanded configuration as shown in FIGS. 2C-2E, the stent (85) has enlarged in diameter to form a stent major axis distance (112) that is the same as the major axis distance of the channel (45). The stent (85) and covering (90) has deformed to fill the undulations (78) formed by the calcium nodules found on the native valve leaflets or from the TAVR stent structure and has extended along the major axis distance (112) to fill the small radius of curvature of the channel bend (115) at the ends of the major axis. The stent (85) and cover extend to form an occlusion device (80) that makes contact with protrusions (120) and cavities (125) found along the perivalvular channel (45); the stent minor axis distance (118) is equal to the channel minor axis distance. This general structure for the occlusion device (80) will be further discussed in subsequent embodiments in more detail.

Figure 3C:
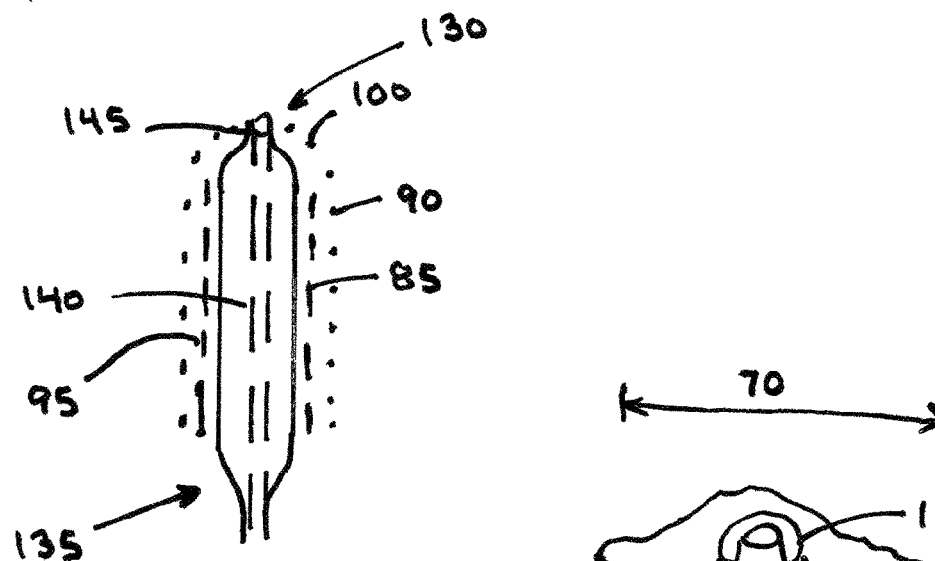
FIG. 3C is a longitudinal section view of an occlusion device mounted onto a dilation balloon in a dilated configuration and having a guidewire tube extending through a flapper valve.
Figure 3B:
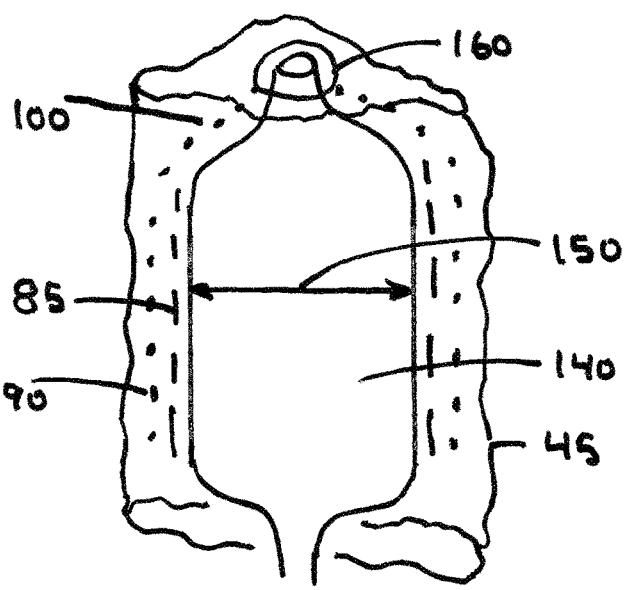
FIG. 3B is a longitudinal section view of an occlusion device mounted onto a dilation balloon in a nondilated configuration and having a guidewire tube extending directly through the blocking fabric.
Figure 3A:
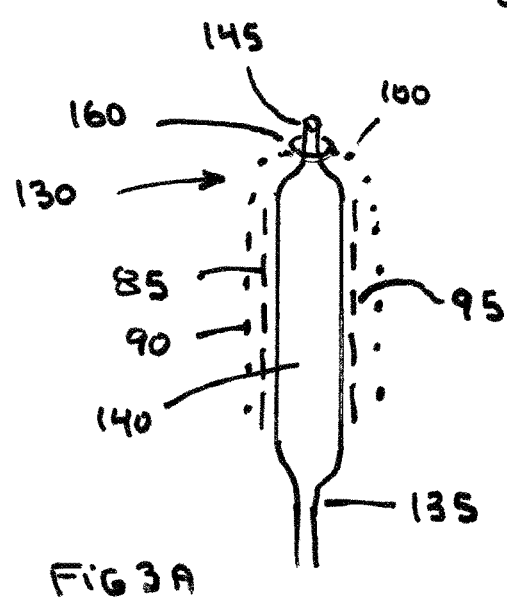
FIG. 3A is a longitudinal section view of an occlusion device mounted onto a dilation balloon in a nondilated configuration and having a guidewire tube extending through a flapper valve.

FIGS. 3A and 3B show an embodiment for a BE occlusion device (80) having a BE stent (85) with a covering (90) positioned along its outer surface (95) and forming a closed covering (100) or blocking fabric (100) at its distal end (130). The BE stent (85) is positioned over a balloon catheter (135) having an expandable balloon (140) located at its distal end (130). A guidewire tube (145) extends through the closed covering (100) to allow passage of the device over a guidewire. The closed covering of FIG. 3B is formed from an elastomeric material such as polyurethane, for example, that closes any opening formed by the guidewire tubing (145) after the balloon has been deflated and withdrawn from the implanted stent. The closed covering can contain a flapper valve (160) as shown in FIG. 3A to provide a closed surface to the closed covering following removal of the inflation balloon. The balloon is formed from an elastomeric material such as polyurethane, silicone, latex, or a composite material that allows return or a majority of return of the expandable balloon (140) to its original diameter following inflation and subsequent deflation of the balloon; alternately, the balloon can be formed from noncompliant or semicompliant materials that are normally used in angioplasty balloons. As shown in FIG. 3C, the balloon is able to reach an inflation diameter (150) that is equal or greater than the channel major axis distance (70). Upon deflation of the balloon, the balloon catheter (135) is withdrawn as shown in FIG. 2D leaving the expanded occlusion device (80) positioned in the channel (45) and making contact with the undulation walls or undulations (78) of the channel (45). A pair of thin silicone or elastomeric flaps (155) can form a flapper valve (160) as shown in FIG. 3E that can be positioned at the distal end (130) of the closed cover or blocking fabric (100) to provide a temporary passage for a guidewire or a guidewire tube (145) that then provides passage for a guidewire; the flapper valve (160) provides for an adequate seal in the closed covering (100) to ensure that blood flow through the occlusion device (80) lumen (105) is blocked. Alternately, fibers having elastic character used in the construction of fibrous elastomeric blocking fabric (100) or closed covering (100) can provide a slidable sealing passageway for the guidewire tubing during delivery of the occlusion device (80) to the channel (45). The balloon of the present invention can be formed with a tapered shape or conical shape forming a tapered balloon (165) with a smaller diameter toward the distal end (130) of the occlusion device (80) as shown in FIG. 3F. Removal of the balloon from the implanted occlusion device (80) will be more easily released and prevent potential migration of the occlusion device (80) in a proximal direction (170) upon removal of the balloon catheter. Other balloons such as noncompliant balloons or semicompliant balloons can also be used to dilate the stent (85) of the occlusion device (80) into contact with the walls of the channel (45); such balloons can form undesirable wings or flattened extensions that can interfere with removal of the balloon catheter (135) if the deflated balloon shape is not adequately controlled.

FIGS. 4A-4D show a BE occlusion device (80) that is not delivered via an over-the-wire (OTW) method of delivery owing to the absence of a guidewire lumen. In this embodiment, the occlusion device (80) is again comprised of a BE stent (85) with a covering (90) attached to either the entire stent (85) or a portion of the stent. The distal end (130) of the covering (90) is a closed covering (100) that does not have any opening for passage of either a guidewire or a guidewire lumen. The occlusion device (80) is positioned onto an expandable balloon (140) located at the distal end of a balloon catheter. To place this balloon across the channel (45), a guidewire is first placed through the channel (45) and then is exchanged for a hollow sheath that allows passage of the occlusion device (80) within its lumen. Following placement of the occlusion device (80) within the channel (45), the balloon is inflated (see FIGS. 4B and 4C) to expand the stent (85) and covering (90) outwards into contact with the walls of the channel (45) and making contact with the undulations (78) of the channel (45). The balloon is then deflated and removed from the occlusion device. The balloon can have a tapered or conical shape as described earlier. The presence of the stent (85) on the outer or inner surface of the covering (90) will provide adequate axial-strength to allow the occlusion device (80) mounted onto an expandable balloon (140) to be pushed across the channel (45) prior to inflation of the balloon. Also, as shown in FIG. 4D, a central wire (175) or support mandrel can be placed, if necessary, from the catheter shaft (180) to the balloon tip to provide additional push-support for pushing the occlusion device (80) across the channel (45).

FIGS. 5A-5B show one embodiment for the stent wall structure (188) for the stent (85) found in a BE embodiment of the present invention. The BE stent (85) has a soft BE hinge (190) that undergoes the bending deformation as the stent (85) is expanded; the hinges are located in the bent regions (195) or hinge regions (195) of the stent structure (188); the hinge (190) deformation allows the stent (85) to be deformed during expansion to a larger diameter as well as being deformed in a radial direction to fill the cavities or form around protrusions that extend into the channel (45). The hinges are joined together by linear elements or struts (200). The material of the stent (85) can be a soft metal including stainless steel, platinum, titanium, and other plastically deformable metals, composites, polymers, and tissue material such as collagen, fibrin, and biodegradable material. The stent structure (188) can be comprised of rings (205) that can have a of a zig zag configuration (208) or zig zag pattern (208), with rings (205) connected via flexible or deformable connectors (210) that provide the stent (85) with axial stability. Other stent structures such as those found in coronary and peripheral vascular stents can also be used to provide the stent (85) or stent-like structure (188) found in the present invention. The struts of the stent (85) can similarly be formed from a plastically deformable material that is able to conform to the undulation within the channel (45). Conformation of the stent (85) to the undulation will provide the occlusion device (80) with the characteristics of avoiding migration of the device out of the channel (45) and also making a tighter seal with the walls of the channel (45) to create an improved blockage for blood flow. The stent structure (188) is generally weaker in some aspects than a stent structure (188) used to support a blood vessel during vascular stenting. The struts and hinges of the BE stent (85) of the present embodiment are thinner (less than 0.003 inch thickness) in the radial dimension (than a vascular stent) in order to allow them to bend more easily into the undulations (78) of the channel (45) under a lower balloon pressure of approximately 1-2 atm. (range 0.5-6 atm.); this lower pressure can be effectively applied by an elastomeric balloon of the present invention; an elastomeric balloon (i.e., formed from silicone, polyurethane, or other elastomeric polymer or composite) is unable to provide the large pressure dilations required by standard angioplasty and vascular stenting balloons.

Figure 6C:
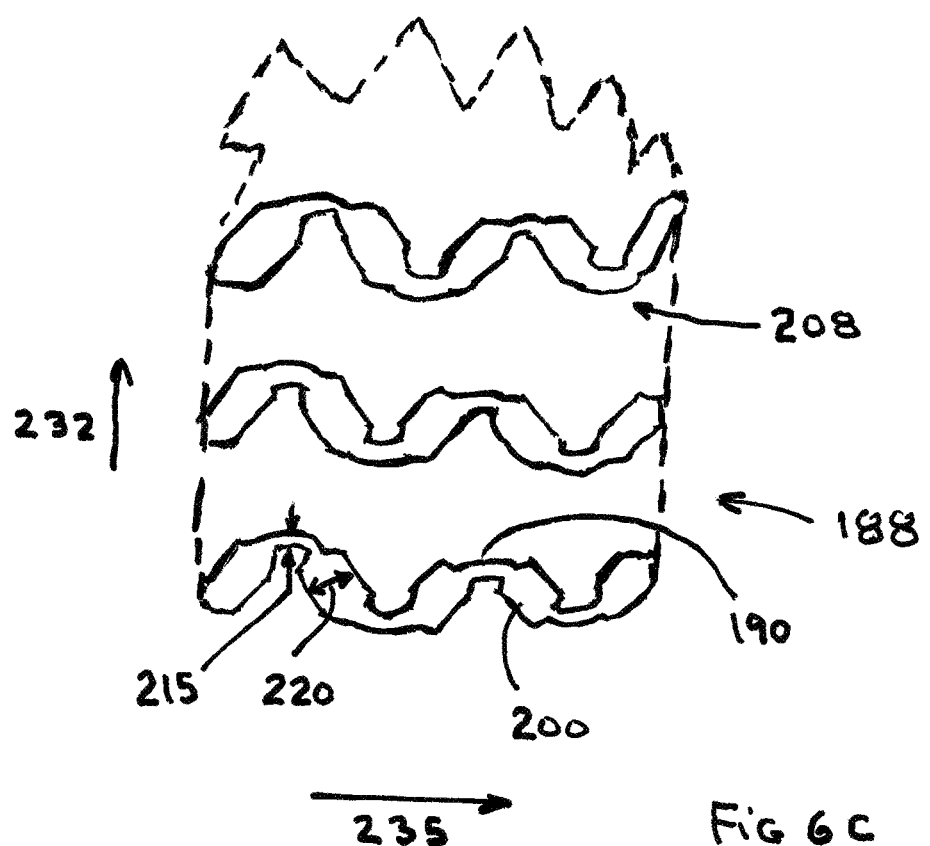
FIG. 6C is a perspective view of a stent having the hinge and stent wall structure of a balloon expandable stent.

Another embodiment for the BE stent (85) of the present invention is found in FIGS. 6A and 6B. In this embodiment for the BE stent (85) the hinge regions (195) are formed such that they are smaller in hinge width (215) than the strut width (220). The stent structure (188) can be formed into a zig zag pattern as shown in FIG. 6C or into any other stent structural pattern used in vascular stents found in the medical device industry. Upon dilating the stent (85) with an expandable balloon (140) such as an elastic balloon, the soft narrow hinges are able to easily deform into the undulations (78) found in the channel (45) both in a circumferential expansion direction as well as a radial direction (218) outwards into channel (45) undulations (78) and around protrusions formed from calcium deposits at generally low pressures of approximately 1-2 atm. The wide strut width (220) allows the elastic balloon to push against the struts to push the struts outwards without significant local deformation of the balloon. The hinge length (222) is short in comparison to the hinge radial dimension (225) so that the expansion deformation will result in plastic deformation of the balloon expandable hinges.

A further embodiment for the BE stent (85) of the present invention is shown in FIGS. 6B and 6C which has hinges having a larger hinge radial dimension (225) extending in the radial direction (218) than the strut radial dimension (230). Several rings (205) of zig zag pattern can be positioned adjacent to each other in an axial direction (232) to form a stent structure (188). During expansion deformation in the circumferential direction (235), the hinges (190) deform plastically but the larger strut widths which are larger than the hinge width (215) are unable to bend in the circumferential direction (235) or the direction of hinge expansion and hence the struts are forced outwards to a larger diameter during balloon expansion; the large strut widths also provide larger area for the elastic balloon to push against without causing local balloon deformation of an elastomeric balloon. The thin strut radial dimension which are thinner than the hinge radial dimension (225) allow the struts to bend into the undulations (78) and make small radius of curvature bends located at the ends of the major axis of the channel (45). Thus expansion of this stent structure (188) (see FIGS. 6B to 6C) allows improved apposition of the stent (85) and the covering (90) attached to the outer surface (95) of the stent structure (188) with the undulations (78) in the channel (45).

The struts (200) of the stent (85) can be formed from with elastic character even if the hinges are formed from material with plastically deformable character. The struts (200) can be formed from an elastic material such as Nitinol (NiTi), for example, or alternately can be formed with a very thin radial dimension (i.e., less than 0.003 inches) out of a stainless steel, cobalt chrome, or other metal or alloy that would normally behave in a plastically deformable manner. The hinges (190) can be formed from the same material as the struts and perform with a balloon expandable or plastically deformable character. Hinges (190) that are formed from stainless steel, cobalt chrome, or other plastically deformable material will perform in a balloon expandable manner. Alternately, the use of Nitinol or other elastic material normally used in self-expanding stents can be used for the hinges (190) so long as the hinge length (222) is short in comparison to the hinge radial dimension (225) thereby causing the hinge to become plastically deformed during the expansion deformation of the stent (80). The Nitinol or elastically deformable material used in the stent can also be thermally treated locally to cause the hinge to become plastically deformable and the struts (200) to remain elastically deformable.

Figure 7A:
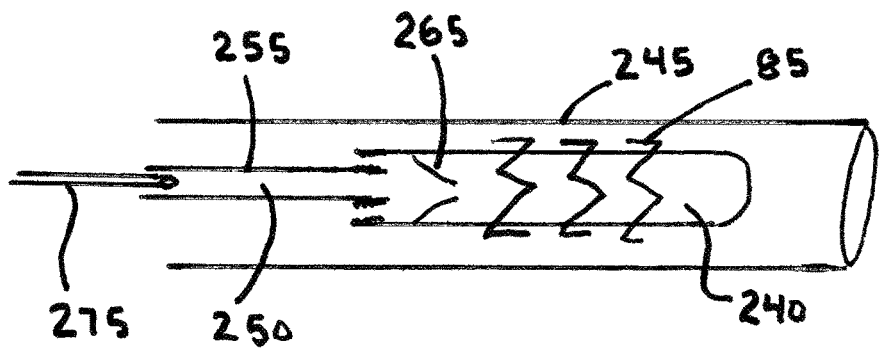
FIG. 7A is a plan view of a balloon expandable occlusion device in an nondeployed configuration delivered by an external sheath.
Figure 7B:
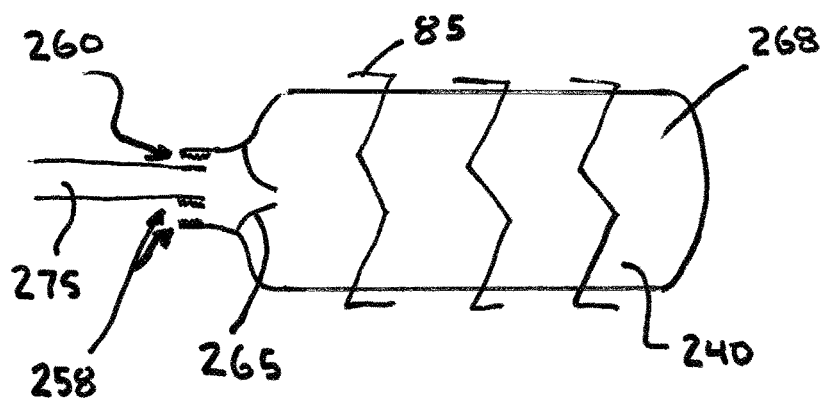
FIG. 7B is a plan view of a balloon expandable occlusion device inflated to an inflated volume with inflation medium that is delivered from the delivery tube.
Figure 7C:
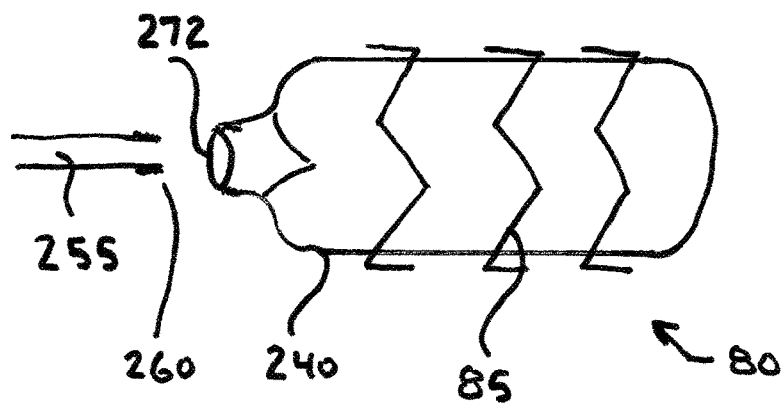
FIG. 7C is a plan view of a balloon expandable occlusion device inflated with inflation medium and released from the delivery tube.

Yet another embodiment for the BE occlusion device (80) of the present invention is shown in FIGS. 7A-7C. In this embodiment an occlusion balloon (240) that is used to inflate the stent (85) serves additionally as the covering (90) and blocking fabric (100). The occlusion balloon (240) serves as a blocking fabric (100) that prevents blood flow through the lumen (105) of the stent (85) and through the channel (45). The occlusion balloon (240) which serves as the covering (90) and blocking member for this embodiment is formed from an elastic material such as silicone or polyurethane, for example, can be used to form the occlusion balloon (240) and also serve as the covering (90)

material and blocking fabric (100). The elastic material for the occlusion balloon has an area strain capability of at least 200% (range 200-500%) in order to push the stent outwards during balloon inflation into the undulations found in the channel.

Alternately, a noncompliant or minimally compliant balloon material (i.e., less than 5% difference in diameter over the pressure range of the balloon during inflation) such as PET, some low compliance nylons, and other polymer materials used in low or non-compliant balloons can be used. Such noncompliant balloons will require unfolding as they are inflated into the narrow channel; a lubricious balloon material such as polyethylene, Nylon, Pebax, and other materials can provide this unfolding characteristic. Other occlusion balloon materials that undergo some plastic deformation that is retained such as some plastically deformable Pebax films and polyolefin films can also be used to form the occlusion balloon (240) which also serves as the and covering (90) material. The BE stent (85) can be attached to the balloon on the outside or inside surface of the balloon or it can be placed into contact with the outside surface of the balloon. In this embodiment the balloon and stent (85) are placed across the channel (45) through an external sheath (245). After removal of the sheath, the balloon is inflated via an inflation lumen (250) of a delivery tube (255) with either saline or a curable polymer such as a polyurethane, epoxy, or other curable polymer material as shown in FIG. 7B. The occlusion balloon (240) is held to the delivery tube (255) via the holding assembly (258) thereby allowing the occlusion balloon to be filled with inflation fluid via the delivery tube. After delivery of the inflation medium, the balloon is detached from the shaft of the delivery tube (255) via a holding assembly (258) such as a screw and thread mechanism (260), for example, as shown in FIG. 7C or other attachment and detachment mechanism. One element such as a threaded surface, for example, of a thread and screw holding assembly (258) is located on the occlusion balloon and the other element is located on the delivery tube (255). A duckbill valve or check valve (265) located at the proximal end (270) of the occlusion balloon (240) can be used to prevent backflow of polymer or saline out of the balloon following delivery of the occlusion device.

For the case that saline alone is used to inflate the balloon, the check valve for an embodiment can be omitted and the saline inflation fluid or dilute contrast medium inflation fluid allowed to drain out of an open orifice (272) of the occlusion balloon (240) following inflation of the occlusion balloon and detachment of the delivery catheter (255) from the occlusion balloon (240). The inflation volume of inflation medium used to inflate the occlusion balloon to its inflated volume (268) as shown in FIG. 7B can freely flow out of the occlusion balloon (240) through the open orifice (272). The advantages associated with using saline or saline-based inflation fluid (rather than a curable liquid to solid polymeric material) are: a lower occlusion balloon (240) profile due to omission of the check valve, and ease of use due to allowance for leakage of saline (as opposed to a major concern for leakage of a liquid polymer) into the blood stream during balloon inflation and following balloon detachment. A hollow mandrel or hollow tube (275) can be placed within the inflation lumen of the delivery tube (255) and across the check valve, if necessary, to drain the saline inflation medium out of the balloon in the presence of the check valve (265).

As shown in FIG. 7D the occlusion balloon (240) can be formed such that a slidable seal (325) is located in the distal end of the occlusion balloon (240). The slidable seal allows passage of a guidewire (330) or a mandrel through the slidable seal such that inflation fluid cannot pass between the slidable seal and the guidewire during inflation of the occlusion balloon (240). When saline or saline-base contrast medium is used to inflate the occlusion balloon, leakage of inflation fluid is tolerated past the seal and into the blood stream during balloon inflation. The stent (85) can still be properly deployed even though the slidable seal does not provide a perfect seal without leakage of inflation fluid. If a curable polymer is used to inflate the occlusion balloon, the slidable seal cannot allow leakage of the polymeric inflation fluid. The slidable seal provides the occlusion device with the capability of being delivered to the site within the channel over a guidewire.

Figure 8A:
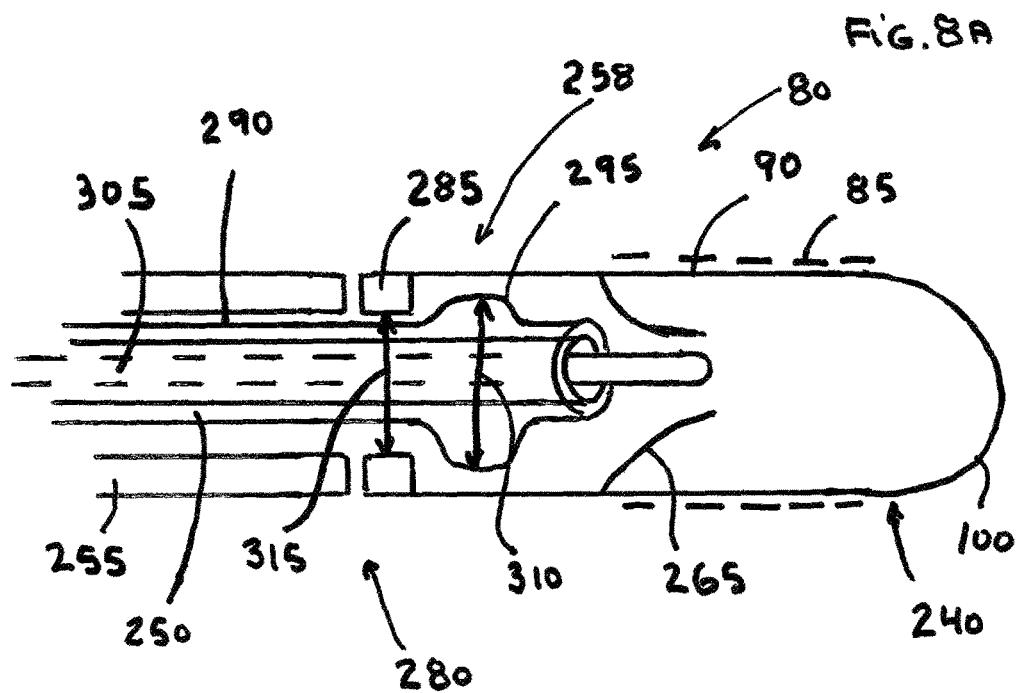
FIG. 8A is a balloon expandable occlusion device that is held during inflation via a delivery catheter having a mandrel.
Figure 8B:
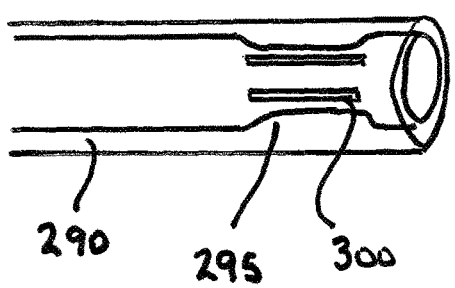
FIG. 8B is a perspective view of a hollow member used to hold the occlusion balloon relative to the delivery catheter during inflation of the occlusion balloon.
Figure 8C:
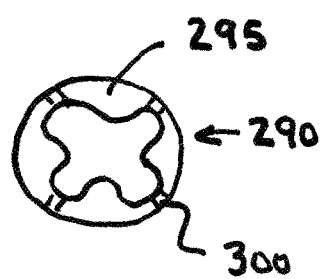
FIG. 8C is a cross-sectional view of the hollow member showing the member stop and slits.

FIGS. 8A-8F show another holding assembly (258) to allow both attachment for filling and provide detachment of a BE occlusion device (80) from the delivery tube (255) wherein the occlusion balloon (240) is serving also as the covering (90) and blocking fabric (100) for the occlusion device. The occlusion balloon (240) which is detachable from the delivery tube (255) is located at the distal end (280) of the delivery tube (255). The occlusion balloon (240) is formed from a material similar to that described in the embodiment of FIGS. 7A-7C. The occlusion balloon (240) has a balloon stop (285) or narrowed diameter region at its proximal end (270) which serves as one element of the holding assembly (258). Another element of the holding assembly (258) comprises a hollow member (290) that has four member stops (295) that extend through the delivery catheter or delivery tube (255) and across the balloon stop. The hollow member has four slits (300) that are located in an axial direction (232) between each of the member stops (295) as shown in FIGS. 8B and 8C.

Figure 8D:
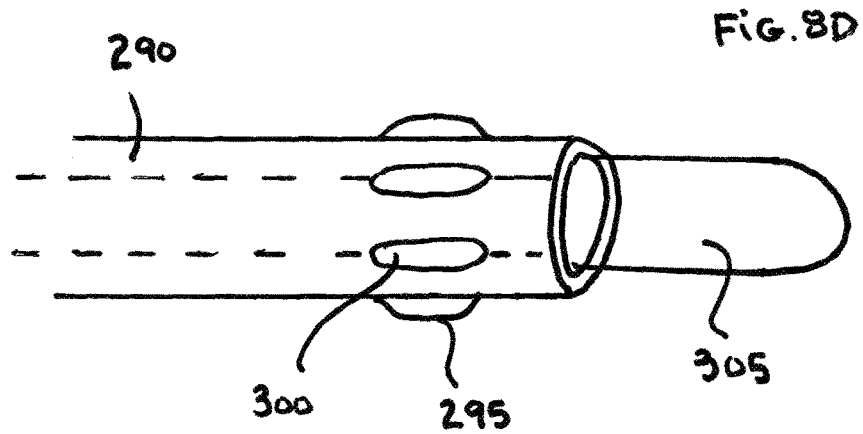
FIG. 8D is a perspective view of the hollow member that holds the occlusion balloon against the delivery catheter and also releases the occlusion balloon.
Figure 8E:
FIG. 8E is a cross-sectional view of the mandrel.

Insertion of a mandrel (305) within the hollow member causes the member stops (295) to extend outwards to form a member stop diameter (310) that is larger than the balloon stop diameter (315) as shown in FIGS. 8D and 8E. Gentle tension placed on the hollow member will hold the occlusion balloon (240) into contact with the delivery tube (255) as long as the mandrel (305) is contained within the hollow member. Inflation of the occlusion balloon (240) can then occur via the hollow member when the occlusion balloon (240) is positioned within the channel (45). Inflation medium can enter the balloon via spacing between the hollow member and the mandrel (305). Inflation of the occlusion balloon (240) causes the stent (85) and the occlusion balloon (240) to come into intimate contact with the channel (45) wall and filling in the undulations (78) in the channel (45). After the balloon has been inflated with either saline or polymer the mandrel (305) can be withdrawn thereby allowing the member stop diameter (310) to become smaller than the balloon stop diameter (315). The hollow member can then be withdrawn leaving the inflated balloon contained within the channel (45). A duckbill valve or check valve can be used to prevent the polymer or saline solution from exiting the proximal end (270) of the balloon.

Figure 8F:
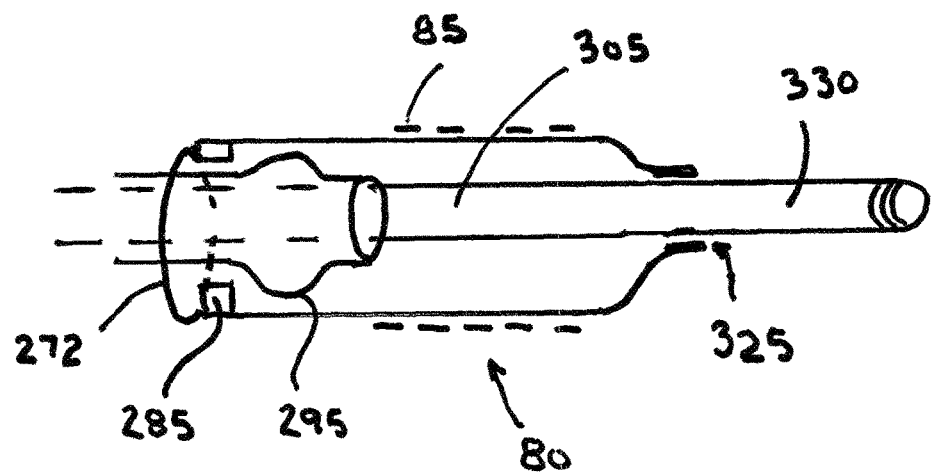
FIG. 8F is a longitudinal sectional view of an occlusion device having a guidewire passing through a slidable seal.

The check valve can be omitted if saline or dilute contrast is used to inflate the occlusion balloon; the saline being allowed to freely flow out of the occlusion balloon (240) after implant; for this embodiment the occlusion balloon proximal end (270) has an open orifice (272) that allows free flow of saline or saline-based inflation medium from the inside of occlusion balloon to flow out of the occlusion balloon when detached from the delivery tube (255). All of the inflation fluid volume used to inflate the occlusion balloon to its fully expanded dimensions within the channel is free to flow out of the occlusion balloon through the open orifice (272) when the occlusion balloon is detached from the delivery tube (255). Use of saline inflation medium without a check valve provides advantages of a lower profile occlusion balloon due to omission of the check valve and allow leakage of saline both during inflation of the balloon and after detachment of the balloon without negative consequences to the patient. This embodiment can be delivered to the channel (45) via an external sheath as described for the previous embodiment. Alternately, the occlusion balloon (240) can be modified as shown in FIG. 8F such that a guidewire serves to guide the occlusion device (80) across the channel (45) as well as serve as the mandrel (305). A sliding seal can be located on the blocking fabric (100) to allow passage of the guidewire (330) while blocking flow of inflation medium out of the sliding seal during inflation of the occlusion balloon (240). The occlusion balloon is shown in FIG. 8F without the check valve such that the inflation fluid such as saline, for example, can freely flow out of the open orifice (272) into the blood stream following detachment of the occlusion balloon (240) from the delivery tube (255).

A further embodiment of a BE occlusion device (80) is shown in FIG. 9A. This embodiment provides an OTW BE occlusion device (80) wherein the occlusion balloon (240) serves as the covering (90) and the blocking fabric (100), and the occlusion balloon (240) is detachable from the delivery tube (255) or delivery catheter. The occlusion balloon (240) has a hollow guidewire shaft (320) that provides passage for the guidewire (330) therethrough. The guidewire tubing or guidewire shaft (320) of this embodiment forms a slidable seal (325) with a guidewire (330) at the distal end (130) of the occlusion balloon. The slidable seal (325) is a narrowed region of the guidewire shaft (320) or flapper valve or other sealing mechanism that prevents significant leakage or completely blocks leakage of inflation medium between the guidewire (330) and the guidewire shaft (320) when the occlusion balloon (240) is being inflated. The slidable seal (325) can be designed to allow, for example, up to 50 ml of saline-based inflation fluid to leak through the slidable seal (325) during a single inflation of the occlusion balloon and be well tolerated by the patient. If saline inflation medium is used to inflate the balloon (rather than a contrast medium) of this embodiment, a greater amount of leakage of saline can be tolerated around the slidable seal (325) during balloon inflation. The saline inflation medium enters the balloon through an inflation hole (335) found in the guidewire shaft (320). The saline inflation medium causes the occlusion balloon (240) and the stent (85) to expand into contact with the channel (45) making intimate contact with the undulations. Following inflation, the balloon is detached from the delivery tube (255) via a thread and screw mechanism or other holding assembly (258). The mechanism or attachment and detachment of the balloon can alternately be similar to the hollow tube and mandrel (305) mechanism described in the embodiment of FIGS. 8A-8E.

FIGS. 10A-10D show an embodiment of a SE occlusion device (80) of the present invention. The SE stent (85) has a covering (90) attached to its outer or inner surface. The covering (90) extends around the distal end (130) of the occlusion device (80) forming a closed cover or blocking fabric (100) that prevents blood flow from flowing through the central lumen (105) of the occlusion device. A flapper valve (160) as shown in FIG. 10C can be located at the distal end (130) of the closed covering (100) or blocking fabric (100) to allow temporary passage of a guidewire shaft (320) through the closed cover during delivery of the occlusion device (80) across the channel (45). The SE stent (85) is held via an outer or external sheath (245) into a small diameter configuration during delivery of the occlusion device (80) across the channel (45). A pusher member (345) is located within the outer sheath proximal to the occlusion device (80) to allow extraction of the sheath while maintaining positioning of the occlusion device (80) within the channel (45). Removal of the sheath allows the SE stent (85) and its attached cover to expand outwards into the channel (45) and into the undulations (78) of the channel (45). The guidewire shaft (320) along with the guidewire (330) can be removed either prior to or following release of the occlusion device (80) within the channel (45). The stent (85) is designed to extend to a stent diameter or stent major axis distance (112) that is at least equivalent to the channel major axis distance (65) as shown in FIG. 10D.

The self-expanding stent wall structure (188) is formed from an elastic metal such as Nitinol, Elgiloy, or other metal with elastic or memory character. The configuration for the stent wall structure (188) can have similar zig zag pattern (208) and can contain hinge (190) and strut (200) configurations similar to those described for the balloon expandable wall structure (188). The hinge length (222) for the self-expanding stent wall structure (188) is longer than the hinge width (215) to provide the self-expanding hinge (190) with elastic bending without exceeding an elastic limit during expansion deformation.

An alternate embodiment of the self-expanding (SE) occlusion device (80) is shown in FIGS. 11A-11C. In this embodiment the occlusion device (80) is not delivered over a guidewire (330) but instead is delivered through an external sheath. The SE stent (85) has a covering (90) that extends along the entire stent surface or a portion of the stent inner or outer surface (95) and forms a closed covering (100) or blocking fabric (100) at the distal end (130) as shown in FIGS. 11A and 11B. The blocking fabric (100) can alternately be located at the proximal end (270) or in the central regions (355) of the stent. In a manner similar to that described in the embodiment of FIGS. 10A-10D the SE occlusion device (80) is delivered to the channel (45) via a release from an external sheath and allowed to expand into contact with the channel (45) as shown in FIG. 11C. The stent wall structure (188) allows the stent (85) to easily bend into the undulations (78) of the channel (45) and make intimate contact with the channel (45) wall and thereby both prevent blood flow but also reduce the likelihood for migration of the occlusion device.

As shown in FIG. 12, the SE stent (85) can be formed into a shape that has a narrowing located somewhere in the stent central region (355) between the proximal end (270) and distal end (130) of the stent, or alternately, the narrowing of the stent (85) can be located at the proximal end (270) or distal end (130) of the stent. Upon release from the external sheath as shown in FIG. 12, the stent (85) expands outwards in some regions and remains at a smaller diameter configuration in other regions to ensure blockage of blood flow through the lumen (105) of the occlusion device (80) and hence through the channel (45). The covering (90) not only serves to prevent blood from flowing through the interstices of the stent wall structure (188), the covering (90) also serves as a blocking fabric (100) to block blood flow through the cross section of the stent lumen (105).

The wall structure (188) of the SE stent (85) of the SE occlusion device (80) of the present invention is such that the stent major axis distance (112) should expand outwards to meet the full dimension of the channel major axis distance

Figure 13A:
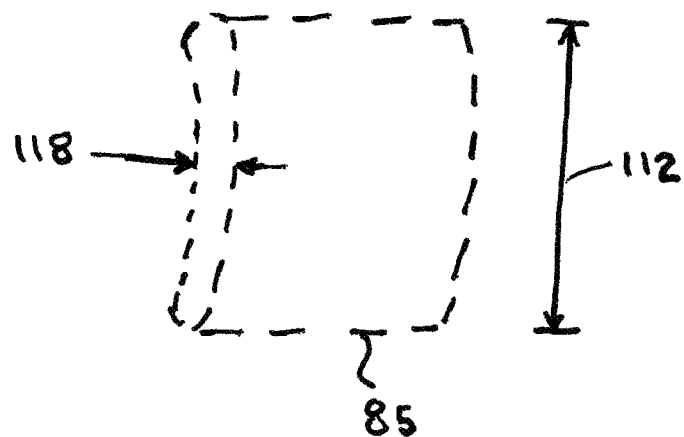
FIG. 13A is a perspective view of the stent found in the occlusion device showing the stent major axis and stent minor axis.
Figure 13B:
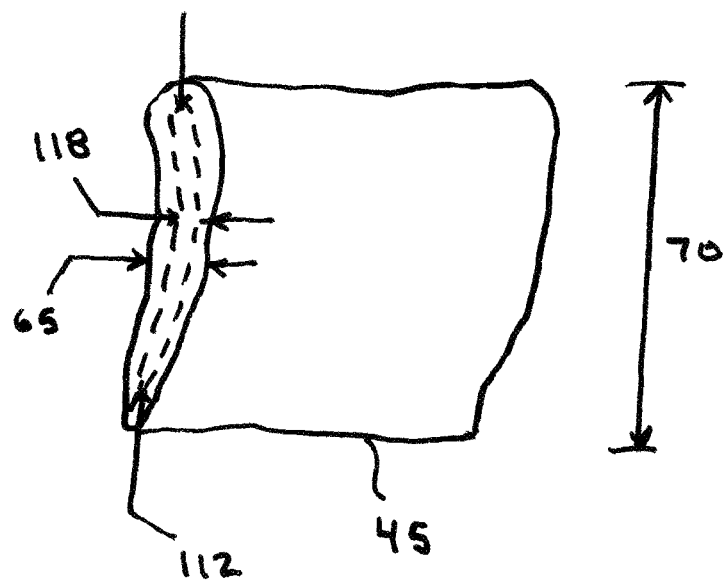
FIG. 13B is a perspective view of the stent and occlusion device positioned within a channel.

(65) as shown in FIGS. 13A and 13B even though a neighboring portion of the stent (85) such as the stent minor axis distance (118) is being held at a smaller diameter that is equal to the channel minor axis distance (65).

The SE stent (85) of the SE occlusion device (80) can be formed from SE hinges and SE struts using a stent structure (188) that is similar to other SE stents used for coronary and peripheral vascular stenting. One embodiment for the stent structure (188) provides a zig zag wall structure for the stent (85) with rings (205) formed from an elastomeric metal such as Nitinol (NiTi), Elgiloy, other elastomeric forms of stainless steel, composites, or elastomeric polymers as shown in FIG. 14; other stent wall structures found in vascular stents can also be used for the SE stent of the present invention. The individual zig zag rings (205) can be connected together in an axial direction (232) via connectors (210). The elastic outward force in the radial direction (218) provided by the hinges must be great enough to cause the struts to bend to a small radius of curvature in the radial direction (218) and deform into the undulations (78) in the channel (45).

Another embodiment for the SE stent structure (188) for the SE occlusion device (80) is shown in FIGS. 15A and 15B. In this embodiment the SE stent structure is formed having SE hinges that have a larger hinge radial dimension (225) than the strut radial dimension (230). The hinge radial dimension (225) must be much greater than the strut radial dimension (230) to generate the large elastic expansion force; the strut radial dimension (230) must be thinner (dimension is less than 0.003 inches) than even a normal vascular stent in order to deform to a very small radius of curvature as found at the ends of the major axis of the channel (45). This large hinge radial dimension (225) is intended to provide a larger radial outward force to expand the stent (85) into the undulations (78) of the channel (45) and reach to a stent major axis distance (112) that is equal to the channel major axis distance. The struts have a large strut width (220) that causes them to not bend in the in the direction that the hinges are bending as the hinges open during expansion deformation (circumferential direction). The struts have a very thin strut radial dimension (230) that allows them to bend in the radial direction and bend into the small radius of curvature bends located at each end of the channel major axis. The hinge length (222) is long in comparison to the hinge width (215) such that the hinge (190) does not undergo plastic deformation during expansion deformation and retains its self-expanding elastic character.

Figure 16A:
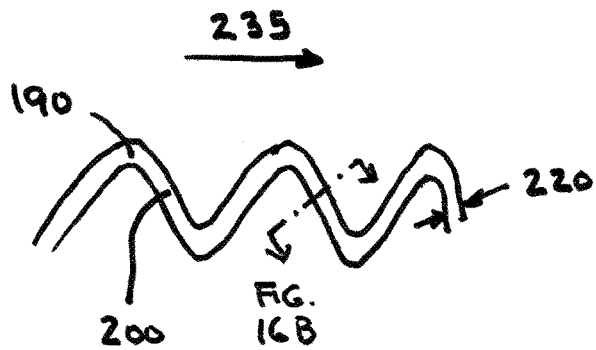
FIG. 16A is a plan view of a zig zag wall structure from a portion of the stent for one embodiment of the occlusion device.
Figure 16B:
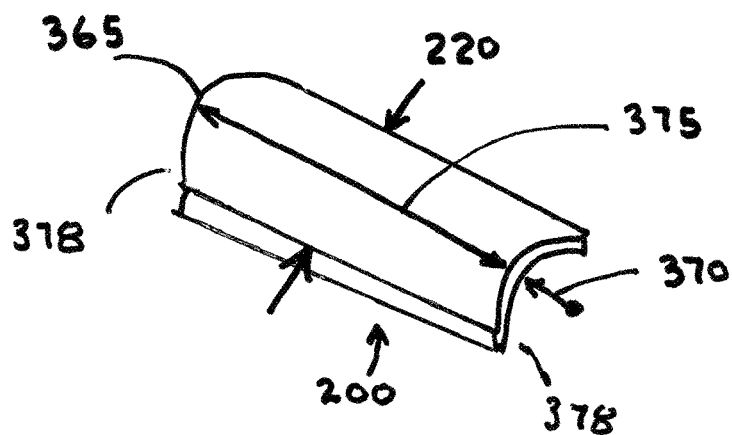
FIG. 16B is a perspective view that shows a stent strut that has a crown in the direction of the stent width.

As the struts are forced to open up during expansion deformation, it is important that they bend with a curvature that favors bending into the small radius of curvature bends located at each end of the major axis of the channel and not bend inwards via a buckling or collapsing mechanism into the lumen (105) of the stent. The stent struts for either the self-expanding or balloon expandable stent wall structures can be formed with a crown in the direction of the strut width (220) and having a strut width radius of curvature (370) along the strut width (220) as shown in FIGS. 16A-16C. This strut (200) will preferentially bend outwards along the strut length (375) from one strut end (378) to the other strut end (378) to fill the cavities and undulations (78) found in the channel (45) and will bend easily to a strut length radius of curvature (380) around a small radius of curvature channel bend (115) located at the ends of the major axis of the channel (45).

Figure 16D:
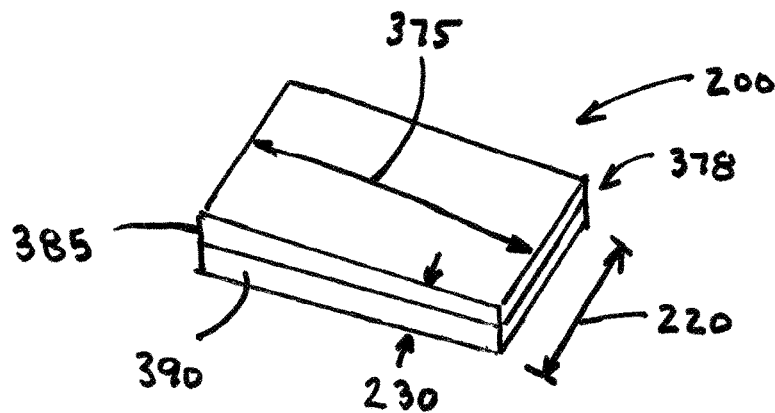
FIG. 16D is a perspective view of a stent strut that has two layers of material forming its strut thickness or radial dimension.
Figure 16C:
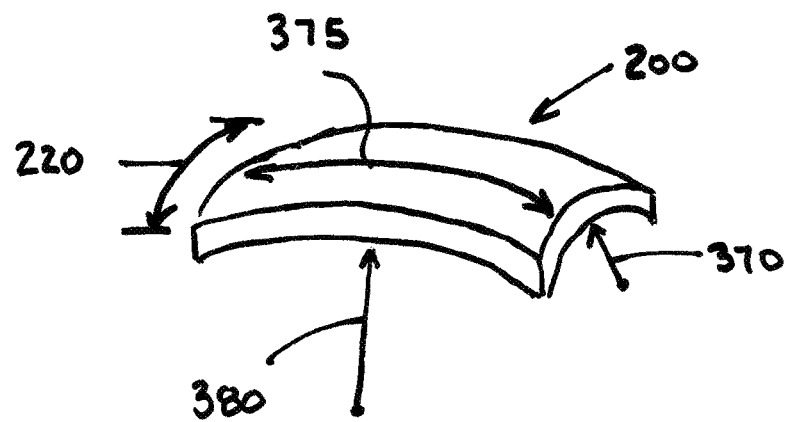
FIG. 16C is a perspective view of a stent strut that has a crown in the direction of the stent width and a crown in the direction of the stent length.
Figure 16E:
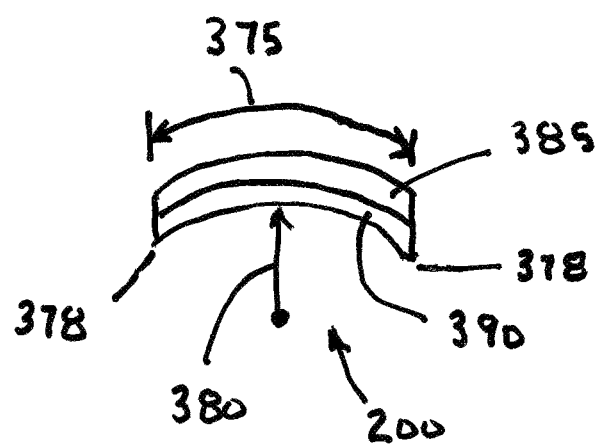
FIG. 16E is a plan view of a strut formed from two materials in the radial direction and bending along the strut length.

An alternate design for a strut (200) is shown in FIGS. 16D and 16E; in this embodiment for the SE strut (200) two different metals or materials are used for forming two layers for the strut. The top layer is formed from a softened metal having a low modulus and the lower layer is formed from a metal with a high modulus. The strut (200) is then able to more easily bend to form a small strut length radius of curvature (380) bend to fill in the small radius of curvature bend located along the strut length (375) or strut width. The soft top layer is better able to stretch than the hard bottom layer; neither layer is able to provide significant compressive strain.

The SE stent (85) of the SE occlusion device (80) can be formed such that it is cylindrical cross-sectional shape in its small diameter configuration (see FIGS. 17A and 17B) and expands out to form a shape that has an equilibrium shape that has a occluding portion (395) of the stent (85) extending into the lumen (105) region of the stent (85) (see FIGS. 17C and 17D). The presence of a covering (90) on the stent (85) surface will then act as a blocking fabric (100) to prevent blood flow through the stent lumen (105) and block blood flow through the channel (45) as shown in FIGS. 17C and 17D. Such an occlusion device (80) embodiment can be delivered by release from an external sheath as described earlier. Alternately, the SE occlusion device (80) can have a non-cylindrical cross-section (110) in either or both its non-deployed or its deployed configuration.

FIGS. 18A-18D show an embodiment for a SE occlusion device (80) that has a SE stent wall structure (188) as described in earlier embodiments. In addition to having a covering (90) that extends along the entire or a portion of the stent structure (188), the stent (85) also contains an internal fabric or blocking fabric (100) that extends across the cross section of one portion of the stent (85) such as a central region (355) (see FIGS. 18A and 18B). The blocking fabric (100) can be a solid polymeric material such as PET, nylon, Pebax, polyurethane, or it can be a microporous material such as ePTFE or polyurethane, or a tightly woven film of polymer or metal or composite fibers. The film or covering (90) is folded such that it can allow for expansion of the stent (85) from its stent nonexpanded diameter (398) out to a stent expanded diameter (199) with a major axis distance (112) to meet the length of major axis of the channel (45) as shown in FIGS. 18C and 18D. The occlusion device (80) blocks blood flow through the stent lumen (105) and hence blocks blood flow through the channel (45). The release of such an occlusion device (80) is similar to that describe for other embodiments that use an outer sheath to deliver the occlusion device; removal of the sheath allows for expansion of the occlusion device (80) within the channel (45).

The SE stent (85) of the SE occlusion device (80) can have bulbous ends (400) on the proximal and distal ends (130) of the stent (85) with a larger bulb diameter (405) than the stent major axis distance (112) or stent minor axis distance (118) in the central region (355) of the stent as shown in FIGS. 19A-19C. Upon release of the covered stent (85) from the external sheath the bulbous regions expand outwards on each end of the channel (45) to further reduce the possibility for migration of the occlusion device (80) within the channel (45). The bulbous ends are thermally formed into the elastomeric metal (or polymeric or composite) stent (85) such that they have an equilibrium bulb diameter (405) upon expansion that is larger than either the stent major axis distance (112) or stent minor axis distance (118) of the central region (355) of the stent. The bulbous ends have a bulb diameter (405) that is 10% (range 5-20%) larger than either the major axis distance (112) or stent minor axis distance (118) and does not interfere with the function of the replacement leaflets found in the stent valve.

Figure 20B:
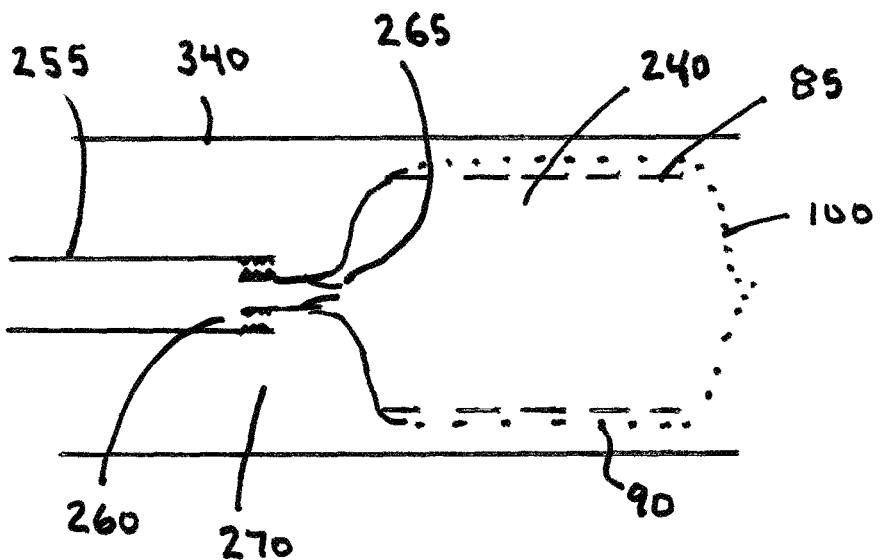
FIG. 20B is a self-expanding over the wire occlusion device that also has a dilation balloon to ensure full dilation of the stent.
Figure 20A:
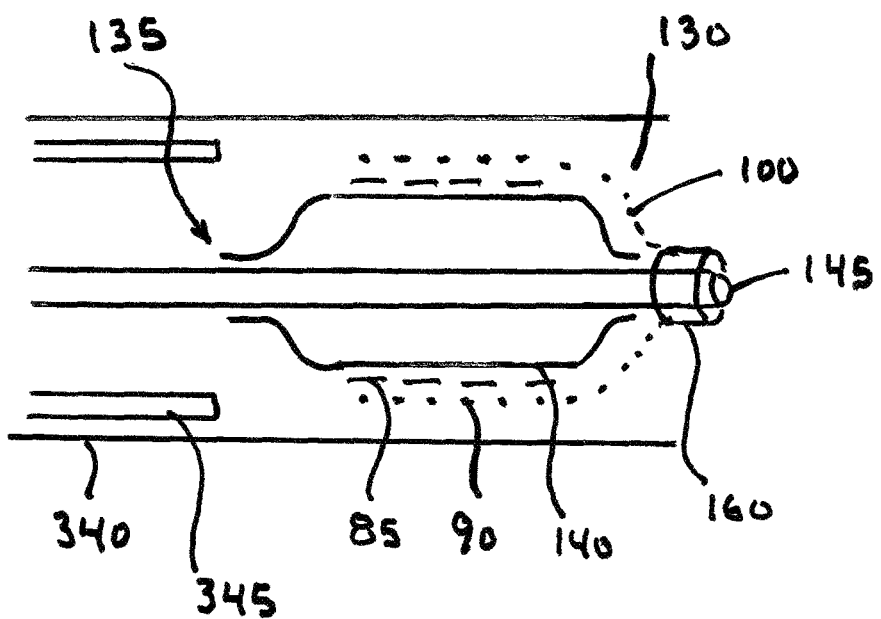
FIG. 20A is an balloon expandable occlusion device that has a distal blocking cover and that is delivered from an external sheath.

An additional embodiment for the SE occlusion device (80) of the present invention is shown in FIG. 20A. In this embodiment a SE stent (85) with a covering (90) and having a closed covering (100) located at the distal end (130) of the occlusion device (80) is positioned over an expandable balloon (140) that is positioned at the distal end of a balloon catheter. The expandable balloon (140) is an elastomeric balloon as described earlier for embodiments of the balloon expandable (BE) occlusion device. The expandable balloon (140) can be formed from silicone, polyurethane, or other elastomeric polymer, copolymer, or composite material. The occlusion device (80) is collapsed into its smaller diameter delivery configuration and held by an external sheath. The guidewire tubing for the balloon catheter (135) extends through the closed covering (100) at the distal end (130) of the occlusion device (80) and a flapper valve (160) as describe earlier allows the opening for the guidewire tube (145) through the flapper valve (160) to close upon removal of the balloon catheter. Alternately, the closed covering (100) can close via elastic contraction without the need for a flapper valve. The device is delivered OTW across the channel (45) wherein the sheath is removed allowing expansion of the SE stent (85) into the channel (45). The balloon is then expanded within the SE stent (85) to further dilate the occlusion device (80) and place it into better approximation with the channel (45) wall. The expandable balloon (140) is then deflated and the balloon catheter (135) is removed. The SE occlusion device (80) is left in place within the channel (45) making good approximation into the undulations (78) found in the channel (45) and having little chance for migration out of the channel (45).

A further embodiment for the SE occlusion device (80) of the present invention has a SE stent (85) contained completely within an occlusion balloon (240) (or attached to an occlusion balloon) which serves as a covering (90) for the occlusion device (80) as well as a blocking fabric (100) for the occlusion device; the balloon is formed from a noncompliant material having a diameter that is at least as large as the diameter of the major axis of the channel (45) (see FIG. 20B). The proximal end (270) of the balloon has a threaded attachment to a delivery tube (255) or other attachment mechanisms or holding assembly (255). The balloon-covered SE stent (85) is held into a small diameter delivery configuration via an external sheath. The device is delivered to the channel (45) via the external sheath. The device is held by the delivery tube (255) while the sheath is withdrawn allowing the SE stent (85) to expand outwards into contact with the channel (45). Next the delivery tube (255) used to inflate the balloon with either saline or curable polymer. A duckbill valve or check valve located near the proximal end (270) of the balloon ensures that the saline or polymer does not escape through the proximal end (270) of the balloon. The check valve can be eliminated, if desired, from this embodiment to allow saline inflation fluid to flow out of the balloon following delivery of the occlusion device (80) to the channel (45).

The embodiments presented in this specification are not intended to limit the scope of the present invention. Reference numerals used in the present specification for an embodiment of the present invention are intended to apply to other embodiments of the present invention.

Figure 21A:
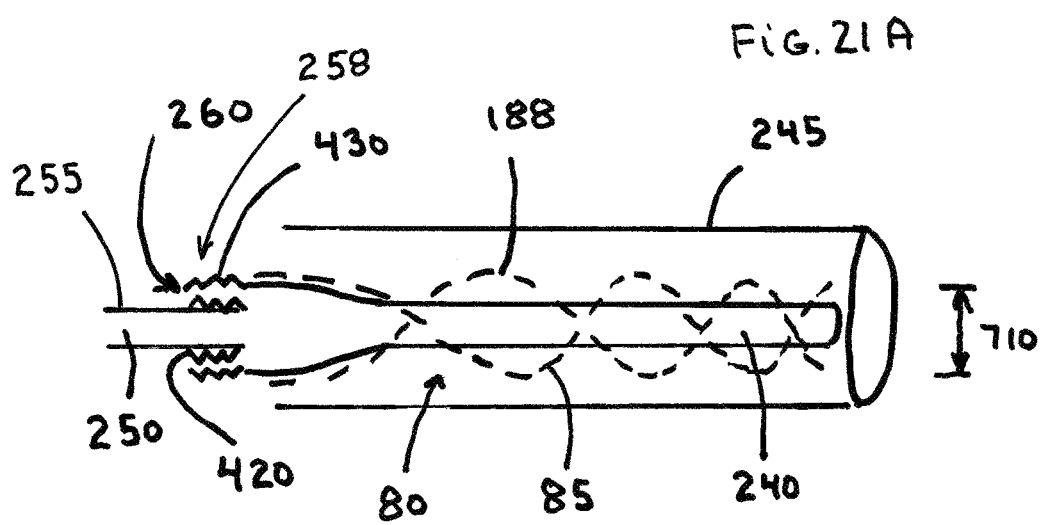
FIG. 21A is a perspective view of the occlusion device in an unreleased configuration within an external sheath.

Another embodiment for the perivalvular occlusion device (80) of the present invention is shown in FIGS. 21A-21E. As shown in FIG. 21A the delivery tube (255) is attached via a holding assembly (258) that is a screw/thread mechanism (260) to the occlusion device (80). The delivery tube thread (420) is engaged with the occlusion balloon (240) threaded receptacle (430) to allow the occlusion balloon (240) to be firmly attached to the delivery tube (255) during placement of the occlusion device (80) within the channel (45) or for retrieval of the occlusion balloon (240) if the occlusion balloon (240) is not positioned properly within the channel (45). The screw/thread mechanism (260) also allows the delivery tube (255) to be removed from the occlusion device (80) via rotational unscrewing of the threaded regions of the screw/thread mechanism (260). The threaded receptacle (430) is attached to the stent (85) which is positioned over the outside of an occlusion balloon (240). The occlusion balloon (240) serves to enlarge the stent (85) to a larger diameter within the channel as well as to serve as an occlusion member or covering (90) to prevent blood flow through the stent wall structure (188) and thereby occlude the channel (45) into which the occlusion device (80) is placed. The stent (85) of the present invention is not required to hold the channel open in an outward configuration as is typical of most vascular stents; therefore, throughout this patent application, the term, stent, is intended to mean a stent-like structure that expands from a smaller diameter configuration during delivery to a larger diameter configuration in an implanted configuration; the wall structure of the present invention provides less circumferential outward force than the outward force required for a vascular stent. The stent (85) can be formed, for example, from a braided self-expanding (SE) structure from round or flattened wires made of Nitinol, Elgiloy, or other elastically characterized metal or polymeric material use to form stent frames used in the medical device industry. The braided fibers from the SE stent (85) can be bonded, brazed, welded, swaged, for example, directly to the threaded receptacle (430) or otherwise attached to the threaded receptacle (430) via connecting members (440) that join the stent (85) to the threaded receptacle (430). The connecting members (440) can be thin metallic or polymeric fibers or elements that are contiguous with the stent (85) or can be noncontiguous members that are welded, brazed, or bonded to the stent (85) and to the threaded receptacle (430). The connecting members (440) can be a portion of the stent wall structure (188), for example, that is easily attached to the threaded receptacle (430) and can also attach to the stent body (520) as the stent expands from a smaller diameter configuration to a larger diameter configuration. The threaded receptacle (430) is also attached to the occlusion balloon (240) proximal end (450) forming a leak-tight seal with the threaded receptacle (430). Inflation of the balloon is achieved via the inflation lumen (250) found in the delivery tube (255) which communicates through the threaded receptacle (430) and into the occlusion balloon (240). The SE stent (85) is contained within an external sheath (245) that holds the stent (85) into a small unreleased diameter (710) that is approximately equal or less than the external sheath inner diameter.

Figure 21B:
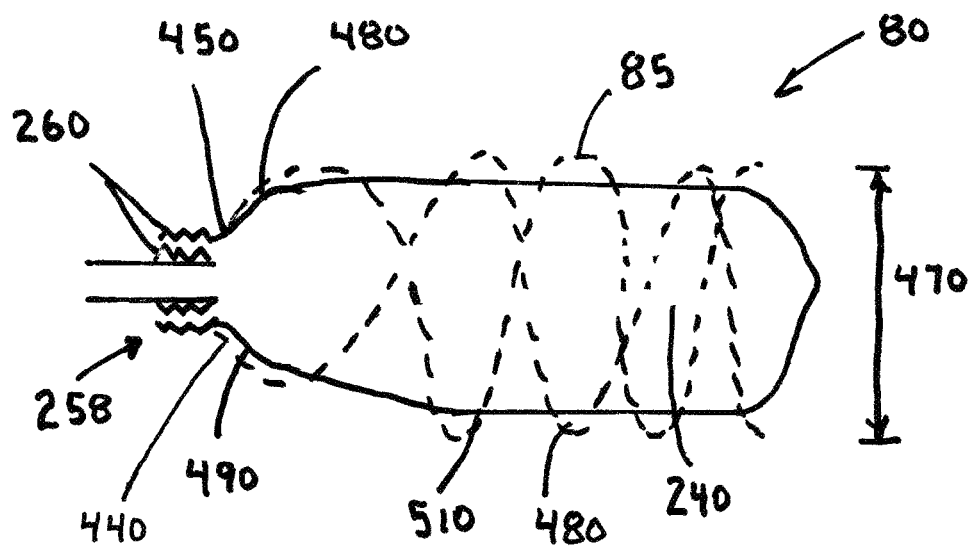
FIG. 21B is a plan view of a released occlusion device in free space with the stent in an expanded configuration and the occlusion balloon attached along the entire stent surface.

If the external sheath (245) is pulled proximally releasing the stent (85) into free space (i.e., not contained within a channel (45) or contained within an external sheath (245)) as shown in FIG. 21B, the SE stent (85) will expand outwards reaching the stent equilibrium diameter (470). A portion of the occlusion balloon (240) is attached to the stent (85) forming a balloon-stent attachment (480). The balloon-stent attachment (480) can attach the balloon cone (490) with the stent connecting region (500); the balloon-stent attachment (480) can alternately be located in the balloon cone (490) and/or the balloon body (510), and the balloon-stent attachment (480) can extend throughout the entire axial length of the stent (85) (i.e., stent body (520) plus the stent connecting region (500)). The stent body (520) is not required to be bonded to the balloon distal end (525). The stent body (520) is the region of the stent that extends within the channel (45) and extends outwards to make contact with the channel (45).

Figure 21C:
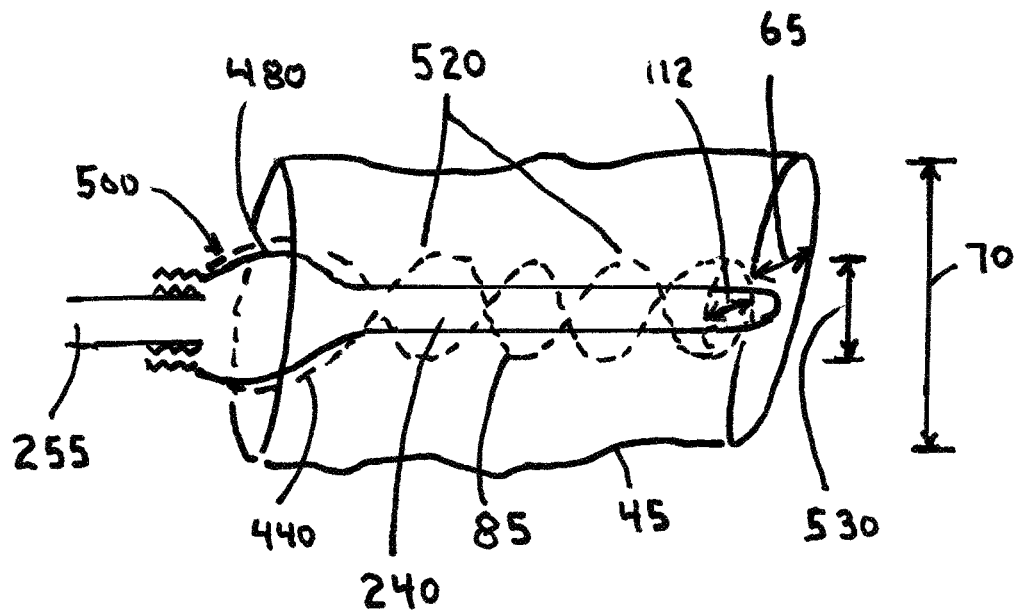
FIG. 21C is a perspective view of an occlusion device that has been released within a channel but the occlusion balloon has not yet been expanded.
Figure 21D:
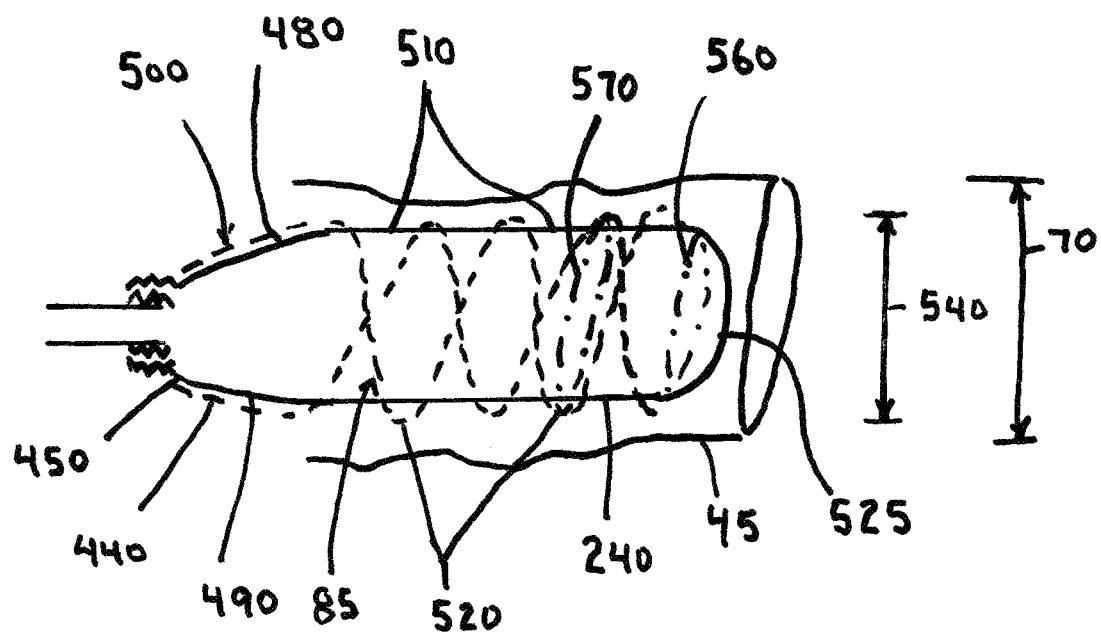
FIG. 21D is a perspective view of an occlusion device that has been released within a channel and has been expanded outwards via an occlusion balloon.

In clinical use the external sheath (245) along with the occlusion device (80) contained within the external sheath (245) are entered into the channel (45) and followed by removal of the external sheath (245) as shown in FIG. 21C. The self-expanding (SE) stent expands outwards to meet the inner walls of the channel (45) and achieve a stent minor axis distance (112) and expands partially outwards in the direction of the channel major axis to an intermediate distance (530) (i.e., between its deliverable configuration within a sheath and its post-dilation major axis distance (540)) to achieve a stent predilated major axis distance (530) that is less than the stent distal post-dilation distance (540); the balloon has not yet been inflated to achieve the stent pre-dilation major axis distance (530) or intermediate distance (530) as shown in FIG. 21C. As seen in FIG. 21D, inflation of the balloon under a pressure of 2 atm (range 1-10 atm) pushes the stent (85) outwards such that the stent (85) expands further in the direction of the channel major axis to achieve a stent post-dilated major axis distance (540) that is greater than the stent predilated major axis distance (530) and is equal to the channel major axis distance (70). Hence the entire channel (45) has been filled with the stent frame (85) along the entire channel major axis distance (70); this allows the operator to use only one device to occlude a very oblong channel (45) defined by the channel major axis distance (70) (in relative comparison to the channel minor axis distance (65)) that is not normally filled by a standard SE stent that is not post-dilated. Following occlusion of the channel (45), the delivery tube (255) is detached from the occlusion device (80), leaving the occlusion device implanted in the channel (45). The dilute contrast medium that is used to inflate the occlusion balloon (240) via the inflation lumen (250) can be allowed to be removed from the balloon as shown in FIG. 21E via either application of vacuum to the inflation lumen (250) or via detachment of the occlusion device (80) from the delivery tube (255) allowing natural leakage of a blood compatible inflation fluid out of the threaded receptacle (430).

Figure 22:
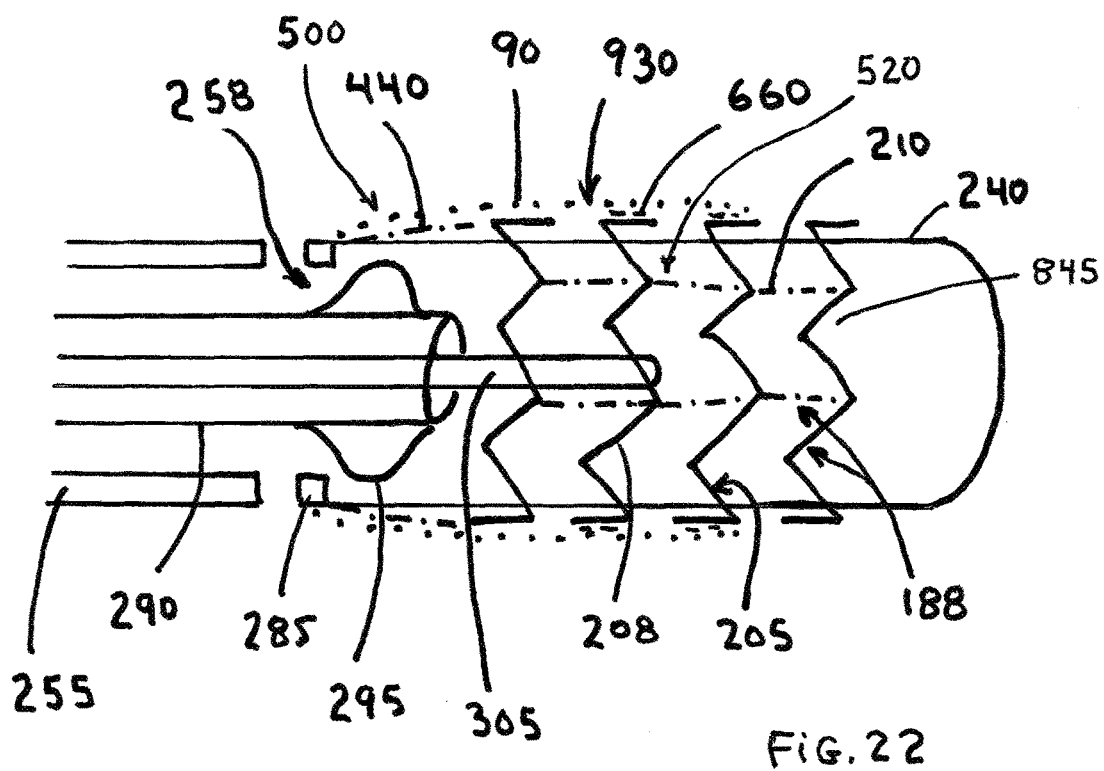
FIG. 22 is a plan view of an occlusion device having a holding assembly that has a balloon stop and member stop to hold the occlusion balloon to the delivery tube.

The occlusion balloon (240) is attached to the threaded receptacle (430); the occlusion balloon (240) is also attached to the stent (85) along one or more balloon body perimeters (560) to one or more stent body perimeters (570) located in the stent body (520). The occlusion balloon can be attached additionally along the surface of the occlusion balloon to the surface of the stent (85). Upon detachment of the inflation tube from the occlusion balloon (240) and as the inflation medium escapes from the balloon, a portion of the balloon may no longer be in contact with the stent (85), yet the occlusion device (80) will still provide occlusion of the channel (45). The occlusion device (80) will maintain occlusion of the channel (45) so long as its attachment to the stent occurs along a stent body perimeter (570) that is attached to a balloon perimeter in a region of which the stent (85) is making perimeter contact with the channel (45). The balloon can be formed from a noncompliant (NC) material such as polyethylene terephthalate (PET), for example, a semicompliant (SC) material such as Nylon or Pebax, for example, as long as the diameter of such a balloon in its fully inflated configuration is equal or greater than the major axis distance of the channel (45). The balloon can also be formed from an elastomeric material such as polyurethane, for example. The elastomeric material will tend to deform into the undulations (78) found in the channel (45) and cause the stent (85) to deform into such undulations (78). As described in earlier embodiments a polymeric material can also be used to inflate and fill the occlusion balloon (240) and form a cured or solidified polymer or gel; in this case a check valve can be used within the occlusion balloon (240) or within the holding assembly (258) to prevent escape of such polymeric material into the blood stream as described in other embodiments of the present invention. Rather than attach the occlusion balloon (240) directly to the stent wall structure (188), a covering (90) can instead be attached to the stent (85) as shown in FIG. 22. The covering (90) may be attached to the stent and the stent connecting region (500) and can extend along the stent body (520). The covering (90) can be formed from a thin polymeric film such as PET, Nylon, polyurethane, PTFE, or other polymeric film, for example which can be bonded to the stent (85) or used to encapsulate the stent (85), or form a web between the stent metal members or stent wall structure (188) to render the stent (85) impermeable to blood flow through the covering wall structure (930) or covering material construction (930).

As shown in FIG. 22 the stent wall structure (188) for the occlusion device (80) as shown in FIGS. 21A-21E can alternately be a wall structure (188) formed from rings (205) having a zig-zag structure (208); the zig-zag rings (205) are connected via connectors (210); connectors (210) are formed from metal fibers or elements that can be formed contiguously with the stent wall structure (188) that is comprised of zig-zag structure (208), for example. The occlusion device (80) can alternately be releasably attached to the delivery catheter via a variety of holding assembly (258) mechanisms. Another example of a holding assembly (258) is comprised of a hollow member (210), balloon stop (285), and member stop (295) as described in earlier embodiments. The stent (85) is attached to the holding assembly (258) via connecting members (440). The connecting members (440) can be individual flexible metallic or polymeric fibers or elements that are contiguous with the stent wall structure (188) or are separate elements that are bonded, welded, or attached to the stent (85) and to the holding assembly (258). The stent wall structure (188) can alternately be a closed cell structure or other wall structure found in vascular stents used in the medical device industry. An external sheath (245) can be used to hold the SE stent (85) down to a small diameter configuration during delivery of the occlusion device (80) to the channel (45). The holding assembly (258) can be used to retrieve the occlusion device (80) if the operator does not approve of the placement of the occlusion device (80) within the channel (45). Marker bands that are observed via fluoroscopy, echo, or CT can be located on the occlusion device (80) and on the delivery catheter to assist in locating the occlusion device (80) within the channel (45).

The covering wall structure (930) can be a microporous wall structure that is impervious to blood flow but allows for tissue healing with the covering wall structure (930). The covering can itself be formed such that it is attached to the stent wall structure (188) as a webbing that attaches to and extends between stent rings and between hinges (190) and struts (200) of the stent. The covering can alternately surround the entire stent connecting region (500), stent body (520), and stent distal end (845) and function as an occlusion balloon that can be inflated with inflation fluid. If a covering (90) is a film that is attached over a portion of the stent (85), such as a stent body (520), an occlusion balloon (240) may not be required to be bonded to the stent (85), rather the occlusion balloon can reside unattached on the inner surface of the stent.

It is understood that the stent (85) of the present occlusion device (80) invention can have a wall structure that is not limited to a braided wall structure, a zig-zag ring wall structure or a closed cell wall structure. Also the occlusion device (80) invention can have a portion of the occlusion balloon (240) bonded via a balloon-stent attachment (480) to a portion of the stent (85) to block blood flow through the stent wall structure (188) or alternately a covering (90) can be bonded to a portion of the stent (85) via a covering attachment (660) to block blood flow through the stent wall structure (188).

Figure 23A:
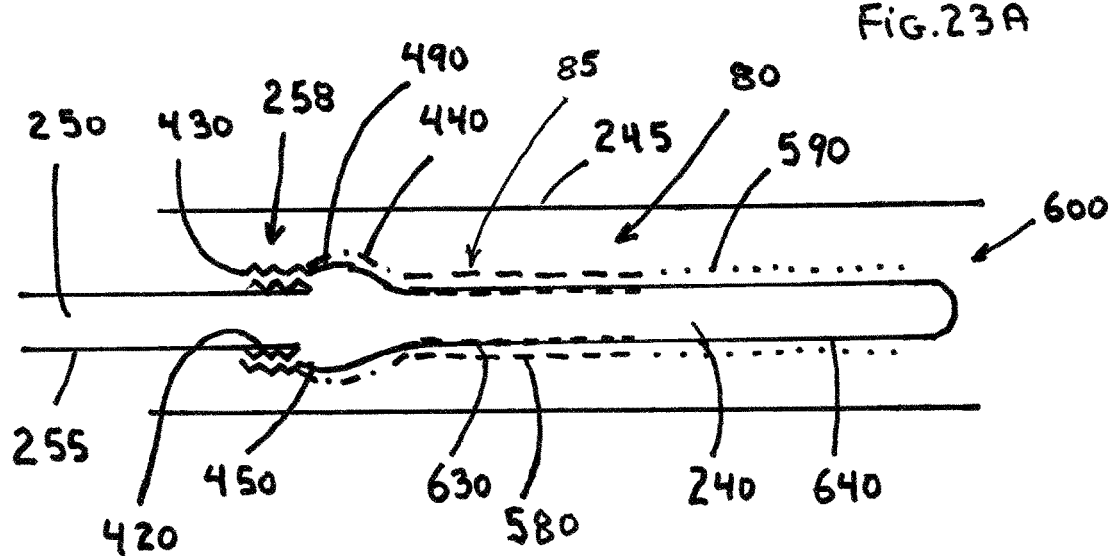
FIG. 23A is a perspective view of an occlusion device in a nonreleased configuration within an external sheath.

FIGS. 23A-23F show yet another embodiment of an occlusion device (80) that is attached to a delivery tube (255) via a holding assembly (258). The holding assembly (258) can be a screw/thread mechanism (260) as shown in FIG. 23A or it can be another configuration for a holding assembly (258). The stent (85) can be a braided stent, a series of zig-zag rings (205), or other stent wall structure (188) found in vascular stenting devices. The stent (85) is attached to the threaded receptacle (430) of the holding assembly (258) via one or more connecting members (440). The connecting members (440) can be fibers or wires used in the formation of a braided stent as described earlier or they can be thin metallic or polymeric connecting fibers or elements that are contiguous with or attached to a stent wall structure (188) or stent ring, for example, of a zig-zag ring stent or other stent wall structure (188). The stent (85) in this embodiment has a stent central body (580) that would be substantially located within the channel (45) and a stent distal body (590) which can extend distally outside of the channel distal end (730) (as seen in FIG. 24B). The stent (85) is mounted onto the outside of a occlusion balloon (240). The balloon proximal end (450) is attached to the threaded receptacle (430) and is able to receive inflation medium from the delivery tube (255) which has delivery tube threads (420) that are coupled by threads to the threaded receptacle (430). An external sheath (245) positioned around the stent (85) holds the stent in a nonreleased configuration (600).

Figure 23B:
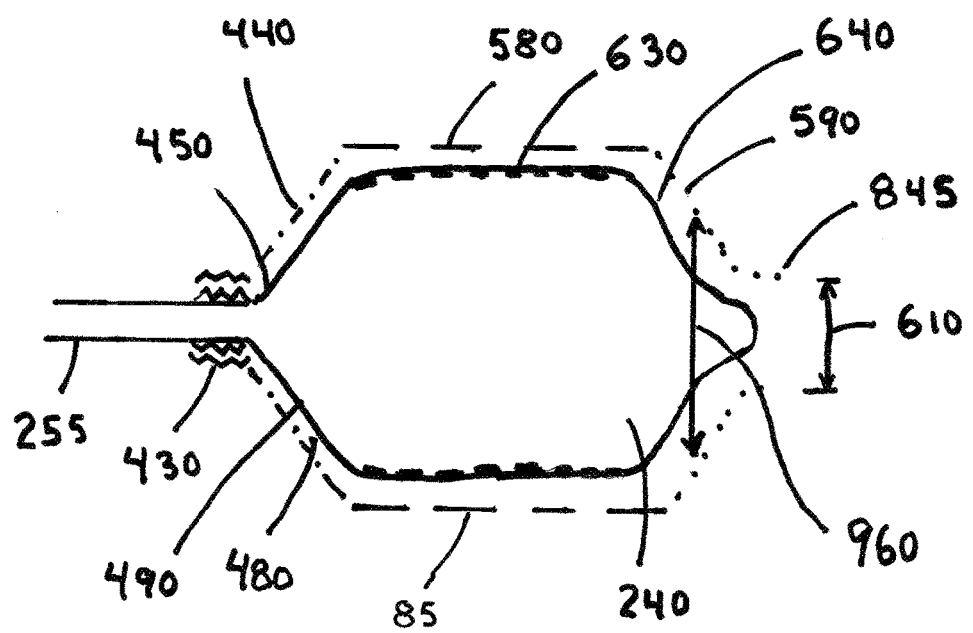
FIG. 23B is a plan view of an occlusion device that has been released from the external sheath and expanded out via the occlusion balloon in free space and the occlusion balloon allowed to deflate to an equilibrium configuration with the occlusion balloon attached to the entire stent central body.

Upon withdrawal of the external sheath (245) and releasing the occlusion device (80) into free space, the stent (85) extends outwards to achieve its equilibrium shape as shown in FIGS. 23B and 23C. The stent distal body (590) of this embodiment has a stent distal end diameter (610) that is smaller than the stent distal body diameter (960). The stent distal end diameter (610) is larger than the external sheath diameter (720); the stent distal end diameter (610) is 4 mm (range 3 mm to 10 mm); the stent distal end diameter (610) is intended to pull the stent wall structure (188) and also the distal balloon body (640) to a small diameter (following expansion and deflation of the occlusion balloon) that will not interfere with valvular leaflet function of a heart valve and push the occlusion balloon (240) that is located adjacent to the stent (85) to a smaller diameter that will not interfere with heart valve leaflet function. The stent distal body diameter (960) is equal to or greater than the channel minor axis distance (65); the stent distal body (640) has a rounded cross-sectional shape with a stent distal body diameter (960) of 8 mm (range 5-10 mm) to prevent migration of the occlusion device (80) within the channel. The stent distal diameter (610) is also larger than the stent central body minor distance (585) which is constrained within and has a diameter similar to the channel minor distance (65). The stent connecting members (440) can be attached to the occlusion balloon cone (490); the stent central body (580) can be attached to the balloon central body (630). Although the stent distal body (590) is intended to be located distal to the channel (45), the stent distal body (590) can also be attached to the balloon distal body (640), if desired. The balloon wall structure will prevent blood from travelling in a proximal direction or a distal direction (650) through the stent wall structure (188) and hence will prevent blood flow from travelling through the channel (45) in which the occlusion device (80) is placed as shown in FIG. 23B. The occlusion balloon (240) can be attached to the stent (85) along the entire axial length of the stent (85) if desired.

Alternately, as shown in FIG. 23D, a covering (90) can be placed over or attached to the stent connecting members (440), the stent central body (580), the stent distal body (590), or over the entire stent wall structure (188) via a covering attachment (660). The covering (90) can be formed from a thin polymeric material that does not allow passage of blood across or through the covering wall structure (930); the covering wall structure (930) can be a thin film of polymeric material, a woven material, or a microporous material that does not allow passage of blood across the wall thickness of the covering (90). The covering (90) can be attached to the stent (85) via adhesives, encapsulation, suturing, or other attachment methods. The occlusion balloon (240) for this version of the embodiment does not require attachment to the stent wall structure (188).

The occlusion balloon (240) for this embodiment can have a cylindrical inflated shape as shown in FIG. 23E having a balloon fully inflated diameter (670) in free space (i.e., not confined by a channel (45)) of 8 mm (range 5-10 mm) that is equal or larger than the channel minor axis distance (70). Alternately, the occlusion balloon (240) can be a shaped balloon having a balloon distal body diameter (740) that is 5 mm larger (range 3-10 mm larger) than the balloon central body diameter (800) in free space as shown in FIG. 23F. The balloon fully inflated diameter (670) should be at least 5 mm larger than the channel minor axis distance (65). The larger balloon distal body diameter (740) will assist in placement of the occlusion device (80) by providing a balloon distal fully inflated diameter (670) for the balloon distal body (640) and the stent distal fully inflated diameter (680) that is at least 5 mm larger than the channel minor axis distance (65) and can serve to assist the operator in locating the distal region of the balloon adjacent to the channel distal end (730) as will be described later. The balloon distal body provides the oversized balloon diameter relative to the channel minor distance (65) to position the occlusion device within the channel. The stent distal body distance (960) located adjacent to the channel distal end (730) is larger than the channel minor distance (65) and hence assists with preventing migration of the stent (85) in the channel following delivery of the occlusion device within the channel. Upon deflation of the occlusion balloon (240), the stent distal body (590) can assume the smaller diameter configuration (i.e., smaller than its configuration with the balloon inflated) as shown in FIGS. 23B and 23C due to the smaller stent distal equilibrium diameter (610) at the stent distal end (845) in comparison to the stent distal body diameter (960) and the balloon distal body (640) thereby will not interfere with the function of valvular leaflets located adjacent to the channel (45). The balloon distal body length (690) is approximately 10 mm (range 5-20 mm) to allow the occlusion balloon (240) to form a bulbous shape in the balloon distal body (640).

Figure 24C:
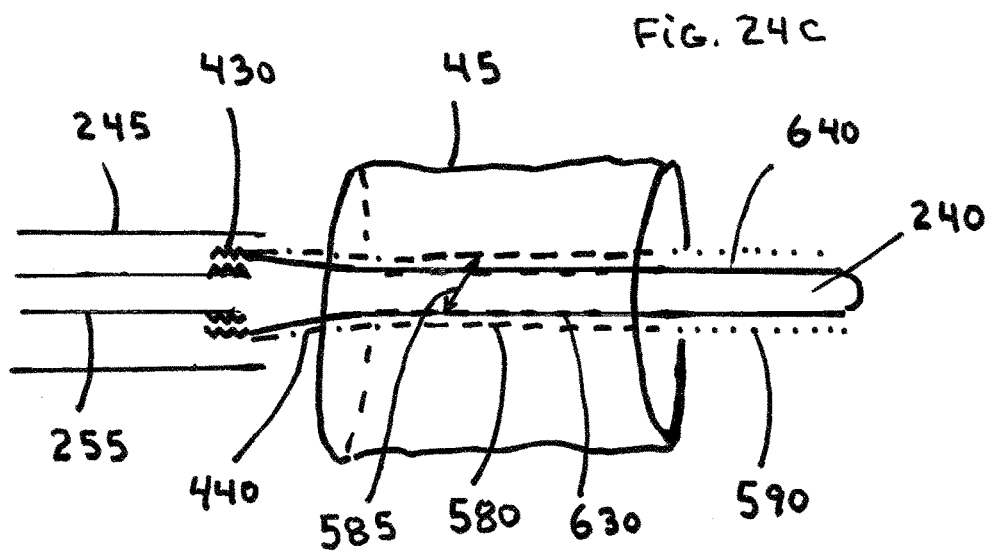
FIG. 24C is the occlusion device of FIG. 24B having the occlusion balloon deflated and the external sheath withdrawn proximally to a location proximal to the channel.

The method of use for the embodiment of FIGS. 23A-23F is shown in FIGS. 24A-24E. The occlusion device (80) is delivered to the site of the channel (45) contained within an external sheath (245). As shown in FIG. 24A the SE stent (85) is held in a stent nonreleased configuration (600) having a stent unreleased diameter (710) that is similar to the external sheath diameter (720). The stent (85) is mounted onto a occlusion balloon (240). The stent (85) is attached via connecting members (440) to the threaded receptacle (430) of the holding assembly (258). The balloon proximal end (450) is also attached to the threaded receptacle (430). Other configurations of the holding assembly (258) as described are also contemplated for this embodiment.

The external sheath (245) is placed across the channel (45) and is extended distal to the channel distal end (730). The external sheath (245) is withdrawn to expose the stent distal body (590) and balloon distal body (640) distal to the sheath distal end (700); the stent distal body (590) is located distal to the channel distal end (730). The occlusion balloon (240) is then inflated as shown in FIG. 24B causing the balloon distal body (640) to expand outwards and causing the stent distal body (590) to expand outwards. The occlusion balloon (240) can be inflated to 2 atm (range 1-10 atm) to provide the positioning aspect of the distal balloon region. The external sheath (245) and its contained delivery tube (255) can then be pulled under tension proximally to locate the distal balloon body and stent distal body (590) adjacent to the channel distal end (730) and position the stent central body (580) of the occlusion device (80) properly within the channel (45). The balloon distal body diameter (740) is greater than the channel minor axis distance (65) by at least 5 mm in order to ensure that the balloon distal body (640) of the occlusion device (80) is not able to enter the channel (45) and serves as a positioning member.

Figure 24D:
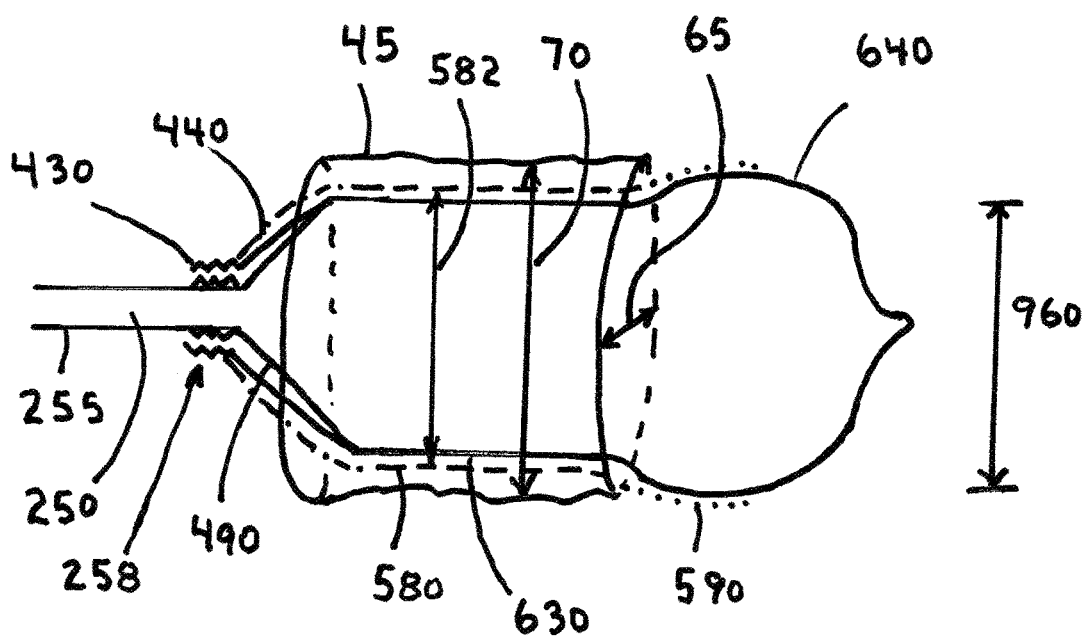
FIG. 24D is the occlusion device of FIG. 24C having the occlusion balloon inflated as second time to push the stent central body outwards into contact with the channel major axis distance and channel minor axis distance.

The occlusion balloon (240) can then be deflated and the external sheath (245) is withdrawn from the occlusion device (80) while maintaining a fixed position for the occlusion device (80) across the channel (45) as shown in FIG. 24C. The stent central body (580) has expanded outwards to form a stent central body minor distance (585) that is equal to the channel minor distance (65). The occlusion balloon (240) is again inflated to a pressure of 2 atm (range 1-10 atm) to expand the balloon central body (630) into the channel (45) and push the stent central body (580) into full contact with all of the undulations (78) found in the channel (45) as shown in FIG. 24D. The stent distal body (590) can extend to a stent distal body diameter (960) that is at least 5 mm larger than the channel minor axis distance (65) and at least 5 mm larger than the stent central body minor distance (585). The stent central body major distance (582) is larger than the stent central body minor distance (585). The balloon distal body diameter (740) is also larger than the stent central body minor distance (585).

Figure 24E:
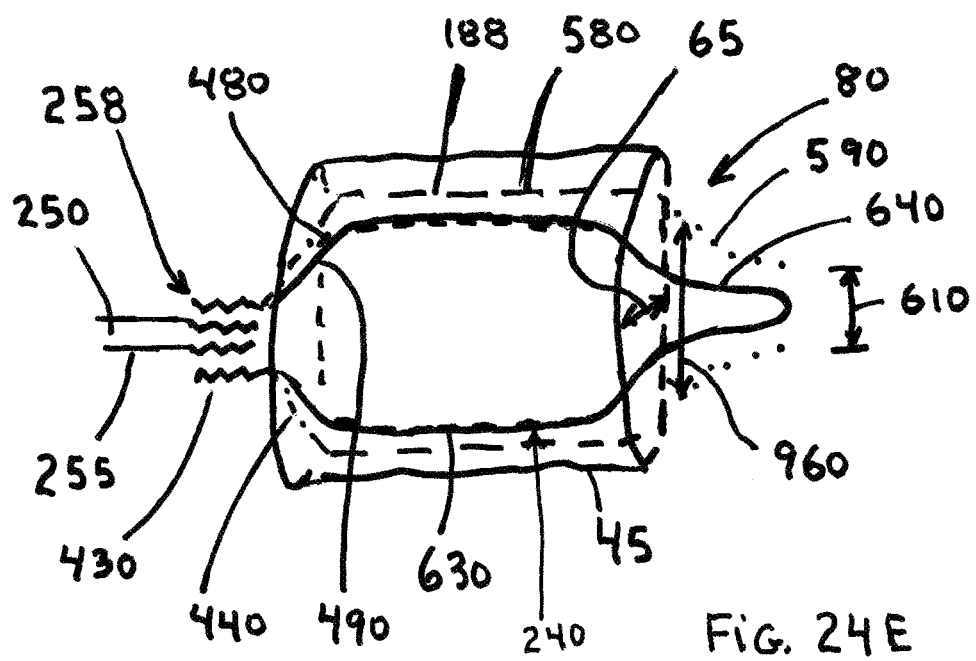
FIG. 24E is the occlusion device of FIG. 24D having the occlusion balloon deflated and causing occlusion of the channel, the delivery tube is ready to be detached from the occlusion device.

The occlusion balloon (240) is deflated either by applying vacuum to the inflation lumen (250) or by disconnecting the holding assembly (258) thereby separating the occlusion device (80) from the delivery tube (255). The balloon distal body (640) is forced to reduce in diameter by the forces applied by the stent distal body (590) which is directed toward achieving a stent distal body diameter (960) that is at least 5 mm larger than the channel minor axis (65) as shown in FIG. 24E. The balloon distal body (640) and stent distal body (590) which has a small equilibrium diameter are thereby not allowed to interfere with valvular leaflet function as the occlusion balloon (240) deflates and is implanted into the channel (45) along with the stent (85). The balloon cone (490) region can be attached to the stent connecting region (500) via a balloon-stent attachment (480) as shown in FIG. 24E; also, the balloon central body (630) can be attached to the stent central body (580). Alternately, as described in other embodiments, a covering (90) can be placed along the outside of, or attached to, the threaded receptacle, the stent connecting members (440), and the stent central body (630) to prevent blood passage through the wall structure of the covering (90) and through the stent wall structure (188) and hence provide occlusion of the channel (45). If the operator identifies that the occlusion device (80) is not placed properly access the channel (45), the occlusion device (80) can be withdrawn back into the external sheath (245) by applying tension to the delivery tube (255) or delivery catheter prior to disconnecting the holding assembly (258). Application of vacuum to the inflation lumen (250) will assist in reducing the diameter of the occlusion balloon (240) and the stent and assist in retrieval of the occlusion device (80) back into the external sheath (245), especially in those embodiments where the stent (85) is attached directly to the occlusion balloon (240).

The occlusion balloon (240) for the embodiment described in FIGS. 23A-24E can be formed from a noncompliant material such as PET, for example, or from a semi-compliant material such as Nylon or Pebax, for example. The balloon distal body (640) can be formed with a dilated diameter that was equal to the channel major axis distance (70) or at least 5 mm larger than the channel minor axis distance (65). Alternately, the balloon can be formed from an elastomeric material such as polyurethane, for example. An elastomeric balloon material provides a benefit of dilating via a uniaxial or biaxial extension of the material (rather than unfolding of the balloon material) and can extend into the undulations (78) of the channel (45) without a requirement for unfolding of the balloon. If an elastomeric polymer is used for the balloon distal body (640), a braided fiber structure can be integrated into or attached to balloon the wall structure to provide strength against balloon excess expansion and rupture during direct expansion of the stent (85) within the channel undulations (78). The wall structure of the stent can be any wall structure found in stents used for vascular stenting, including, for example, braided structures formed from SE metal fiber braids, SE zig-zag rings (205) connected by connectors (210), closed cell structures formed from metal, alloys of metal, polymer, biodegradable materials, or other materials used as stent materials. The stent wall structure (188) can also incorporate the SE hinge (109) and strut (200) structure (see FIGS. 15A-15B) as described in earlier embodiments having a hinge region (195) that has a hinge radial dimension (225) that is greater than a strut radial dimension (230) to provide greater expansion deformation force; the struts (200) can have thinner strut radial dimension (230) to allow the strut (200) to bend easier around a small radius of curvature in the circumferential direction. Also, the stent wall structure (118) can comprise the stent shapes described in FIGS. 16A-16E.

FIGS. 24F-24H and 24J-24M show an embodiment of the occlusion device (80) that is similar to the embodiment shown in FIGS. 23A-23F and whose method of use is described in FIGS. 24A-24E but with an altered stent (85) shape that is intended to reduce migration of the stent (85) within the channel (45). The occlusion device (80) comprises a SE stent (85) that is located on the outside of an occlusion balloon (240) and attached to the balloon in the stent connecting region (500) and in the stent central body (580) forming a balloon-stent attachment (480). The occlusion device (80) can alternately have a covering attached to the stent connecting region (500) and stent body (520) and the occlusion balloon is not required to be attached to the stent (85).

Figure 24F:
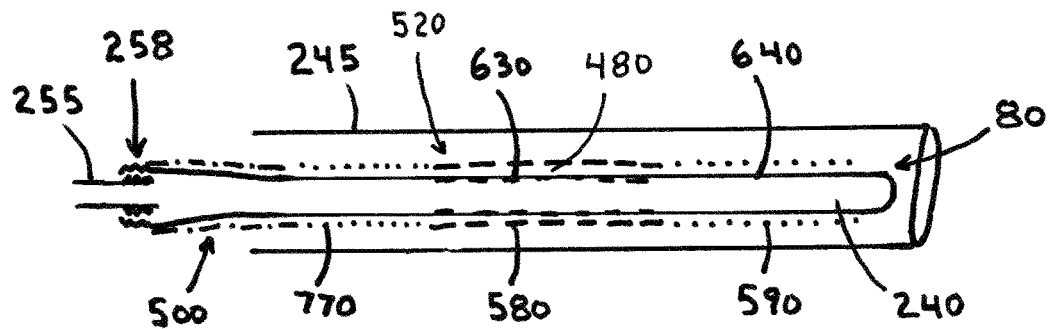
FIG. 24F is a perspective view of an occlusion device positioned within an external sheath; the stent has a stent distal body, stent central body, and stent proximal body mounted on the outside of an occlusion balloon.
Figure 24G:
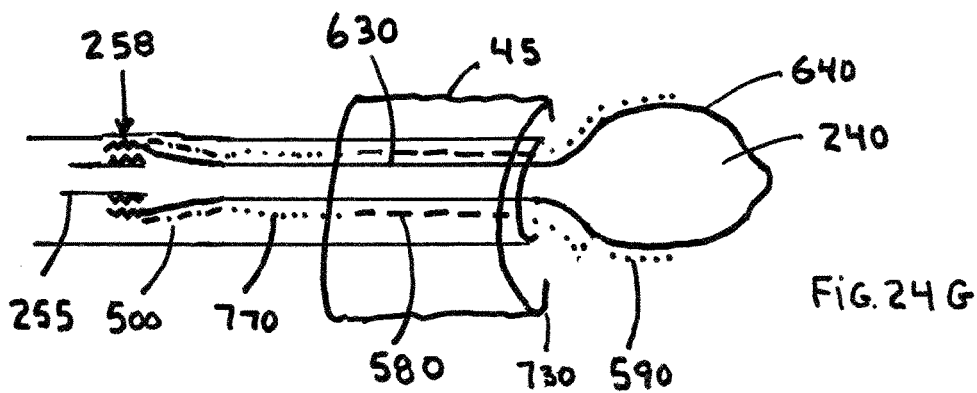
FIG. 24G is a perspective view of an occlusion device of FIG. 24F located with the external sheath within a channel and having the distal stent body and distal balloon body in an expanded configuration located distal to the channel for positioning the occlusion device within the channel.
Figure 24J:
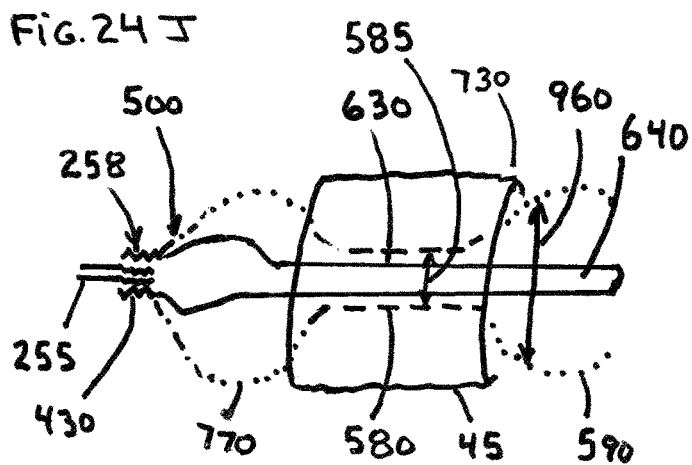
FIG. 24J is a perspective view of the occlusion device of FIG. 24G subsequent to deflation of the occlusion balloon and retraction of the external sheath; the stent proximal body is positioned proximal to the channel.
Figure 24H:
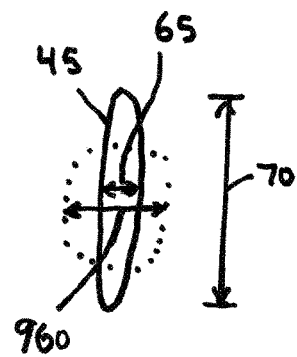
FIG. 24H is a cross-sectional view of the stent distal body showing a rounded shape that is larger than the channel minor distance.
Figure 24K:
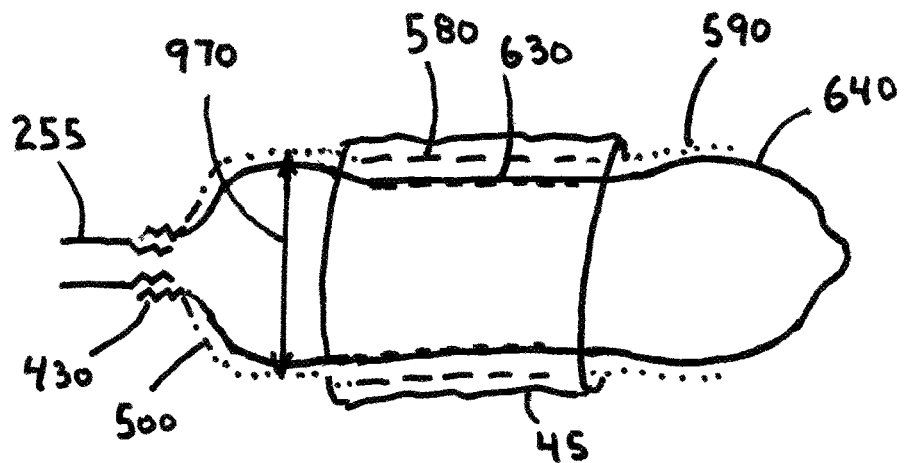
FIG. 24K is a perspective view of FIG. 24J having the occlusion balloon inflated a second time and showing the stent central body being expanded outwards to contact the channel major axis distance and channel minor axis distance.
Figure 24L:
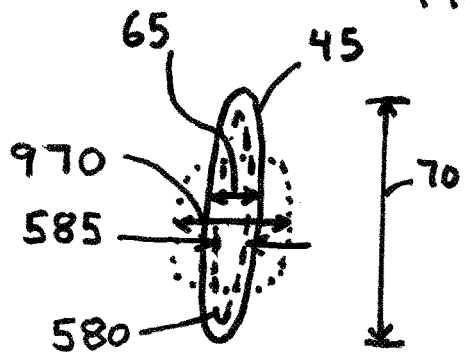
FIG. 24L is a cross-sectional view through the stent proximal body of FIG. 24K showing the stent proximal body diameter being larger than the channel minor distance to prevent migration of the occlusion device within the channel.
Figure 24M:
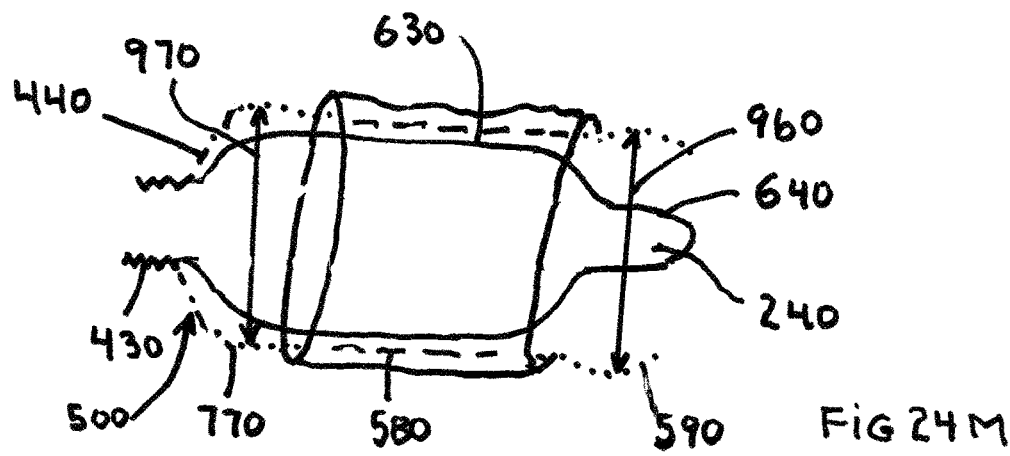
FIG. 24M is the occlusion device of FIG. 24K following deflation of the occlusion balloon and detaching the delivery tube from the occlusion device.

The occlusion device (80) is delivered within an external sheath (245) as shown in FIG. 24F. The stent (85) has a stent proximal body (770), a stent central body (580), and a stent distal body (590). The stent distal body (590) along with the balloon distal body (640) are positioned downstream of the channel (45) and the balloon central body (630) along with the stent central body (580) are retained within the external sheath (245) as shown in FIG. 24G, and the balloon distal body (640) is inflated to locate the stent distal body (590) adjacent to the channel distal opening (830) as described in the embodiment of FIGS. 24A-24E and to position the stent distal body (590) adjacent to the channel distal end (730). In this embodiment the stent distal body (590) is has an equilibrium configuration with a stent distal body diameter (960) that is larger (at least 5 mm larger) than the channel minor distance (65) as shown in FIG. 24H; this stent distal body equilibrium configuration is retained even after the occlusion balloon (240) has been deflated following this positioning step. The stent distal body diameter (960) is located a few millimeters downstream of the channel distal end (730) such that the stent distal body (960) has formed a round cross-sectional shape as shown in FIG. 24H. Following positioning of the occlusion device (80), the occlusion balloon (240) can be deflated and the external sheath (245) can be retracted under tension while maintaining a fixed position for the occlusion device as shown in FIG. 24J. The stent proximal body (770) has an equilibrium configuration that enlarges in diameter when it is not constrained by the external sheath (245) as shown in FIG. 24J. The stent distal body diameter (960) is greater than the stent central body minor distance (585) which is constrained by the channel minor axis (65). The stent proximal diameter (970) is greater than the stent central body minor distance (585). A second inflation of the occlusion balloon (240) causes the stent central body (580) to expand outwards into contact with the undulations of the channel (45) as shown in FIG. 24K. Upon deflation of the occlusion balloon (240) the stent proximal body (770) is retained with a stent proximal diameter (970) that is at least 5 mm larger than the channel minor distance (65) as shown in FIGS. 24L and 24M. The stent proximal body diameter (970) is larger than the stent central body minor distance (585) by at least 5 mm. The stent proximal body (770) has formed a rounded configuration with a stent proximal body diameter (970) as shown in FIG. 24L. As shown in FIG. 24M the occlusion balloon is attached to the threaded receptacle (430) and along the stent body extending to the stent central body (580). Alternately, a covering (90) as described earlier can be attached to the threaded receptacle (430) and extend along and attach to the stent central body (580); if a covering is used, the occlusion balloon need not be attached to the stent body and can be allowed to deflate to an empty deflated configuration.

One advantage of this occlusion device (80) embodiment over standard occlusion devices currently being used in the clinic is that positioning of the stent distal body (590) adjacent to the channel distal end (730) is enhanced (over a device without an occlusion balloon (240)) due to the inflation of the balloon distal body (640) at a location distal to the channel distal end (730). The distal balloon body is inflated to a balloon distal diameter (910) that is greater (range 5-10 mm greater) than the channel minor axis thereby locating the stent distal body (590) adjacent to the channel distal end (730). The stent distal minor distance (760) can be smaller than a distal bulb diameter of a standard occlusion device that does not comprise an occlusion balloon (240); the stent distal body diameter (960) of the present invention is only 8 mm larger (range 5-10 mm larger) than the channel minor distance and thereby does not protrude into the blood flow path or adversely affect the function of the valve leaflets of the valve having the perivalvular leak. A similar condition occurs for the stent proximal body diameter (970) of the present invention which is only 8 mm larger (range 5-10 mm larger) than the channel minor distance. The stent proximal body (770) then does not project into the blood flow path of the valve and does not interfere with the valve leaflet function as with current standard perivalvular leak occlusion devices. The stent proximal body (770) only has a requirement to prevent migration of the occlusion device (80) in the channel (45).

A covering (90) may be attached to the stent (85) as described in other embodiments to further ensure that blood cannot flow through the wall structure of the stent (85) and thereby the covering (90) can prevent blood flow through the channel (45). The covering can be attached to the holding assembly (258), the stent connecting region (500), stent proximal body (770), and stent central body (580). The wall structure for the stent body (520) of the present embodiment can be any wall structure used in a SE stent used in the vasculature. The stent wall structure (188) can also be the stent wall structure which is described in FIGS. 15A-15B which has hinges (195) and struts (200) that can expand with a greater outward force provided by the large hinge radial dimension (225) and can bend easily around the tight turns of a channel (45) due to the very small strut radial dimension (230) relative to the hinge radial dimension (225). The struts (200) can have also have the structure as described in earlier embodiments and shown in FIGS. 16A-16E.

Figure 25A:
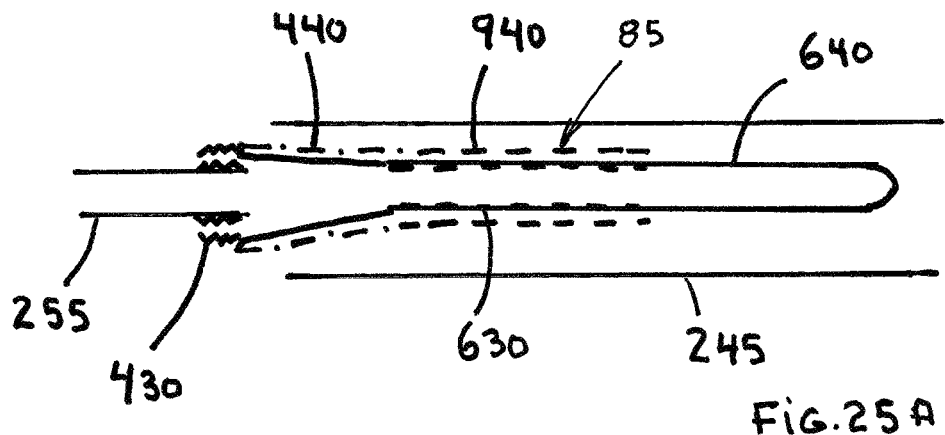
FIG. 25A is an occlusion device having a balloon expandable stent positioned on the outside of an occlusion balloon and located within a delivery sheath.

In a further yet another embodiment of the present invention the stent (85) is a BE stent (940) can be located over the balloon central body (630) while providing the balloon distal body (640) without a stent overlaying this portion of the occlusion balloon (240); the balloon distal body (640) alone (i.e., without a stent on the outside) thereby serving as a positioning member as shown in FIGS. 25A-25G. The stent connecting members (440) are attached to the threaded receptacle (430) as described in earlier embodiments. The balloon distal body (640) extends distally from the BE stent (940). The occlusion device (80) is delivered to the region of the channel (45) within an external sheath (245) as shown in FIG. 25A. The occlusion balloon (240) can be a cylindrically shaped NC or SC balloon having an inflated diameter that is equal or greater than the channel major axis distance (70) or at least 5 mm larger than the channel minor axis distance (65). The occlusion balloon (240) can be a shaped balloon formed from a NC or SC material and having a balloon distal body (640) fully expanded diameter that is 10 mm (range 5 mm-15 mm) larger than the balloon central body (630) fully expanded diameter; the balloon distal body diameter (740) is at least 5 mm larger than the channel minor axis distance (65) to serve as a positioning member to locate the occlusion device (80) adjacent the channel distal end (730). The occlusion balloon (240) can alternately be formed from an elastomeric material that is able to expand via uniaxial or biaxial expansion without unfolding of the balloon material and can thereby extend into the undulations (78) of the channel (45). A fiber braid can be located within the elastomeric balloon distal body (640) wall structure or attached to the elastomeric balloon via encapsulation or bonding methods to ensure that the balloon distal body (640) can attain a maximum inflation diameter that is not so large that the balloon distal body (640) interferes with valvular leaflet function or breaks due to excessive inflation pressures.

Figure 25B:
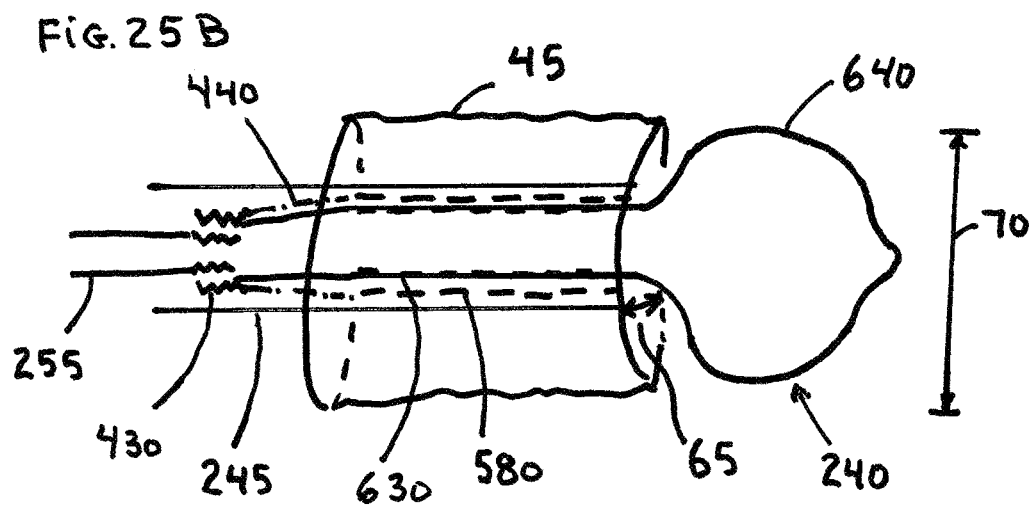
FIG. 25B is an occlusion device of FIG. 25A that has been positioned within a channel, the stent central body and balloon central body are located within a delivery sheath; the occlusion balloon has an inflated balloon distal body located distal to the channel for positioning of the occlusion device within the channel.

When using the embodiment of FIGS. 25A and 25B, the external sheath (245) is located across the channel (45); the external sheath (245) is withdrawn to expose the distal balloon region while the external sheath (245) still surrounds the BE stent (940) and the balloon central body (630) as shown in FIG. 25B. The occlusion balloon (240) can then be inflated to expand the balloon distal body (640) to a diameter that is greater than the channel minor distance (65) by at least 5 mm. Tension is applied to the external sheath (245) and the delivery tube (255) to pull the balloon distal body (640) adjacent to the channel distal end (730) and locate the BE stent (940) within the channel (45) as shown in FIG. 25B.

Deflation of the occlusion balloon (240) allows (by reducing friction between the stent (85) and the external sheath (245)) the external sheath (245) to be retracted further while maintaining position of the occlusion device (80) across the channel (45); the BE stent (940) is no longer contained within the external sheath (245) and is located within the channel (45). The occlusion balloon (240) is inflated to push the BE stent (940) outwards into contact with the undulations (78) of the channel (45) as shown in FIG. 25C. The fit of the BE stent (940) into the channel (45) undulations (78) prevents the BE stent (940) from embolizing out of the channel (45). Following deflation of the occlusion balloon (240) via application of vacuum to the inflation lumen (250), the occlusion device (80) can then be detached from the delivery catheter via unscrewing the screw/threat mechanism (260) or otherwise detaching the occlusion balloon (240) from the delivery catheter. The inflation medium can further be allowed to leak out naturally from the balloon and out of the open threaded receptacle (430). For the version having an elastomeric balloon, the balloon can naturally reduce in diameter to a smaller diameter representative of its balloon equilibrium diameter of 2 mm (range 1.5-4 mm).

The covering (90) can be attached to the stent connecting members (440) and to the stent wall structure (188) to prevent passage of blood flow through the covering (90) and hence to occlude the channel (45). The stent wall structure (188) for this embodiment can be similar to any BE wall structure used in vascular stenting. Alternately a hinge (195) and strut (200) structure can be applied that allows improved apposition of the stent (85) to the undulations (78) found in the channel (45) as described in earlier balloon expandable (BE) embodiments of the present invention (see FIGS. 6A-6C). The BE hinge (190), for example can have thin hinge width that allows the hinge to bend easily around tight radius of curvature bends. The strut (200) can be very thin such that they bend easily in the direction of the circumferential direction. Also, the strut (200) can have a crown-shape in the direction of the strut width, as described in FIGS. 16A-16E and in other embodiments. Retrieval of the occlusion device (80) of the present embodiment can be attained after positioning the occlusion device (80) within the channel (45) and exposure of the occlusion balloon (240) to a low pressure of 1 atm (range 0.5-3 atm) to inflate the balloon distal body (640) and locate the balloon distal body (640) adjacent to the channel distal end (730). Retrieval of the occlusion device (80) is obtained by deflating the occlusion balloon (240) and applying tension to the delivery tube (255) and pulling the occlusion device (80) back into the external sheath (245) for repositioning or removal. Once position and occlusion have been confirmed a high pressure of 3 atm (range 2.0-10 atm) is applied to the occlusion balloon (240) to set the BE stent (940) firmly within the channel (45), ensure that stent mobilization is not able to occur, and effect full channel (45) occlusion capability. It is understood that the stent described in FIGS. 25A-25C could alternately be a SE stent; a SE stent is better adapted to be retrievable with the delivery sheath (245) if the position of the occlusion device is not acceptable to the operator.

Figure 26A:
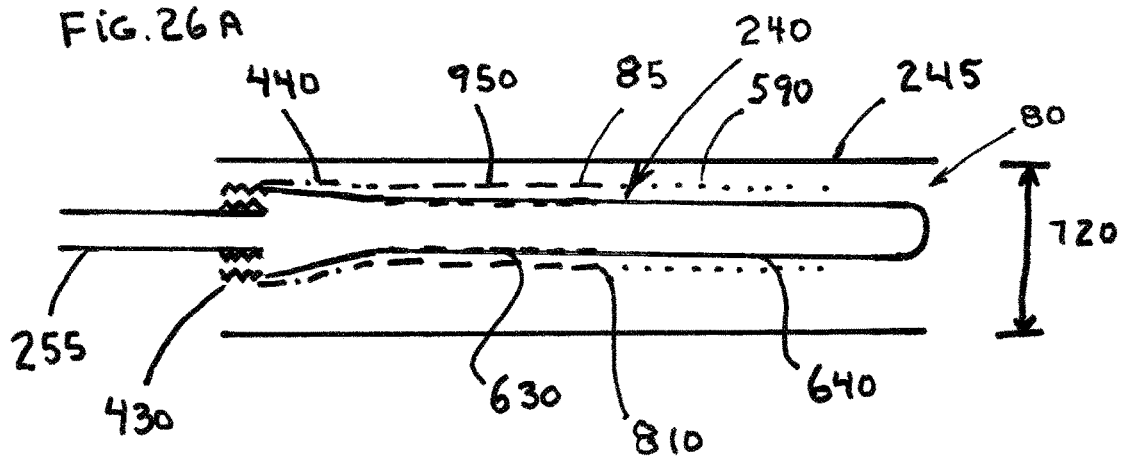
FIG. 26A is a plan view of the occlusion device positioned within an external sheath, the stent central body having a balloon expandable construction.

In still further another embodiment for the occlusion device (80) the stent (85) has a BE stent central body (950) that is BE and a stent distal body (590) that is SE as shown in FIGS. 26A-26D. The stent (85) is positioned on the outside of a occlusion balloon (240) and is contained within an external sheath (245) as shown in FIG. 26A. The occlusion balloon (240) can be cylindrical in shape or it can be a shaped balloon having an enlarged balloon distal body (640). The occlusion balloon (240) can be formed from NC, SC, or elastomeric polymer material. The balloon distal body diameter (740) in an expanded configuration is at least 5 mm larger than the channel minor axis distance (65); the balloon central body diameter (800) in an expanded configuration is larger than the channel major axis distance (70) to ensure that the balloon can expand the stent (85) to the full channel major axis distance (70). The stent distal body (590) has an equilibrium diameter (610) at the stent distal end (845) that is larger than the diameter of the external sheath (245), 4 mm (range 3-10 mm). The BE stent central body (950) is able to attain an expanded diameter equal to the channel major axis distance (70), or at least attain a perimeter that will contact the entire perimeter of the channel (45). The BE stent central body (950) is joined to the stent distal body (590) at a stent junction (810). The stent junction (810) can be formed by welding, brazing, soldering, bonding, suturing, or otherwise joining a balloon expandable (BE) stent portion to a SE stent portion. Alternately, the SE and BE stent (85) and stent junction (810) can be formed contiguously by laser machining from a tube of Nitinol, for example by machining geometrical dimensions for the hinge regions (195) that deform either by SE or BE character during expansion deformation of the stent (85) (see FIGS. 6A-6C and 15A and 15B). For example, a long hinge length will provide a SE hinge; a short hinge length that is shorter than its hinge radial dimension (225) provides a plastically deformable hinge (190) that is consistent with BE behavior. Further, the hinge regions (195) of a contiguously formed Nitinol stent can be thermally altered to change its metal crystal structure and cause the hinge (190) to exhibit either BE behavior or SE behavior.

Figure 26B:
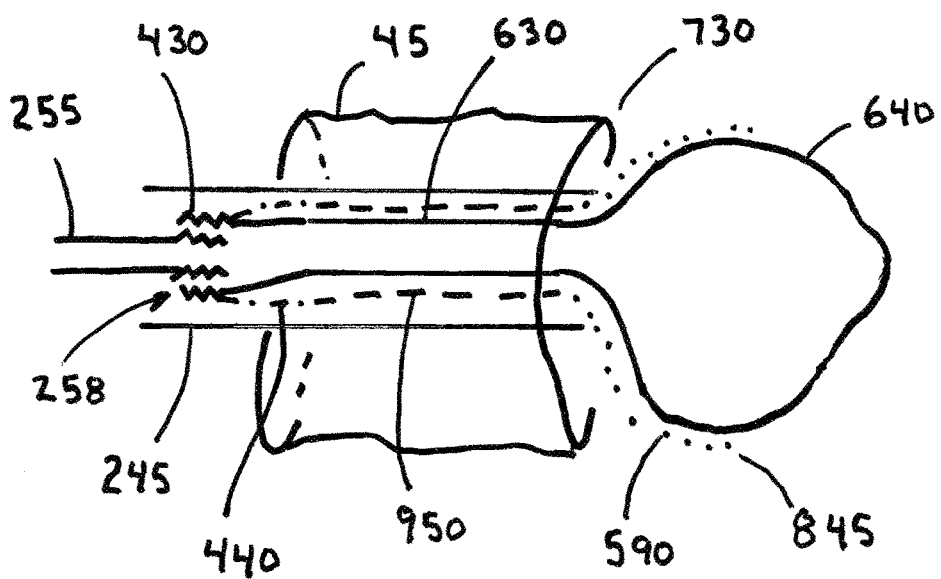
FIG. 26B is a perspective view of the occlusion device of FIG. 26A located within the external sheath and within a channel and having the stent distal body and balloon distal body extending distal to the channel, the balloon distal body is inflated to allow the occlusion device to be positioned properly within the channel.

After the external sheath (245) is positioned across the channel (45), the external sheath (245) is withdrawn exposing the balloon distal body (640) to the valve tissue distal to the channel (45) while maintaining the stent central body (950) contained within the external sheath (245). The occlusion balloon (240) is inflated at 2 atm (range 1-3 atm) to inflate the balloon distal body (640) and expand the stent distal body (590) as shown in FIG. 26B. The enlarged balloon distal body (640) serves as a positioning member that can be located adjacent to the channel distal end (730) by applying tension to the delivery tube (255).

Figure 26C:
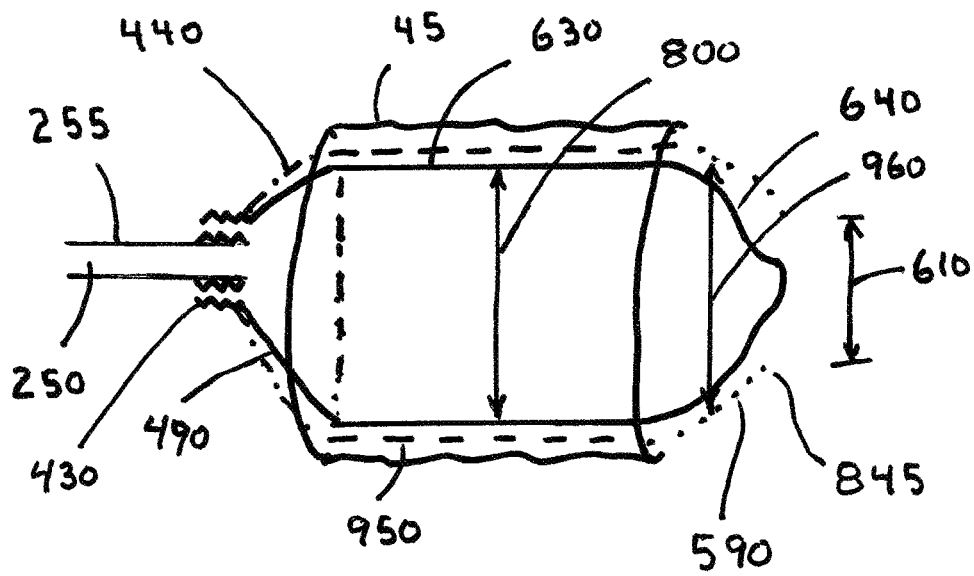
FIG. 26C is the occlusion device of FIG. 26B having had the occlusion balloon deflated and the external sheath withdrawn proximal to the channel and having the occlusion balloon inflated a second time to expand the stent central body into contact with the channel major axis distance.
Figure 26D:
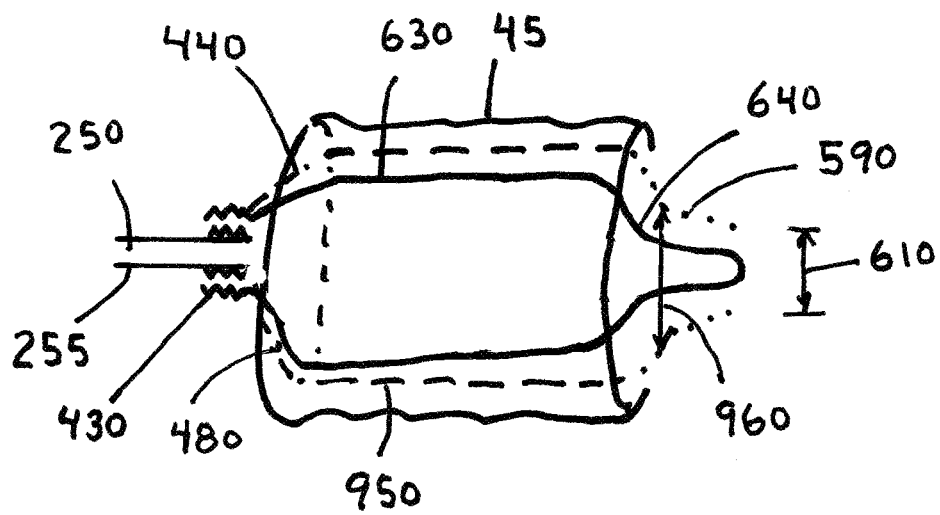
FIG. 26D is the occlusion device of FIG. 26C having the occlusion balloon deflated and allowing the stent distal body to have a stent distal body diameter that is larger than the channel minor distance.

After further retraction of the external sheath (245) to expose the entire occlusion device (80) out of the external sheath (245), the occlusion balloon (240) is inflated to a low pressure of 1 atm (range 0.5-1.5 atm) to check for positioning of the occlusion device (80) within the channel (45) and observe occlusive behavior of the occlusion device (80). Retrieval of the device at this stage is achievable by pulling the occlusion device (80) back into the external sheath (245). Upon identification of proper positioning additional inflation pressure of 3 atm (range 2-10 atm) are used to further expand the BE stent central body (950) into the undulations (78) of the channel (45) as shown in FIG. 26C.

Upon deflation of the balloon via application of vacuum to the inflation lumen (250), the SE stent distal body (590) retracts to a stent distal end diameter (610) at the stent distal end (845) of 4 mm (range 3-8 mm) and reduces the diameter of the balloon distal body (640) such that the balloon body (510) and stent distal body (590) do not impact upon the valve leaflets and do not influence valve function (see FIG. 26D); the stent distal body (590) has at least a 5 mm larger stent distal body diameter (960) than the channel minor distance (65) and assists in preventing migration of the occlusion device (80) in the channel. This embodiment can have the balloon attached to the stent (85) via a balloon-stent attachment (480); alternately, a covering (90) can be attached to the connecting members (440), or BE stent central body (950) to prevent blood flow from passage through the covering wall structure (930) and the stent wall structure (188), thereby causing occlusion of the channel (45).

It is understood that each of the embodiments of the present invention can incorporate design aspects taken from other embodiments. Reference numerals and reference nomenclature used throughout the present application bear the same definition or description as described in other embodiments unless specifically defined in a particular embodiment.

Another embodiment for a perivalvular leak occlusion device (80) is shown in FIGS. 27A-27D. In FIG. 27A the occlusion device (80) is seen in an non-expanded configuration with a SE stent (85) mounted onto the outside of a occlusion balloon (240) along the balloon central body (630). The occlusion balloon (240) and stent (85) are held into a non-expanded configuration by an external sheath (245). The balloon is releasably attached to a delivery tube (255) via a releasable holding assembly (258), the holding assembly (258) can be a threaded receptacle (430) assembly as shown in the present embodiment. The balloon proximal end (450) has a threaded receptacle (430) attached; the threaded receptacle (430) is releasably attached to delivery tube threads (420) of the delivery tube (255). Inflation medium is able to be delivered via the inflation lumen (250) of the delivery tube (255) through the threaded receptacle (430) and into the occlusion balloon (240).

To deliver the occlusion device (80) to the perivalvular leak channel (45) the occlusion device (80) and external sheath (245) are advanced through the vasculature of the body and into the channel (45) of the perivalvular leak. The external sheath (245) is withdrawn proximally exposing the balloon distal body (640) near the distal end (730) of the channel (45) as shown in FIG. 27B. Delivery of inflation medium such as contrast medium is introduced into the occlusion balloon (240) causing the balloon distal body (640) to expand; the balloon distal body (640) then serves as a positioning device allowing the operator to pull the external sheath (245) and delivery tube (255) along with the occlusion device (80) under tension to place the balloon distal body (640) into contact with the channel distal opening (830). The balloon distal body diameter (740) is greater than the channel minor dimension (65) and can be larger than the channel major distance (70) therefore will locate at the channel distal end (730) without entering the channel (45). Once the occlusion balloon (240) is in position, dilation pressure within the balloon can be reduced or removed and the external sheath (245) can be withdrawn under tension while maintaining fixed position for the occlusion device (80) within the channel (45); the balloon central body (630) along with the stent (85) are no longer contained by the external sheath (245). The stent body (85) will enlarge to form a stent body minor distance (585) that is constrained by the channel minor distance (65) and hence has a similar minor axis dimensions. The occlusion balloon (240) is again inflated as shown in FIG. 27C to expand the stent (85) outwards into contact with the undulations (78) of the channel (45) to form a stent central body major distance (582) that is larger than a stent central body minor distance (585). The balloon central body diameter (800) is equal to or greater than the channel major dimension (70) to push the stent (85) into the undulations (78) found in the channel (45). The stent (85) is attached to the balloon central body (630) via a balloon-stent attachment (480); such attachment can be made via a flexible adhesive or via use of a polymeric material that joins the stent (85) with the balloon surface. The balloon thus can serve as a covering (90) for the stent (85) to prevent flow of blood through the stent proximal end (840) and through the channel (45). The inflation pressure can again be reduced and the threaded receptacle (430) can be detached (via unscrewing the delivery tube (255)) separating the occlusion balloon (240) from the deliver tube as shown in FIG. 27D. The inflation fluid can be allowed to leak out of the threaded receptacle (430) following implantation of the occlusion device (80) into the channel (45).

The occlusion balloon (240) serves as an occlusion member that is held outwards by the outward forces provided by the SE stent (85). The stent central body (580) has an equilibrium diameter that is equal the channel major distance (70). Saline based contrast medium used to inflate the balloon can be allowed to leak out of the balloon over time. Alternately, a one-way valve (i.e., a flapper valve (160) described in an earlier embodiment) with leaflets that directs flow toward the balloon interior (but not out of the balloon) can be located within the occlusion balloon (240) or within the threaded receptacle (430) to hold the inflation medium within the balloon for longer periods of time. If necessary a hollow tubing can be inserted through the delivery tube (255) and across the one-way valve to release inflation medium from the balloon prior to release of the balloon from the delivery tube (255) if desired; such release of inflation medium can be required, for example, if the occlusion device (80) having a one-way valve is deflated and the stent (85) is unexpanded and the occlusion device (80) is repositioned within the channel (45). It is understood that the inflation balloon can alternately be inflated or filled with a polymeric medium such as a curable polymer, a gel, a foam, or other fluid that is retained within the balloon via a one-way valve.

Figure 28A:
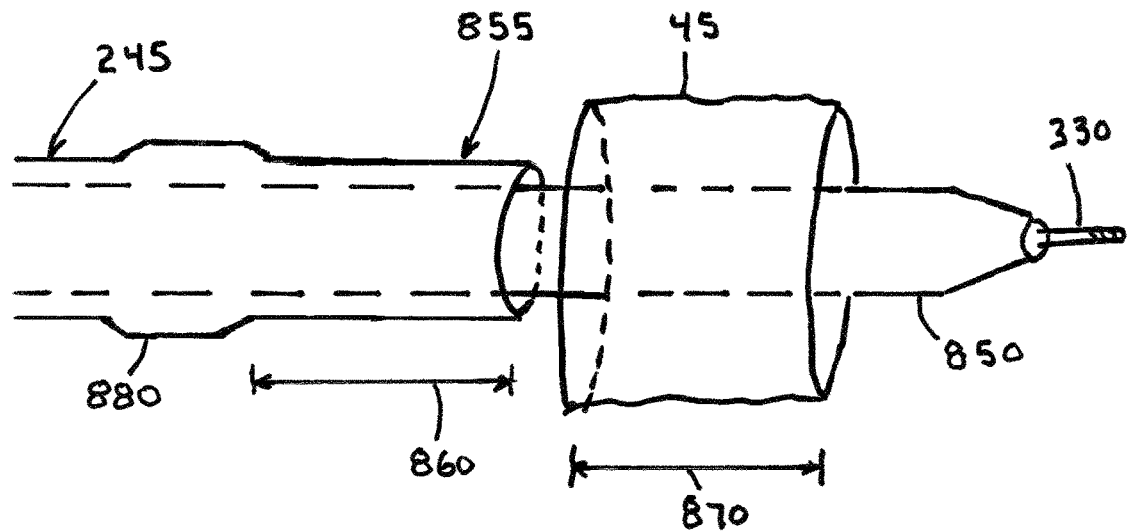
FIG. 28A is a perspective view of an external sheath used to house an occlusion device; the external sheath has a positioning balloon located near its distal end; the external sheath is placed through the lumen of a channel.
Figure 28B:
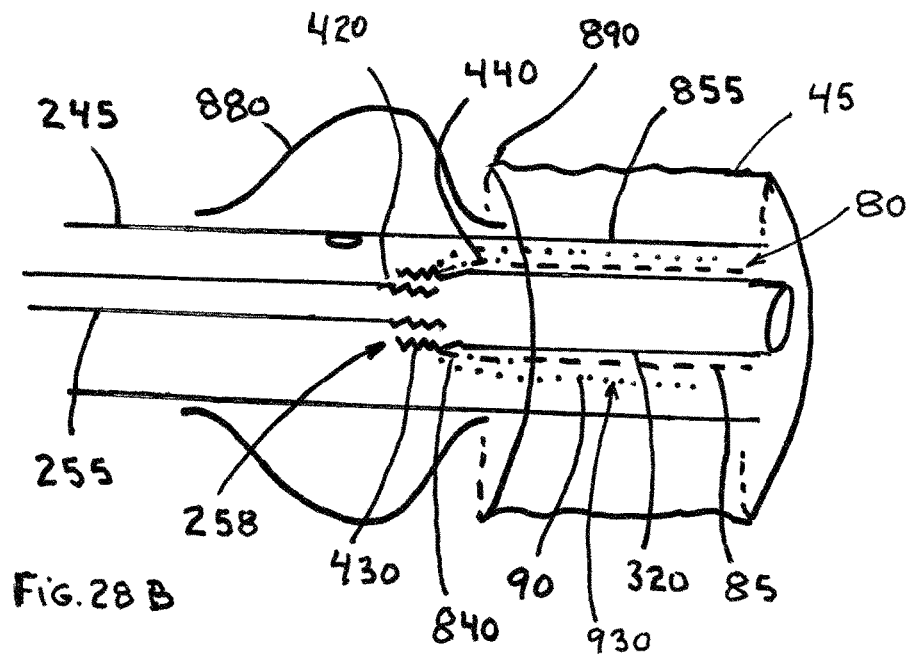
FIG. 28B is a perspective view showing an occlusion device placed within the external sheath of FIG. 28A and having the positioning balloon inflated and positioned adjacent the proximal end of the channel.

A further embodiment for the occlusion device (80) of the present invention is shown in FIGS. 28A-28D. As shown in FIG. 28A, a guidewire (330) and dilator (850) are place across the channel distal opening (830) and an external sheath (245) having a sheath tip (855) with a tip length (860) that is equal or larger than the channel length (870) is passed over the dilator; the tip length (860) is 10 mm (range 5-20 mm); the external sheath (245) has a profile of 6 Fr (range 4-10 Fr). The sheath tip (855) of the external sheath (245) is extended through the channel (45) as shown in FIG. 28B. A positioning balloon (880) located on the external sheath (245) proximal to the sheath tip (855) serves as a locating or positioning balloon (880). The positioning balloon (880) is positioned adjacent the channel proximal end (890) and is inflated to a diameter of at least 5 mm larger than the channel minor distance (65); the positioning balloon (880) has a diameter of 8 mm (range 5-10 mm). Once the external sheath (245) is positioned across the channel (45), the dilator is removed from the external sheath (245) while the guidewire (330) can be maintained (in some embodiments) across the channel (45).

The occlusion device (80) is releasably attached to a delivery tube (255) via a holding assembly (258); the holding assembly (258) can include a threaded receptacle (430) assembly as shown in FIGS. 27B and 27C as described in earlier embodiments of the present invention. The occlusion device (80) is advanced over the guidewire (330) and within the external sheath (245) by advancing a delivery tube (255) having the occlusion device (80) releasably attached to the distal end of the delivery tube (255) via a releasable threaded receptacle (430). The occlusion device (80) is comprised of a SE stent (85) having a specific hinge (190) and strut (200) structure has been discussed in FIGS. 15A-15C of the present patent application. The hinges (190) of this embodiment provides all of the outward expansion forces in expanding the stent from a small diameter configuration to a larger diameter configuration. The hinges do not bend in the circumferential direction do to their hinge radial dimension. The elastic struts of this embodiment provide all of the bending for the stent along the small radius of curvature corners found in the channel. The struts (200) do not contribute to the expansion deformation force of the stent. The stent (85) is attached at the stent proximal end (840) to a stent threaded receptacle (430) that is releasably connected to the delivery tube threads (420). The stent (85) is able to self-expand outwards to a stent body equilibrium diameter (470) that is equal to the channel major distance (70) such that it can fill the interstices of the channel (45).

All of the stent surface or at least a portion of the stent surface including the stent (85) extending from the threaded receptacle (430) to the stent connecting region (500) has a covering (90) attached to its inner or outer surface; the covering (90) does not allow blood to pass through the covering wall structure (930) and hence serves as a barrier for blood flow through the channel (45) once the stent (85) has been released from the external sheath (245) and has formed its expanded configuration. The occlusion device (80) is advanced until it resides within the external sheath (245) at a location that is adjacent to and contained within the channel (45). Fluoroscopic markers can be placed upon the occlusion device (80) or geometric stopping member can be placed on the delivery tube (255) to locate the occlusion device (80) with respect to the sheath and with respect to the channel (45).

Figure 28C:
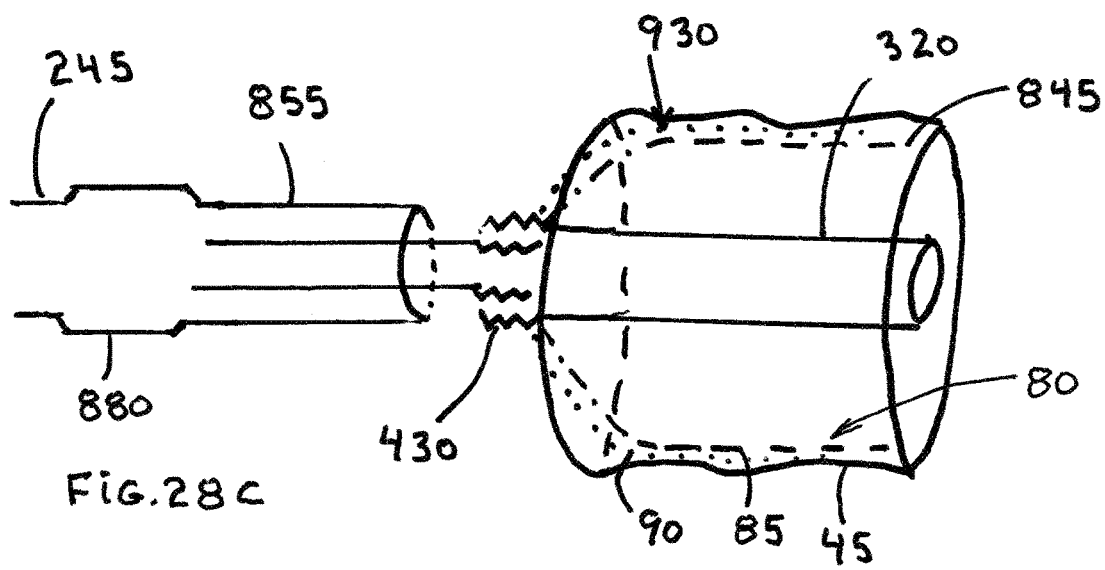
FIG. 28C is a perspective view of the occlusion device of FIG. 28B having the external sheath retracted proximal to the channel and allowing the stent central body to expand into contact with the channel major axis distance and channel minor axis distance.
Figure 28D:
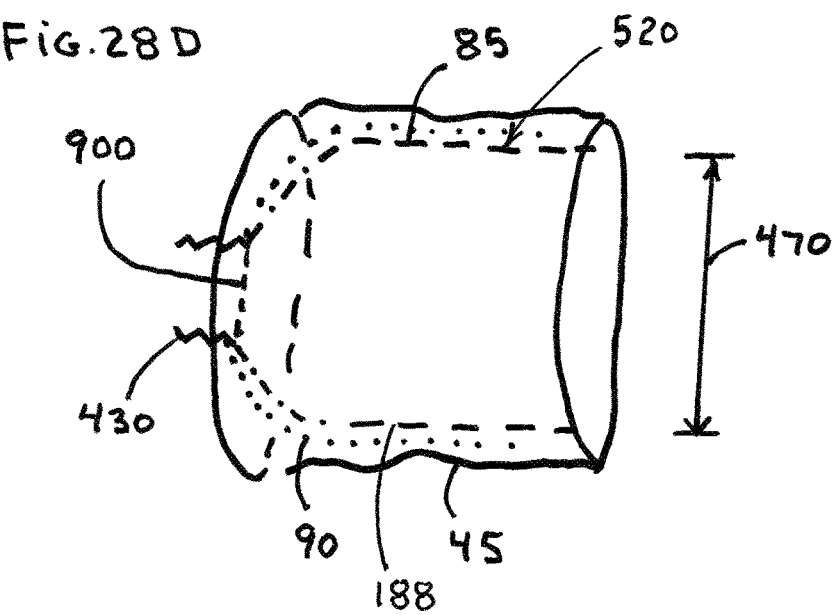
FIG. 28D is a perspective view of the occlusion device of FIG. 28C after the occlusion device has been detached from a delivery tube used to hold the occlusion device and provide repositioning capability to the occlusion device.

Application of tension to the external sheath (245), while holding position for the delivery tube (255) and occlusion device (80) allows the stent (85) to expand outwards into the undulation of the channel (45) as shown in FIG. 28C. The covering (90) is attached to and extends from the threaded receptacle (430) and is attached to the SE stent (85); the covering (90) can extend over the entire stent body (520). The stent (85) can be withdrawn back into the external sheath (245) (to reposition the occlusion device (80), if necessary) by advancing the sheath forward under compression into the channel (45) or by withdrawing the occlusion device (80) under tension into the external sheath (245). If the position of the occlusion device (80) within the channel (45) is acceptable, the occlusion stent (85) can be uncoupled from the delivery tube (255) as shown in FIG. 28D. It is noted that marker bands can be placed on the delivery catheter and on the stent (85) to assist with positioning of the stent (85) within the channel (45). If the positioning balloon (880) is not necessary to locate the occlusion device (80) properly in the channel (45), then a standard external sheath (245), such as a shuttle sheath, can be used to place the occlusion device (80) of the present invention. The device of the present invention can be formed with a guidewire tube or guidewire shaft (320) attached to the threaded receptacle (430) and extending within the stent (85) and out of the stent distal end (845) as shown in FIG. 28B. For the embodiment having an occlusion device (80) that is advanced through the external sheath (245) without following over a guidewire (330), the guidewire tube (320) can be omitted from the present embodiment of the invention; the occlusion device (80) of this embodiment would then be advanced through the external sheath (245) without the occlusion device (80) over a guidewire (330). The embodiment without the guidewire tubing is shown in FIG. 28D; the stent threaded receptacle (430) can be a closed receptacle (900) that does not allow passage of a guidewire (330) therethrough.

The stent wall structure (188) for an embodiment of FIGS. 28A-28D as well as for FIGS. 28E-28H and 28I and for other embodiments that utilize a balloon for expansion of the stent (85) is described in 15A through 16E. The stent (85) has a hinge (190) that has a large (i.e., larger than a strut radial dimension) hinge radial dimension (225) that causes the hinge (190) to open elastically under greater force than a SE stent (85) having a smaller hinge radial dimension (225). The hinge length (222) is greater than the hinge width (215) to provide the hinge with an elastic deformation during expansion deformation without any plastic deformation for the hinge (190). This large expansion force causes the SE stent (85) of the present invention to extend outwards into the narrow channel (45) better than a stent (85) having a smaller radial dimension. The hinges (190) provide all of the outward expansion forces of the stent from a smaller diameter configuration to a larger diameter configuration. The struts (200) of the present stent (85) have a very thin strut radial dimension (230) that is much smaller (i.e., less than 50% of the hinge radial dimension (225)) than the hinge radial dimension (225); this small strut radial dimension (230) allows the strut (200) to remain elastic around a tight bend of the channel (45) but yet can bend easily around tight radius of curvature bends that are found in the long narrow channels (45) of the perivalvular leak. The elastic struts (200) provide all of the bending that occurs in the circumferential direction along the curves of the oblong-shaped channel. The strut width (220) is much greater than the hinge width (215); the large hinge radial dimension (225) provides the large elastic force during expansion deformation and the hinge (190) cannot bend in the radial direction (218); the large strut width (220) allows the strut (200) to expand outwards without bending in the circumferential direction (235); the struts (200) only bend in the radial direction (218) due to their smaller strut radial dimension (230). Thus the hinge (190) and strut (200) structure as described herein and also described patent applications that are referenced will cause the stent (85) to expand out better than a standard stent. Furthermore, the hinges (190) have a larger hinge radial dimension (225) that extends outwards in a radial direction from the stent outer surface and will form a frictional lock with the undulations (78) of the channel (45) to assist in preventing migration of the occlusion device (80) in the channel (45). A standard stent with a large hinge radial dimension (225) will have a large expansion dilation force but cannot bend to form the small radius of curvature bends found in a channel (45). A standard stent with thin radial dimension can bend to form the small radius of curvature bends but does not have enough outward force to extend outwards and fill the channel (45). The shape of the stent struts (200) to form a concave shape as described in FIGS. 16A-16E will allow the stent struts (200) to follow along and contact the channel (45) (along a perimeter of the channel (45)) thereby ensuring that the occlusion device (80) cannot itself have a leakage of blood between the occlusion device (80) and the luminal surface of the channel (45).

Figure 28E:
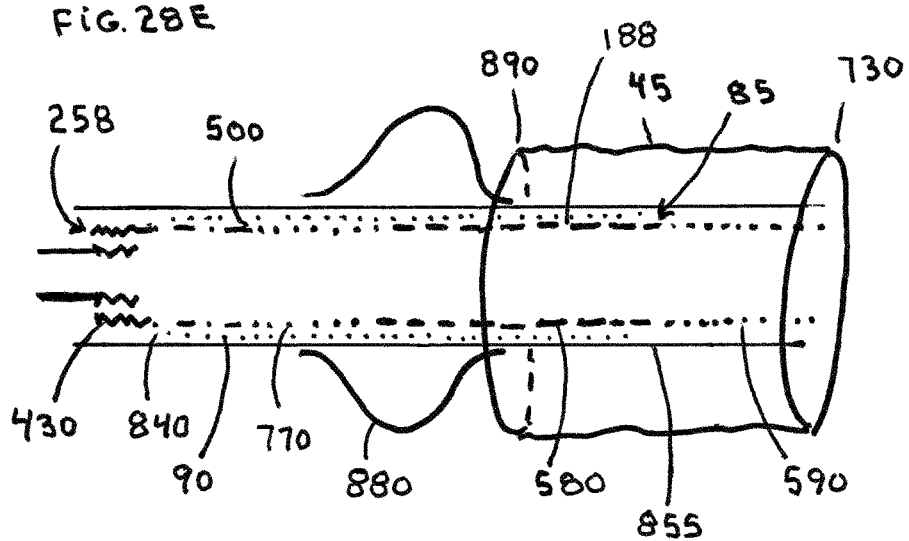
FIG. 28E is an occlusion device positioned within an external sheath having a positioning balloon; the occlusion device has a stent distal body, a stent central body, and a stent proximal body.

FIGS. 28E-28H and 28J show an embodiment of the occlusion device (80) and method that is similar to the embodiment shown in FIGS. 28A-28D. The occlusion device (80) comprises a SE stent (85) that is delivered within an external sheath (245); the external sheath (245) has a positioning balloon (880) located near its distal end just proximal to the sheath tip (855) as shown in FIG. 28E. The stent (85) has a stent proximal body (770), a stent central body (580), and a stent distal body (590); the stent (85) has a stent connecting region (500) that attaches the stent body (520) to a threaded receptacle (430) at the stent proximal end (840). A covering (90) is attached to the stent connecting region (500), stent proximal body (770). and stent central body (580) in a manner similar to that described in other embodiments to ensure that blood cannot flow through the stent wall structure (188) and thereby the covering (90) prevents blood flow through the channel (45).

Figure 28F:
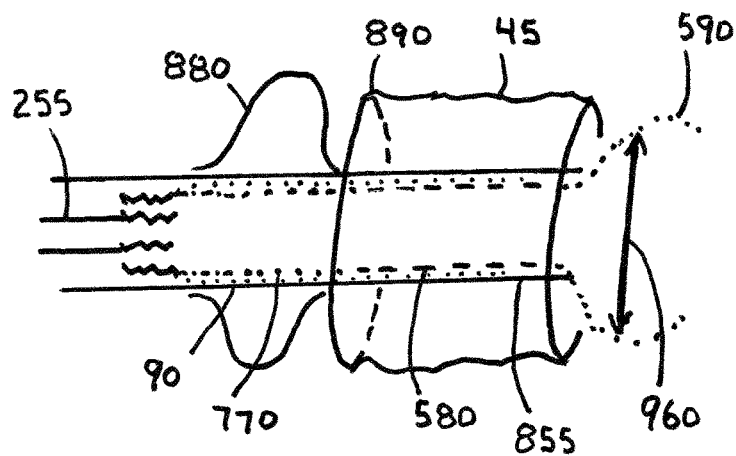
FIG. 28F is the occlusion device of FIG. 28E having the stent distal body extending out of the external sheath at a location distal to the channel.
Figure 28G:
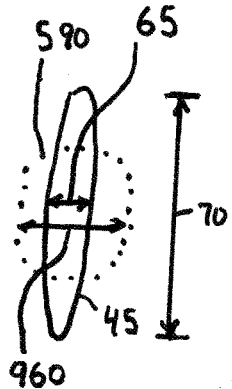
FIG. 28G is a cross-sectional view of the stent distal body showing a stent distal body diameter that is larger than a channel minor distance.
Figure 28H:
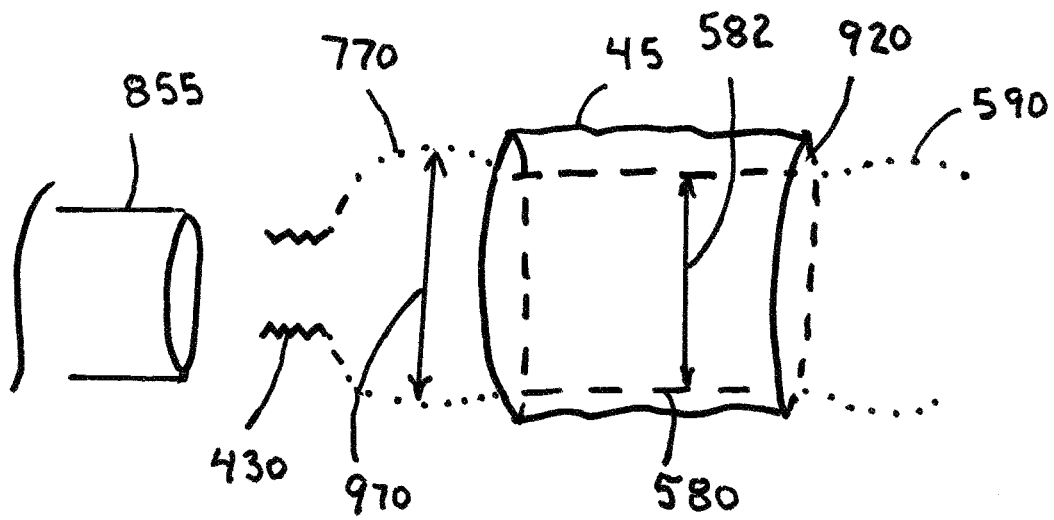
FIG. 28H is the occlusion device of FIG. 28F having the external sheath retracted proximal to the channel allowing the stent proximal body to expand outwards to a stent proximal body diameter and allowing the stent central body to expand outwards to contact the channel major axis distance and channel minor axis distance.
Figure 28J:
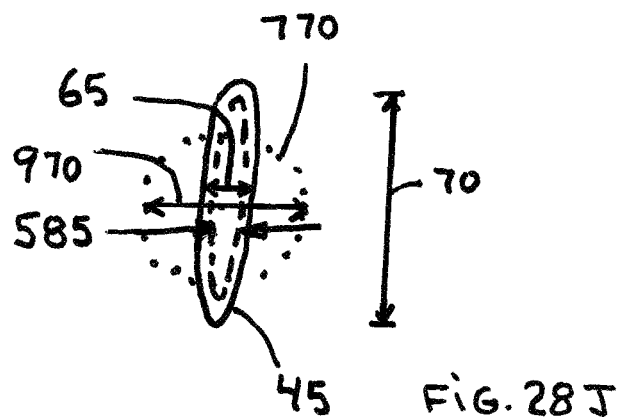
FIG. 28J is a cross-sectional view of the stent proximal body showing a stent proximal body diameter that is larger than a channel minor distance.

The sheath tip (855) is positioned into the channel (45) and the positioning balloon (880) is inflated and located adjacent to the channel inlet end (890) as shown in FIG. 28F to properly locate the occlusion device (80) within the channel (45). The occlusion device (80) is advanced distally such that the stent distal body (590) extends outwards to a self-expanded configuration adjacent to the channel distal end (730). The stent distal body (590) has a stent distal body diameter (960) that is greater than the channel minor distance (65) as shown in FIG. 28G. The stent distal body (590) has formed a rounded cross-sectional shape with a stent distal body diameter (960) that is larger than the channel minor distance (65) and larger than the stent central body minor distance (585) by at least 5 mm. The stent distal body (590) can also have a stent distal body diameter (960) that can be greater than the channel major distance (70), if necessary. The expanded configuration for the stent distal body (590) ensures that the occlusion device (80) cannot migrate proximally relative to the channel (45). The positioning balloon (880) can then be deflated and the external sheath (245) can be withdrawn under tension while maintaining the position of the occlusion device (80) fixed within the channel (45) as shown in FIG. 28H. The stent central body (580) expands outwards into contact with the channel major distance (70) and the channel minor distance (65) to fill the channel lumen (920) with the expanded occlusion stent (85). The stent central body major distance (582) is greater than the stent central body minor distance (585) which is constrained by the channel minor distance (65) and hence they share a similar minor axis distance. The stent proximal body (770) expands outwards to a rounded cross-sectional shape via the elastic expansion force contained in the Nitinol frame to a stent proximal body diameter (970) that is greater than the channel minor distance (65) by at least 5 mm as shown in FIGS. 28H and 28J and greater than the stent central body minor distance (585) by at least 5 mm. The stent proximal body (770) can also expand outwards such that the stent proximal body diameter (970) is greater than the channel major distance (70), if necessary to prevent migration of the occlusion device (80) in the channel (45).

The wall structure for the stent body (520) of the present embodiment can be any wall structure used in a SE stent (85) used in the vasculature. The wall structure can also be the than which is described in FIGS. 15A-15B which has hinges (190) and struts (200) that can expand with a greater outward force provided by the large hinge radial dimension (225) and can bend easily around the tight turns of a channel (45) due to the very small strut radial dimension (230) relative to the hinge radial dimension (225).

One advantage of this occlusion device (80) embodiment over standard occlusion devices currently being used in the clinic is that positioning of the stent distal body (590) adjacent to the channel distal end (730) is enhanced (over a standard device that relies upon a distal bulb for positioning within a channel (45)) due to the presence of a positioning balloon (880) and inflation of the positioning balloon (880) that is located near the distal end (700) of the external sheath (245). The positioning of the present invention is not dependent upon the oversized diameter of a standard stent distal bulb or the strength of a standard stent wall structure found in other occlusion devices. The stent distal body diameter (960) of the present invention can be smaller than a distal bulb diameter of a standard occlusion device that depends upon a distal bulb located adjacent to the channel distal end (730) to position the occlusion device. The stent distal minor distance (760) of the present invention is only 5 mm larger (range 5-10 mm larger) than the channel minor distance (65) and thereby does not protrude into the blood flow path or adversely affect the function of the valve leaflets of the valve having the perivalvular leak. The stent proximal body diameter (970) is also only 8 mm larger (range 5-10 mm larger) than the channel minor distance (65) and does not protrude adversely into the blood flow pathway due to a similar rationale as described for the stent distal minor distance (760).

Reference numerals used to describe structural elements found in the various embodiments of the present invention may be applied similarly to describe structural elements using the same reference numerals in other embodiments. The present invention is not limited to the embodiments described and it is understood that specific structural elements found in an embodiment can be applied to other embodiments without deviating from the present invention.

The invention claimed is:

1. An occlusion device for occluding blood flow within an oblong channel, the oblong channel having a cross-sectional shape with a channel major axis distance that is larger than a channel minor axis distance, the oblong channel extending axially from a channel proximal end to a channel distal end, the oblong channel being located between the tissues of a native heart valve and an implanted heart valve, the occlusion device comprising;

A. an occlusion balloon positioned at a distal end of an elongated delivery tube,
　B. a stent having a stent central body, said stent central body being mounted onto a balloon outside surface of said occlusion balloon,
　C. said stent being contained in a smaller diameter configuration within an external sheath and being self-expandable to a larger diameter configuration upon release from said external sheath, said stent central body able to expand to a stent central body diameter equal to or greater than the channel major axis distance,
　D. said stent being fixedly attached to said occlusion balloon, said occlusion balloon being fixedly attached to a portion of a holding assembly, said portion of said holding assembly being releasably attached to said elongated delivery tube, said elongated delivery tube having an inflation lumen that is able to direct inflation medium from said elongated delivery tube to said occlusion balloon,
　E. said occlusion balloon being implantable into the channel along with said stent in said larger diameter configuration,
　F. said occlusion balloon having a balloon central body positioned adjacent to said stent central body, said balloon central body being inflatable to enlarge said stent central body to a stent central body major diameter that is equal to the channel major axis distance,
　G. whereby said occlusion device occludes blood flow within the oblong channel.

2. The occlusion device of claim 1 wherein said occlusion balloon is attached to said stent central body, said occlusion balloon providing a barrier preventing blood flow within the oblong channel.

3. The occlusion device of claim 1 further comprising a covering, said covering being attached to a stent surface of said stent central body, said covering being formed from a thin flexible material that provides a barrier for preventing blood flow within the oblong channel.

4. The occlusion device of claim 1 wherein said occlusion balloon has a balloon distal body that extends distally beyond a stent central body distal end, said balloon distal body being expandable to a balloon distal body diameter greater than the channel minor axis distance.

5. The occlusion balloon of claim 1 wherein said holding assembly provides a passage for inflation medium to leak out of said occlusion balloon following release of said holding assembly from said delivery tube.

6. The occlusion balloon of claim 1 wherein said occlusion device comprises a flapper valve to retain said inflation medium within said occlusion balloon following inflation of said occlusion balloon.

7. The occlusion balloon of claim 1 further comprising a stent distal body, said stent distal body being located on said balloon outside surface adjacent to said balloon distal body and located distal to said stent central body, and able to be located distal to the channel distal end, said stent distal body able to expand to a stent distal body diameter that is greater than the channel minor axis distance.

8. The occlusion balloon of claim 7 wherein said stent distal body diameter is at least 5 mm greater than the channel minor axis distance.

9. The occlusion balloon of claim 1 further comprising a stent proximal body, said stent proximal body being located on said balloon outside surface and located proximal to said stent central body, and able to be located proximal to the channel proximal end, said stent proximal body able to expand to a stent proximal body diameter that is greater than the channel minor axis distance.

10. The occlusion device of claim 1 wherein,
A. said external sheath having a sheath tip, said sheath tip being located at an external sheath distal end, said sheath tip holding said stent in said smaller diameter configuration, said sheath tip having a sheath tip length that is equal to or greater than the channel length,
B. said external sheath having a positioning balloon located proximal to said sheath tip, said positioning balloon able to expand to a positioning balloon diameter that is greater than the channel minor axis distance, said positioning balloon being positionable adjacent the channel proximal end, said positioning balloon able to expand to a diameter greater than the channel minor axis dimension.

11. The occlusion device of claim 10 wherein;
A. said stent central body has a stent wall structure formed from self-expanding hinges, said self-expanding hinges providing all outward expansion forces to expand said stent from said smaller diameter configuration to said larger diameter configuration, said stent wall structure formed from elastic struts, said elastic struts providing all circumferential bending of said stent in the oblong channel,
B. said hinges have a hinge radial dimension that is greater than a strut radial dimension such that said hinge provides all of said outward expansion forces to expand said stent central body to said stent major axis diameter and said strut is able to provide all of the elastic bending around tight corners of the oblong channels.

12. The occlusion device of claim 11 wherein said strut can form small radius of curvature bends of 2 mm via an elastic deformation.

13. The occlusion device of claim 11 wherein said hinges having a hinge length that is longer than a hinge width to allow said hinges to expand outwards during an expansion deformation via an elastic self-expansion deformation.

14. The occlusion device of claim 10 further comprising a stent distal body, said stent distal body being located distal to said stent central body, said stent distal body able to be located distal to the oblong channel, said stent distal body having a stent distal body diameter configured to be larger than the channel minor axis distance.

15. The occlusion device of claim 10 further comprising a stent proximal body, said stent proximal body being located proximal to said stent central body, said stent proximal body able to be positioned proximal to the oblong channel, said stent proximal body having a stent proximal body diameter configured to be larger than the channel minor axis distance.

16. The occlusion device of claim 10 wherein said stent distal body diameter is less than said stent central body diameter.

17. The occlusion device of claim 10 wherein said stent proximal body diameter is less than said stent central body diameter.

18. The occlusion device of claim 10 wherein said portion of said holding assembly is released from said delivery catheter, said stent being implantable into the channel.

19. The occlusion device of claim 10 wherein said portion of said holding assembly is releasably attached to said delivery catheter, said stent being retrievable into said external sheath for repositioning said stent in the channel, said stent being able to be implanted into the channel.

20. An occlusion device for occluding fluid flow within an oblong channel of the body, the oblong channel having a cross-sectional shape with a channel major axis distance that is larger than a channel minor axis distance, the oblong channel extending axially from a channel proximal end to a channel distal end, the occlusion device comprising;
A. an occlusion balloon positioned at a distal end of an elongated delivery tube,
B. a stent having a stent central body, said stent central body being mounted onto a balloon outside surface,
C. said stent being deliverable in a smaller diameter configuration and being self-expandable to a larger diameter configuration, said stent central body able to expand to a stent central body diameter equal to the channel major axis distance,
D. said stent being fixedly attached to said occlusion balloon, said occlusion balloon being releasably attached to said elongated delivery tube, said elongated delivery tube having an inflation lumen that is able to direct inflation medium from said delivery tube to said occlusion balloon,
E. said occlusion balloon having a balloon distal body that extends distally beyond a stent central body distal end, said balloon distal body being expandable to a balloon distal body diameter greater than the channel minor axis distance,
F. said occlusion balloon having a balloon central body positioned within said stent central body, said balloon central body being inflatable to enlarge said stent central body to a stent central body major diameter that is equal to the channel major axis distance, G. said occlusion balloon being implantable into the channel along with said stent in said larger diameter configuration, whereby said occlusion device occludes the blood flow within the oblong channel.

\* \* \* \* \*